US009893301B2

(12) United States Patent
Park et al.

(10) Patent No.: US 9,893,301 B2
(45) Date of Patent: Feb. 13, 2018

(54) HETEROCYCLIC COMPOUNDS AND ORGANIC LIGHT-EMITTING DEVICES INCLUDING THE SAME

(71) Applicant: SAMSUNG DISPLAY CO., LTD., Yongin, Gyeonggi-do (KR)

(72) Inventors: Bum-Woo Park, Yongin (KR); Yoon-Hyun Kwak, Yongin (KR); Sun-Young Lee, Yongin (KR); Jong-Won Choi, Yongin (KR); Wha-Il Choi, Yongin (KR); So-Yeon Kim, Yongin (KR); Ji-Youn Lee, Yongin (KR); Jin-Young Yun, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 391 days.

(21) Appl. No.: 13/919,843

(22) Filed: Jun. 17, 2013

(65) Prior Publication Data

US 2014/0027741 A1 Jan. 30, 2014

(30) Foreign Application Priority Data

Jul. 25, 2012 (KR) ........................ 10-2012-0081404

(51) Int. Cl.
*H01L 51/00* (2006.01)
*C07D 491/048* (2006.01)
(Continued)

(52) U.S. Cl.
CPC ...... *H01L 51/0074* (2013.01); *C07D 491/048* (2013.01); *C07D 493/04* (2013.01);
(Continued)

(58) Field of Classification Search
None
See application file for complete search history.

(56) References Cited

U.S. PATENT DOCUMENTS 5,635,308 A 6/1997 Inoue et al.
5,645,948 A 7/1997 Shi et al.
(Continued)

FOREIGN PATENT DOCUMENTS

CN 101659593 3/2010
CN 102264698 11/2011
(Continued)

OTHER PUBLICATIONS

Tang, et al., Organic electroluminescent diodes, American Institute of Physics, Sep. 1987, p. 913-915, vol. 51, No. 12.
(Continued)

*Primary Examiner* — J. L. Yang
(74) *Attorney, Agent, or Firm* — H.C. Park & Associates, PLC

(57) ABSTRACT

Heterocyclic compounds, synthetic methods for preparing the same, and organic light-emitting display devices comprising the same are described. The subject heterocyclic compounds may comprise an aromatic ring or a heteroaromatic ring fused with a carbazole, dibenzothiophene, or dibenzofurane derivative, the compounds featuring rigid backbone structures with high glass transition temperatures and high melting points. The subject heterocyclic compounds may exhibit high electrical stability, improved charge transport ability, high heat resistance and improved light-emitting properties when used in organic light-emitting devices. Organic light-emitting display devices prepared according to the present invention exhibit lower driving voltages, increased luminescent efficiencies and longer lifetimes.

20 Claims, 1 Drawing Sheet

(51) Int. Cl.

| | |
|---|---|
| ***C07D 493/04*** | (2006.01) |
| ***C09K 11/06*** | (2006.01) |
| *H01L 51/50* | (2006.01) |

(52) U.S. Cl.

CPC .......... *C09K 11/06* (2013.01); *H01L 51/0071* (2013.01); *H01L 51/0073* (2013.01); *H01L 51/0067* (2013.01); *H01L 51/0072* (2013.01); *H01L 51/0081* (2013.01); *H01L 51/5012* (2013.01); *H01L 51/5016* (2013.01); *H01L 51/5056* (2013.01); *H01L 51/5072* (2013.01); *H01L 2251/308* (2013.01)

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 2008/0319239 | A1 | 12/2008 | Buesing |
| 2010/0032658 | A1 | 2/2010 | Lee et al. |
| 2011/0168992 | A1 | 7/2011 | Bae et al. |
| 2011/0253944 | A1 | 10/2011 | Han et al. |
| 2014/0001442 | A1 | 1/2014 | Lee et al. |
| 2014/0027741 | A1 | 1/2014 | Park et al. |
| 2015/0349276 | A1 | 12/2015 | Jang et al. |

FOREIGN PATENT DOCUMENTS

| | | | |
|---|---|---|---|
| CN | 102449106 | | 5/2012 |
| CN | 103509036 | A | 1/2014 |
| DE | 102013214399 | | 1/2014 |
| JP | 08-012600 | A | 1/1996 |
| JP | 2000-003782 | A | 1/2000 |
| JP | 2014-9230 | | 1/2014 |
| JP | 2016-503761 | | 2/2016 |
| KR | 10-2008-0081318 | | 9/2008 |
| KR | 10-2010-0003624 | A | 1/2010 |
| KR | 10-2010-0007780 | A | 1/2010 |
| KR | 10-2010-0034719 | A | 4/2010 |
| KR | 10-2010-0108924 | A | 10/2010 |
| WO | 2010/110553 | | 9/2010 |
| WO | 2010/114264 | A2 | 10/2010 |
| WO | 2010/126234 | | 11/2010 |

OTHER PUBLICATIONS

Adachi, et al., Confinement of charge carriers and molecular excitons within 5-nm-thick emitter layer in organic electroluminescent devices with a double heterostructure, American Institute of Physics, Aug. 1990, p. 531-533,vol. 57, No. 6.

Sakamoto, et al., Synthesis, Characterization, and Electron-transport Property of Perfluorinated Phenylene Dendrimers, American Chemical Society, 2000, p. 1832-1833, vol. 122, No. 8.

Yamaguchi, et al., Diphenylamino-Substituted 2, 5-Diarylsiloles for Single-Layer Organic Electroluminescent Devices, The Chemical Society of Japan, 2001, p. 98-99.

Chinese Office Action issued by the Chinese Patent Office on Aug. 2, 2016 in the examination of the Chinese Patent Application No. 201310302873.3, which corresponds to U.S. Appl. No. 13/919,843 "Request for Entry" is attached.

David Curiel et al., "Synthesis and Characterization of New Carbazolocarbazoles: Toward π-Extended N-Fused Heteroacenes" , Organic Letters, 2010, vol. 12, No. 14, pp. 3164-3167.

Marvin L. Tedjamulia, "Angular Polycyclic Thiophenes Containing Two Thiophene Rings", J. Heterocyclic Chem., vol. 21, pp. 321-325.

Taiwanese Office Action issued by Taiwan Intellectual Property Office on Dec. 27, 2016 in corresponding Taiwanese Patent Application No. 102123441 which also claims Korean Patent Application No. 10-2012-0081404 as its priority application, together with Request for Entry of the Accompanying Office Action attached herewith.

Korean Registration Determination Certificate issued by KIPO on Feb. 27, 2017 in corresponding Korean Patent Application No. 10-2012-0081404, together with Request for Entry attached herewith.

Japanese Office Action issued by JPO on Jun. 6, 2017 in corresponding Japanese Patent Application No. 2013-150575 which also claims Korean Patent Application No. 10-2012-0081404 as its priority application, together with Request for Entry of the Accompanying Office Action attached herewith.

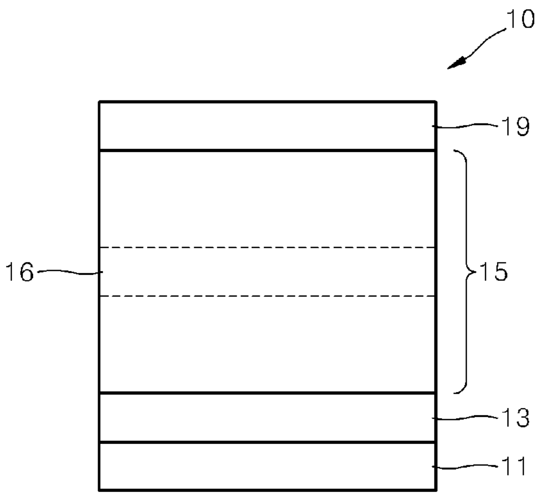
10
19
16
15
13
11

HETEROCYCLIC COMPOUNDS AND ORGANIC LIGHT-EMITTING DEVICES INCLUDING THE SAME

CLAIM OF PRIORITY

This application makes reference to, incorporates the same herein, and claims all benefits accruing under 35 U.S.C. § 119 from an application for HETEROCYCLIC COMPOUND AND ORGANIC LIGHT-EMITTING DEVICE INCLUDING THE SAME earlier filed in the Korean Intellectual Property Office on 25 Jul. 2012 and there duly assigned Serial No. 10-2012-0081404.

BACKGROUND OF THE INVENTION

1. Field of the Invention

The present invention relates to heterocyclic compounds and, more specifically, to fused ring heterocyclic compounds and organic light-emitting devices including the same. Additionally, the present invention relates to organic light-emitting devices including the subject heterocyclic compounds and having improved light emitting properties.

2. Description of the Related Art

Organic light-emitting devices (OLEDs), which are self-emitting devices, have advantages such as wide viewing angles, excellent contrast, quick response, high brightness and excellent driving voltage characteristics and can provide multicolored images. Due to these characteristics, OLEDs have been receiving a growing level of attention.

An existing organic light-emitting device has a structure that includes an anode disposed on a substrate, a hole transport layer (HTL), an emission layer (EML), an electron transport layer (ETL) and a cathode that are sequentially disposed upon one another. The HTL, the EML, and the ETL are normally formed of organic compounds. When a voltage is applied between the anode and the cathode, holes injected from the anode move to the EML via the HTL, and electrons injected from the cathode move to the EML via the ETL. The holes and electrons (carriers) recombine in the EML to generate excitons. When the exitons drop from an excited state to a ground state, light is emitted.

A major factor affecting luminescent efficiency of an organic light-emitting device is the structure of the organic luminescent material used to construct the device. Fluorescent materials have been widely used as organic light-emitting materials, but they may have limited emission efficiency due to having a mere 25% probability of being in an excited singlet state. Meanwhile, phosphorescent materials have a 25% probability of being in an excited singlet state and a 75% of probability of being in an excited triplet state, and thus they may improve emission efficiency up to four times as compared with fluorescent materials, based on theoretical electroluminescence mechanisms, and they may achieve a 100% internal quantum efficiency. Thus, the use of phosphorescent materials in organic light-emitting devices is gradually increasing.

Anthracene derivatives are typical organic light-emitting materials. However, an organic light-emitting device using an anthracene derivative in which two or three anthracene moieties are linked in a conjugated system may have a narrow energy gap, a low blue-light color purity, and a low emission efficiency. Thus, improving upon the performance obtainable with anthracenes is desirable.

4,4'-Bis(carbazole-9-yl)biphenyl (CBP) is in wide use as a phosphorescent host material, but it is not suitable for green-light emission due to having a wide bandgap and reduced emission efficiency. It is also not easy to control hole or electron mobility with this material to adjust the charge balance.

These existing organic light-emitting materials are not satisfactory in emission characteristics, including emission efficiency, and thus there is still a demand for improvement.

SUMMARY OF THE INVENTION

The present invention provides heterocyclic compounds that are useful for forming the organic layer of an organic light-emitting device.

The present invention also provides an organic light-emitting device that includes at least one of the above heterocyclic compounds and thus has improved emission efficiency and lifetime.

The present invention also provides a high-efficiency, long lifetime organic light-emitting display apparatus including the organic light-emitting device.

According to an embodiment of the present invention, there is provided a heterocyclic compound represented by Formula 1 below:

<Formula 1>

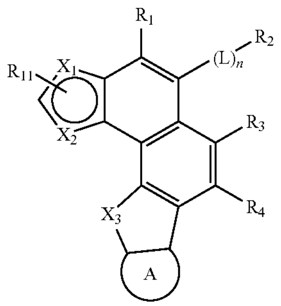

$X_1$ and $X_2$ in Formula 1 each independently being one selected from —C($R_{12}$)—, —N—, —N($R_{13}$)—, —O—, and —S—, and at least one of $X_1$ and $X_2$ being selected from —N—, —N($R_{13}$)—, —O—, and —S—;

$X_3$ being selected from —N($R_{21}$)—, —O—, and —S—;

$R_1$, $R_2$, $R_3$, $R_4$, $R_{11}$, $R_{12}$, $R_{13}$, and $R_{21}$ each independently being one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, and a —N($Q_1$)($Q_2$) group, $Q_1$ and $Q_2$ each independently being one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_2$-$C_{30}$ heteroaryl group;

L being selected from a substituted or unsubstituted $C_6$-$C_{30}$ arylene group and a substituted or unsubstituted $C_2$-$C_{30}$ heteroarylene group;

n being an integer of 0 to 3;

$A_4$ being selected from a substituted or unsubstituted $C_6$-$C_{30}$ aromatic ring and a substituted or unsubstituted $C_2$-$C_{30}$ heteroaromatic ring; and $R_{11}$ and $R_{12}$ being selectively bound together to form one of a substituted or unsubstituted $C_6$-$C_{30}$ aromatic ring and a substituted or unsubstituted $C_2$-$C_{30}$ heteroaromatic ring.

The heterocyclic compound may be represented by one of Compounds 2a to 2t below:

<Formula 2a>

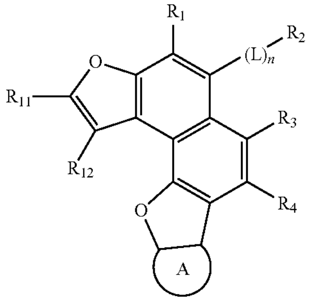

<Formula 2b>

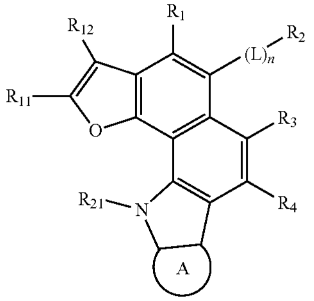

<Formula 2c>

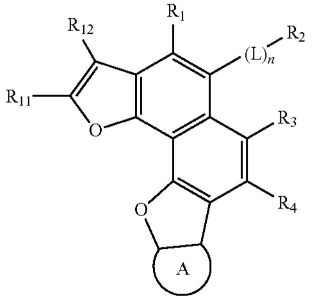

<Formula 2d>

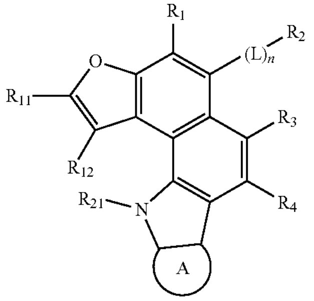

-continued

<Formula 2e>

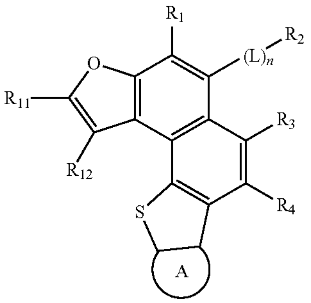

<Formula 2f>

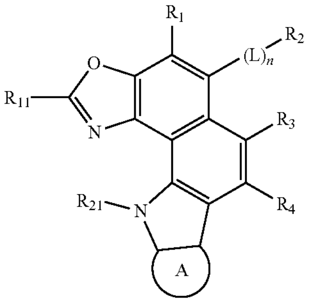

<Formula 2g>

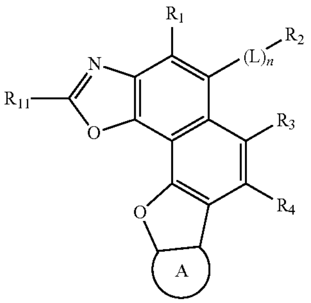

<Formula 2h>

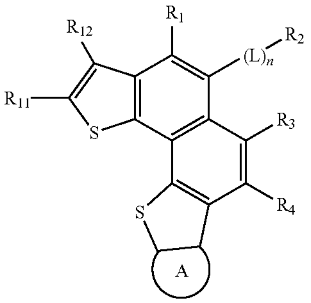

<Formula 2i>

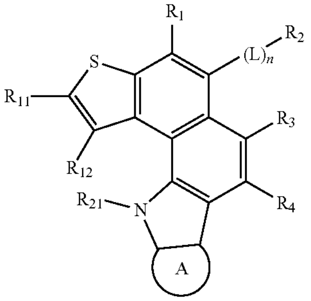

-continued
<Formula 2j>
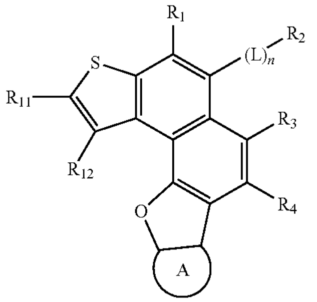
<Formula 2k>
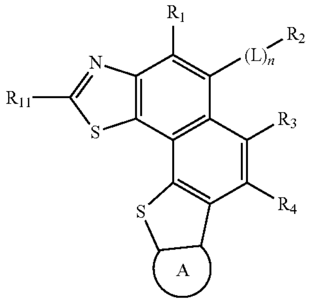
<Formula 2l>
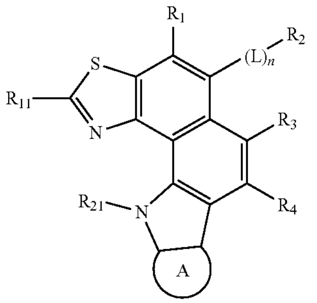
<Formula 2m>
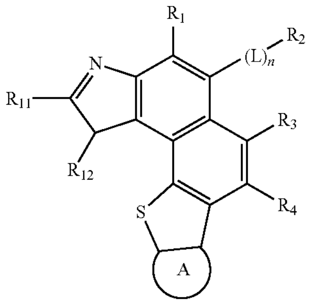
<Formula 2n>
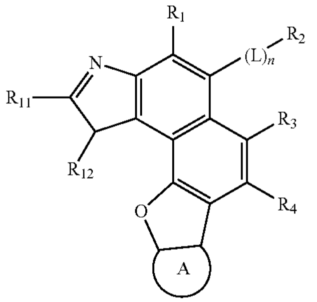
-continued
<Formula 2o>
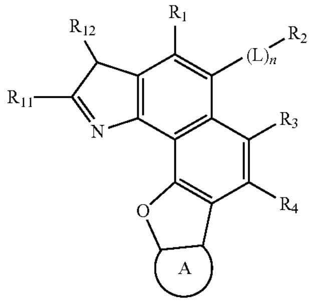
<Formula 2p>
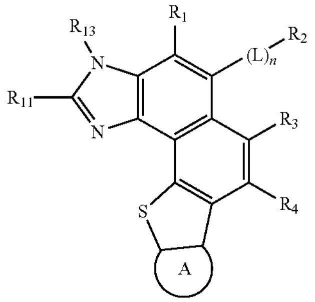
<Formula 2q>
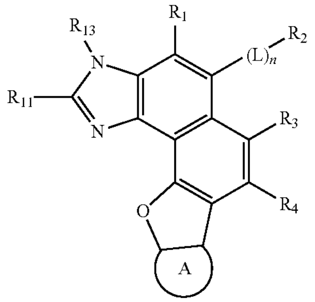
<Formula 2r>
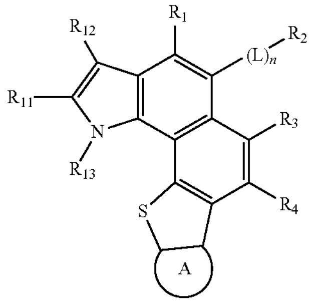
<Formula 2s>
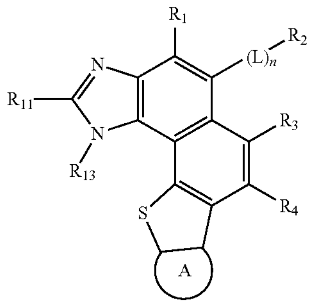

-continued
<Formula 2t>
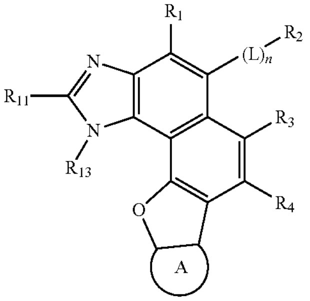
wherein, in Formulae 2a to 2t, $R_1$, $R_2$, $R_3$, $R_4$, $R_{11}$, $R_{12}$, $R_{13}$, $R_{21}$, L, n, and A ring are as defined in Formula 1.
The heterocyclic compound may be one of Compounds 1 to 56 below.
1
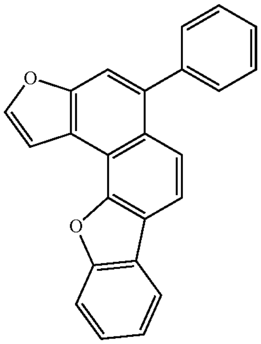
2
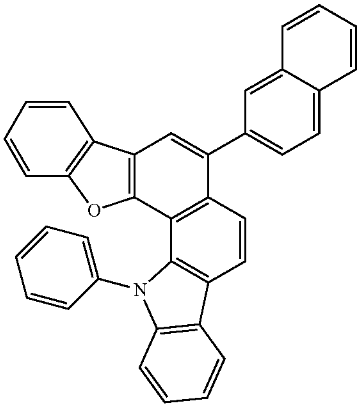
3
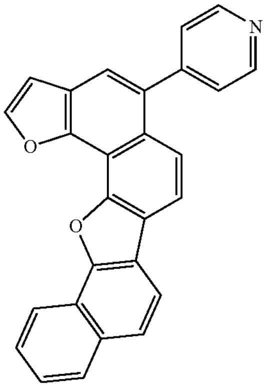
-continued
4
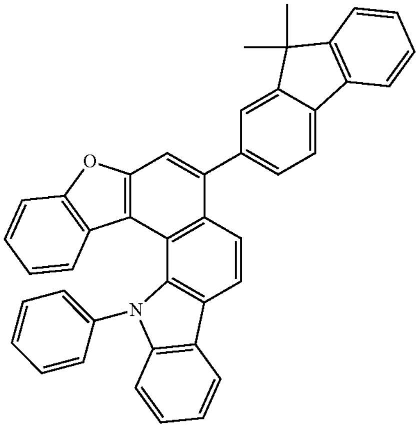
5
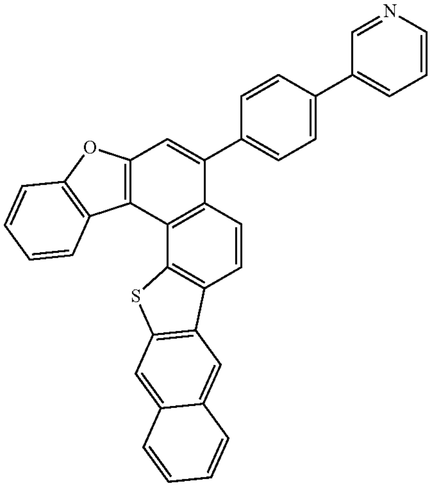
6
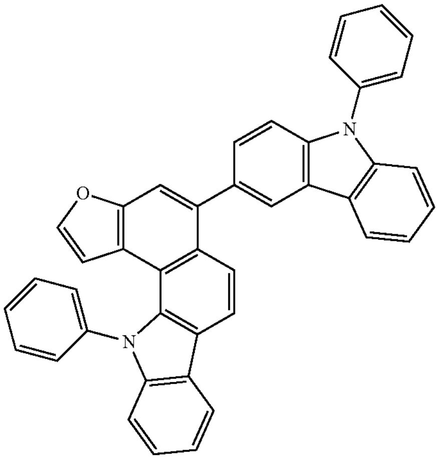

-continued
7
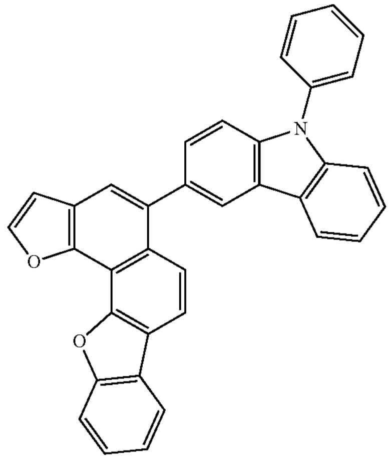
8
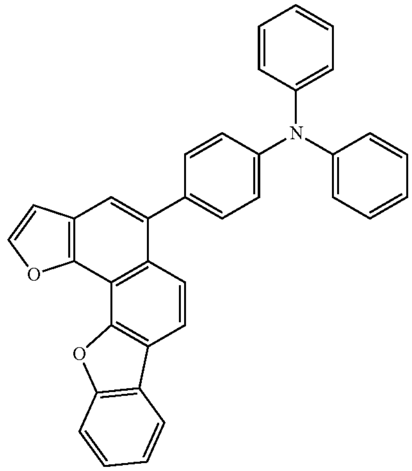
9
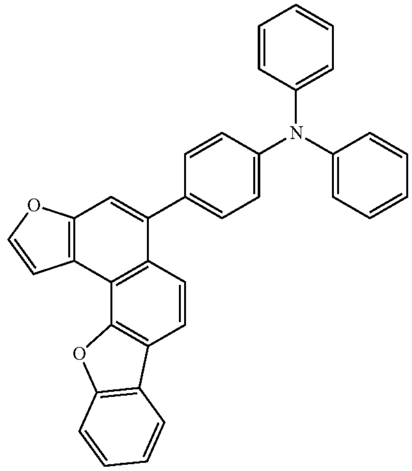
-continued
10
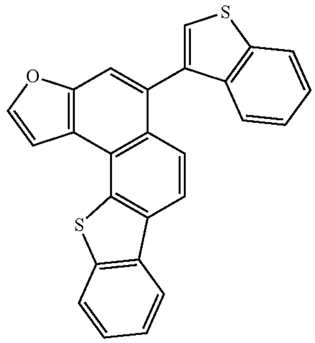
11
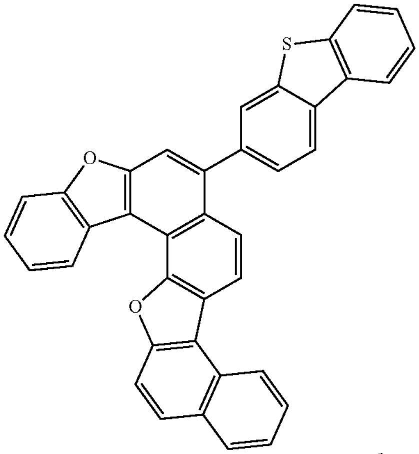
12
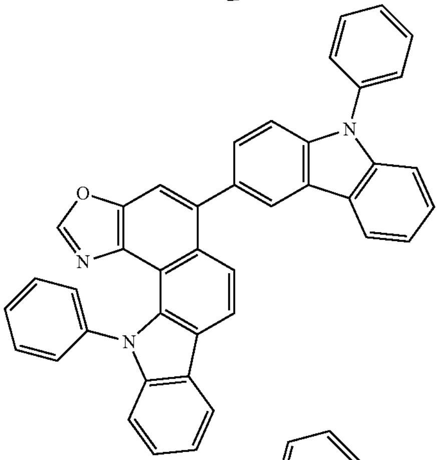
13
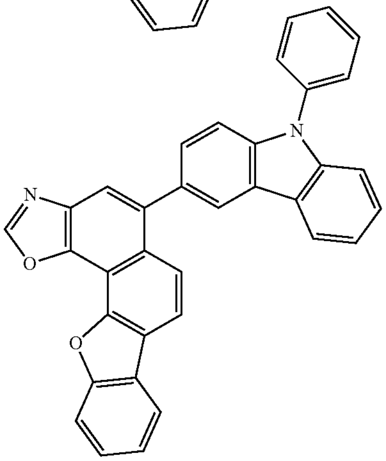

-continued
14
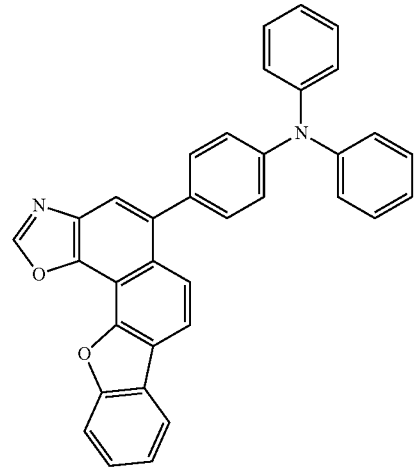
15
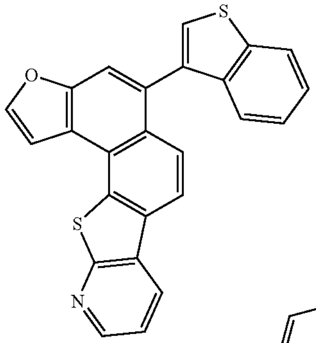
16
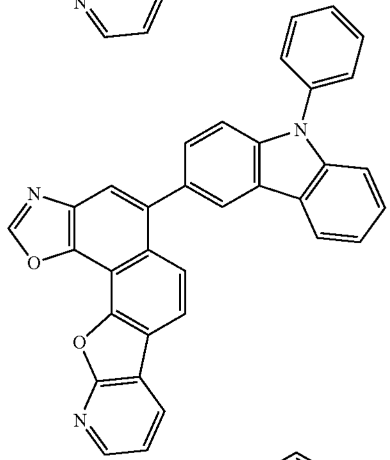
17
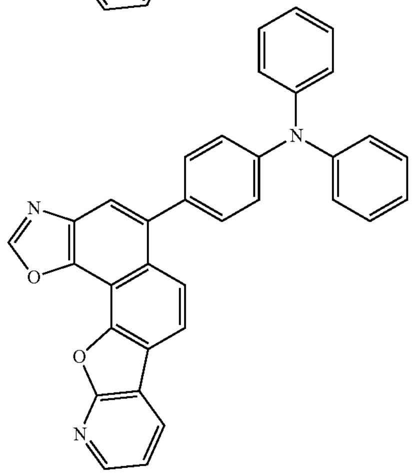
-continued
18
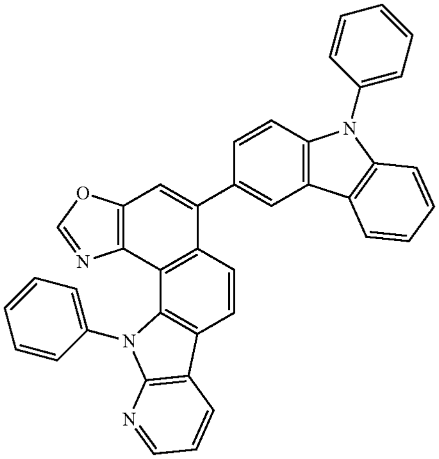
19
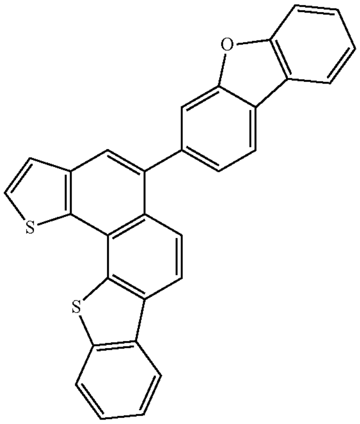
20
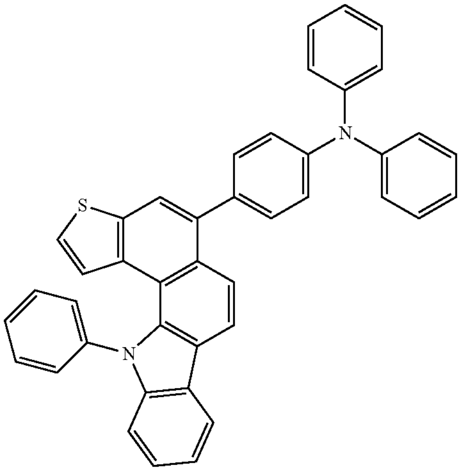

-continued
21
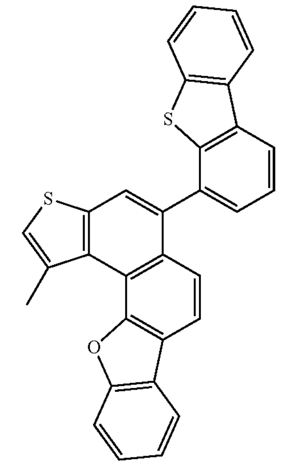
22
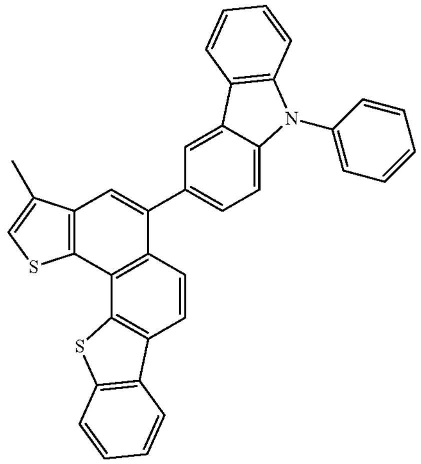
23
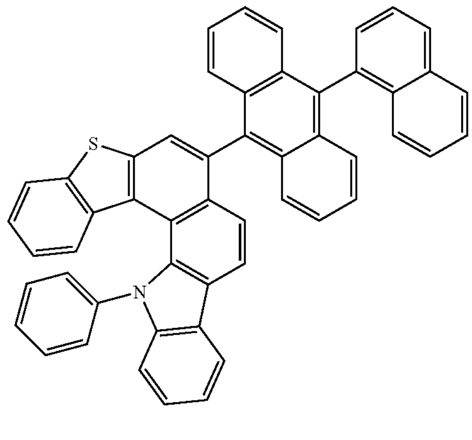
-continued
24
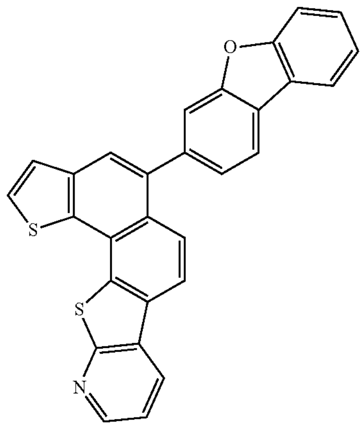
25
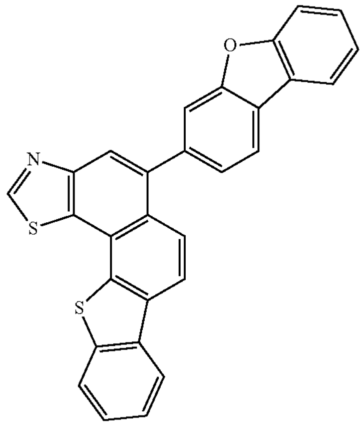
26
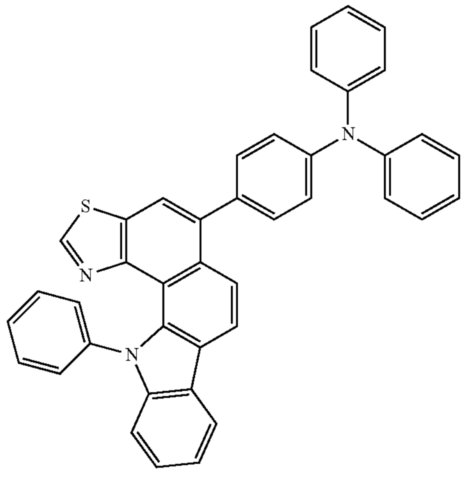

-continued
27
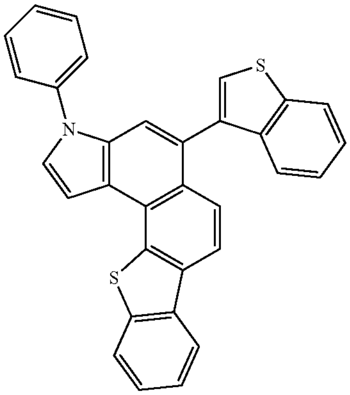
28
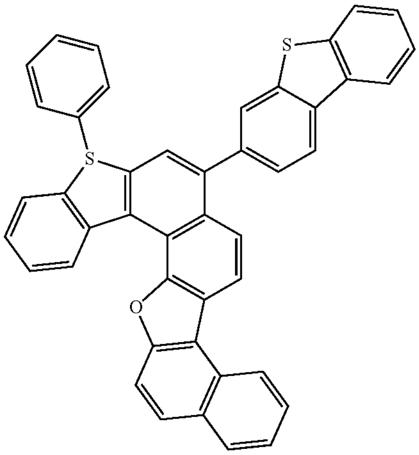
29
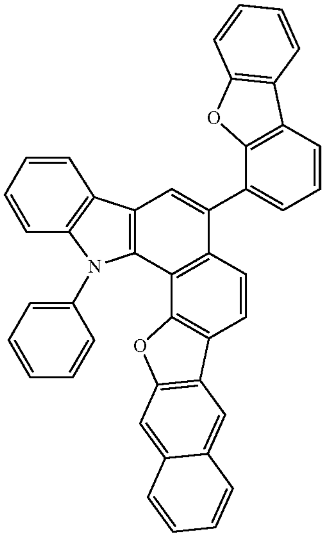
-continued
30
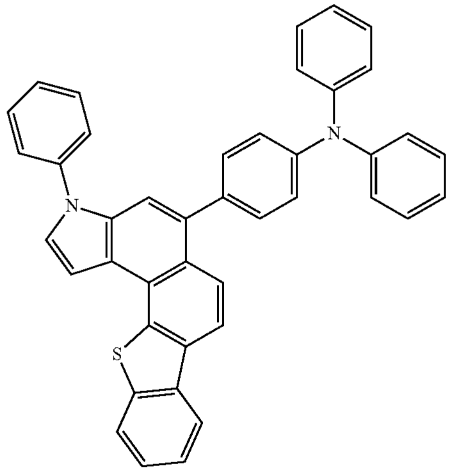
31
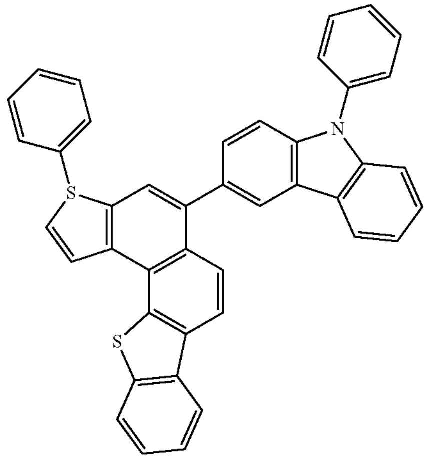
32
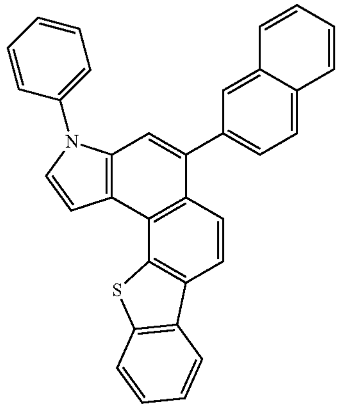

-continued
33
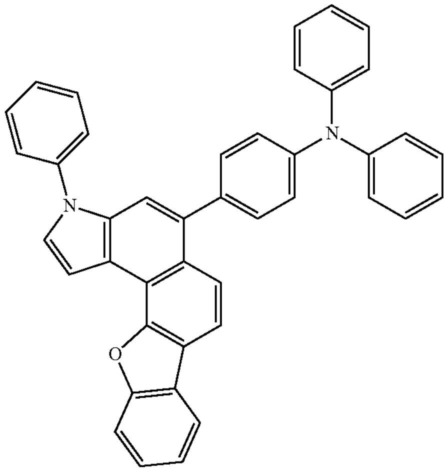
34
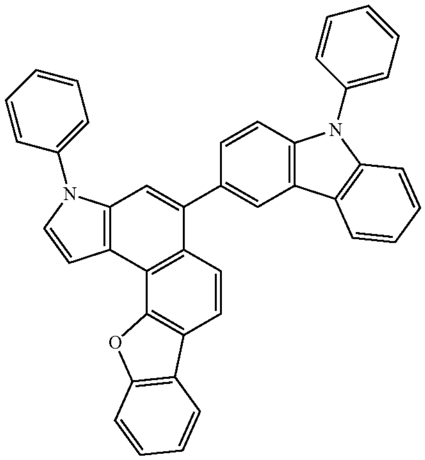
35
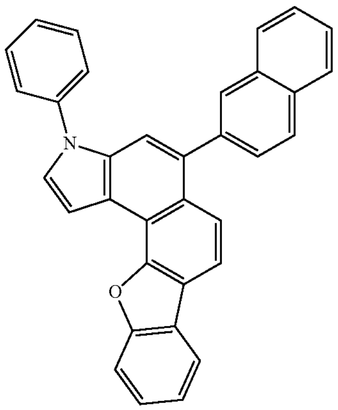
-continued
36
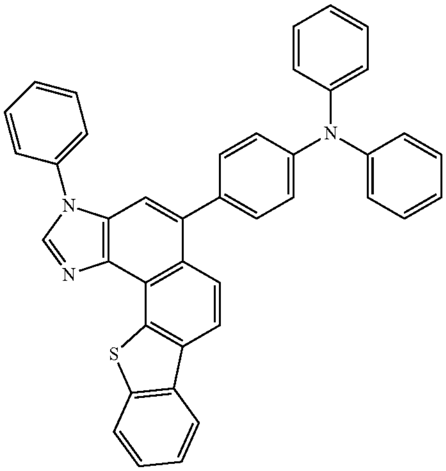
37
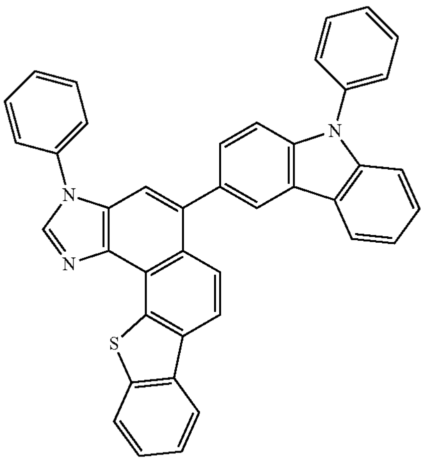
38
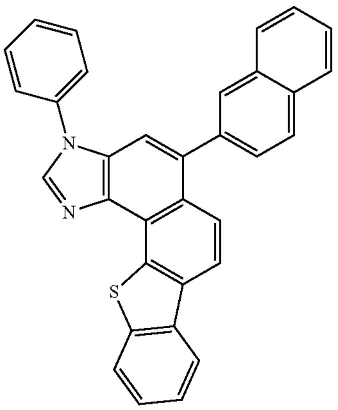

-continued
39
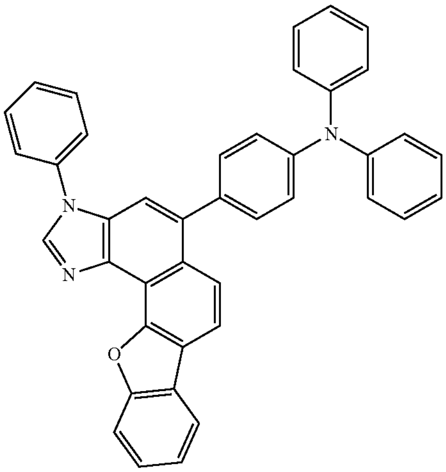
40
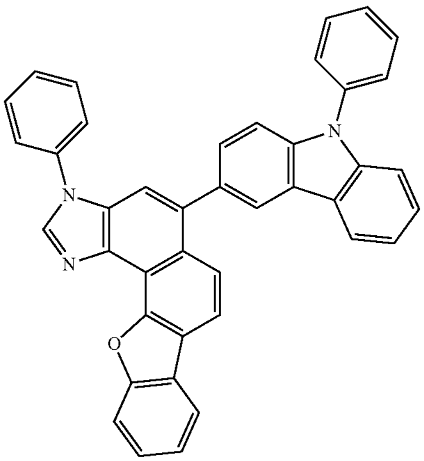
41
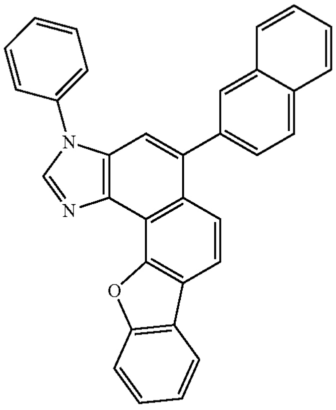
-continued
42
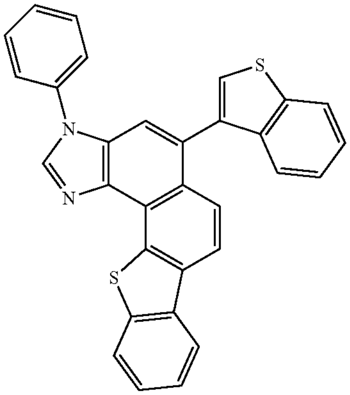
43
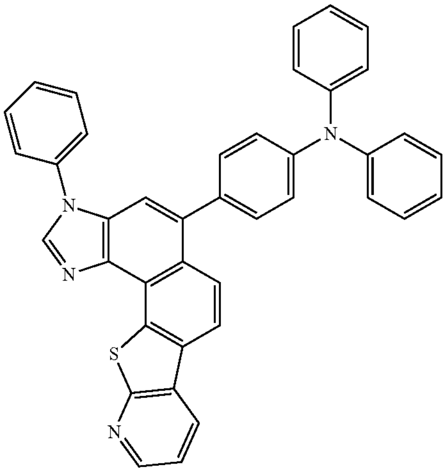
44
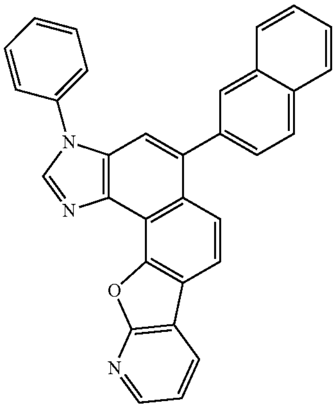

-continued
45
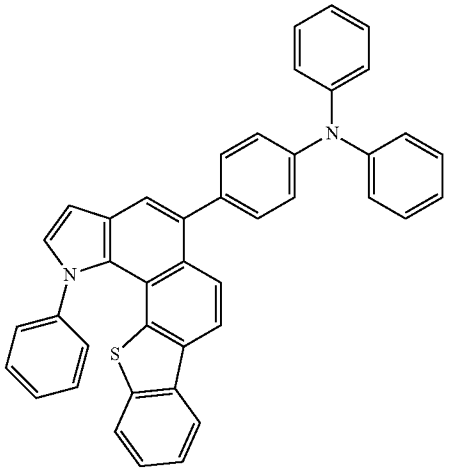
46
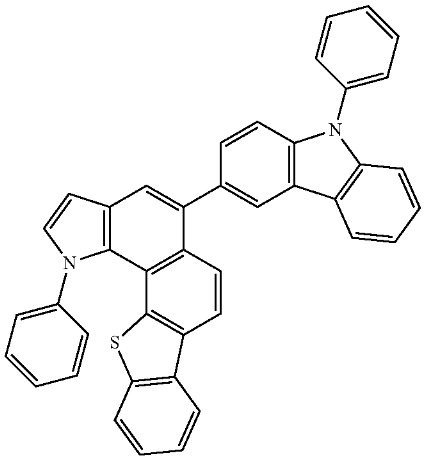
47
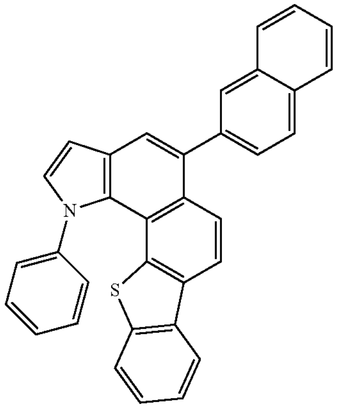
-continued
48
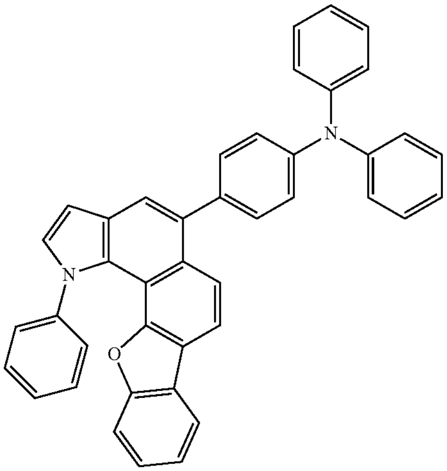
49
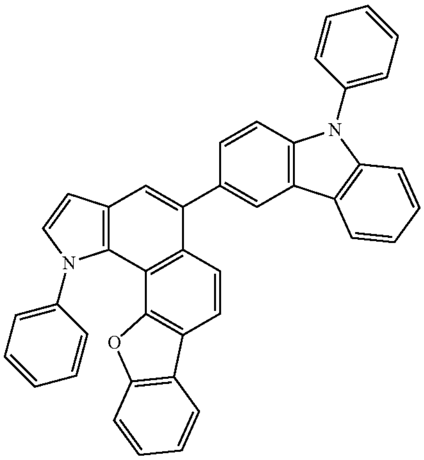
50
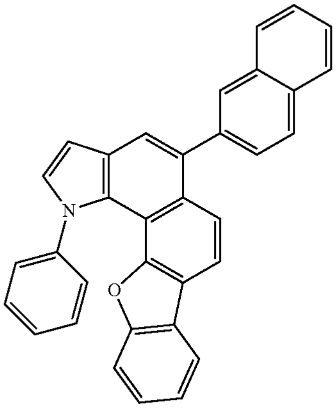

-continued

51

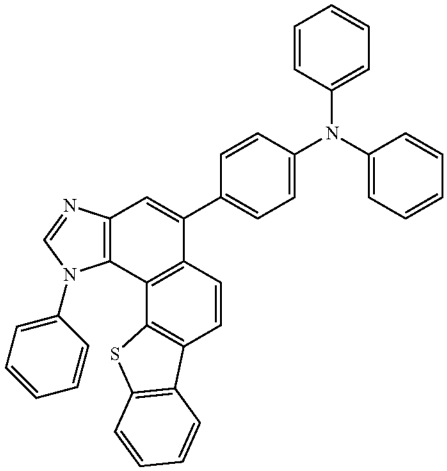

52

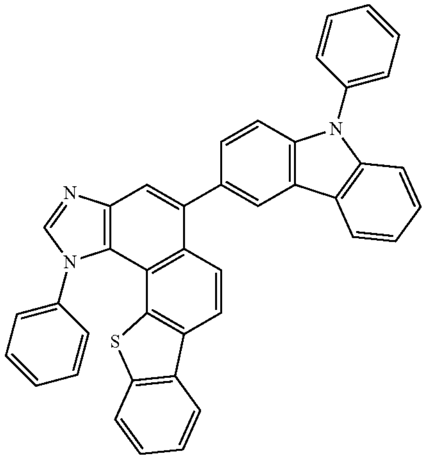

53

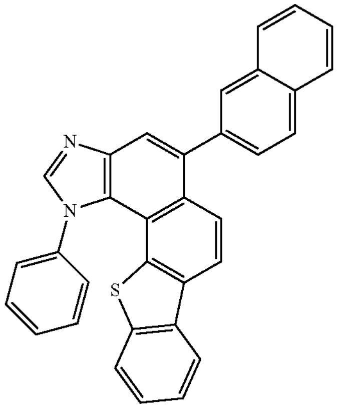

-continued

54

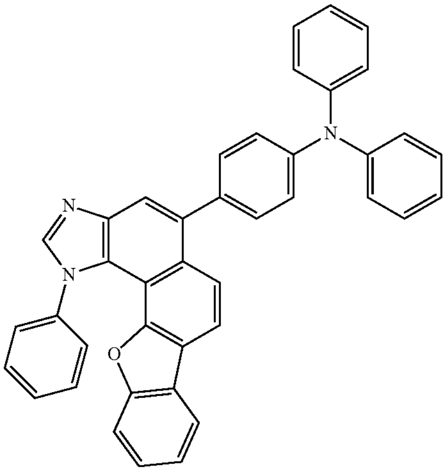

55

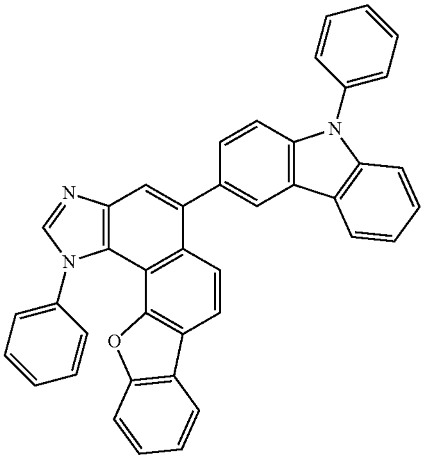

56

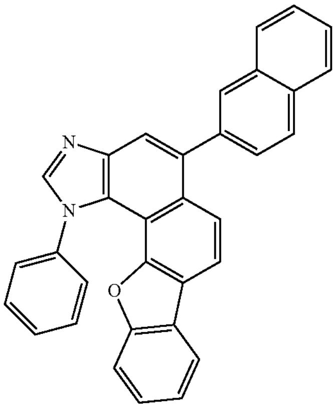

According to another aspect of the present invention, there is provided an organic light-emitting device including a first electrode, a second electrode disposed opposite to the first electrode, and an organic layer disposed between the first electrode and the second electrode, the organic layer including at least one of the above-described heterocyclic compounds.

The organic layer may include at least one of a hole injection layer, a hole transport layer, a functional layer having both hole injection and hole transport capabilities, a buffer layer, an emission layer, a hole blocking layer, an electron transport layer, an electron injection layer, and a functional layer having both electron injection and electron transport capabilities.

The organic layer may include at least one of a hole injection layer, a hole transport layer, and a functional layer having both hole injection and hole transport capabilities, at least one of the hole injection layer, the hole transport layer, and the functional layer having both hole injection and hole transport capabilities comprising the at least one heterocyclic compound.

The organic layer may include at least one of an electron injection layer, an electron transport layer, and a functional layer having both electron injection and electron transport capabilities, at least one of the electron injection layer, the electron transport layer, and the functional layer having both electron injection and electron transport capabilities comprising the at least one heterocyclic compound.

The organic layer may include an emission layer, and the emission layer may include the at least one heterocyclic compound.

The at least one heterocyclic compound may be used as a fluorescent or phosphorescent host.

The at least one heterocyclic compound may be used as a fluorescent dopant.

The organic layer may include at least one of an emission layer, an electron injection layer, an electron transport layer, and a functional layer having both electron injection and electron transport capabilities; at least one of the electron injection layer, the electron transport layer and the functional layer having both electron injection and electron transport capabilities may include the heterocyclic compound; and the emission layer may include an arylamine compound.

According to another embodiment of the present invention, there is provided an organic light-emitting display device including: a transistor including a source, a drain, a gate, and an active layer; and the above-described organic light-emitting device; one of the source and the drain of the transistor may be electrically connected to the first electrode of the organic light-emitting device.

BRIEF DESCRIPTION OF THE DRAWING

The above and other features and advantages of the present invention will be made more apparent by describing in detail exemplary embodiments thereof with reference to the attached drawing in which:

The FIGURE is a schematic cross-sectional view of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of", when preceding a list of elements, modify the entire list of elements and do not modify the individual elements of the list.

According to an embodiment of the present invention, there is provided a heterocyclic compound represented by Formula 1 below.

<Formula 1>

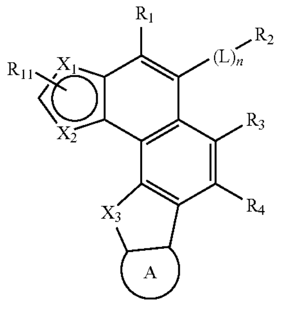

In Formula 1, the 5-membered ring with $X_1$ and $X_2$ has a resonance structure and includes at least one heteroatom. $X_1$ and $X_2$ are not both carbon atoms. That is, $X_1$ and $X_2$ are each independently one of —C($R_{12}$)—, —N—, —N($R_{13}$)—, —O—, and —S—, and at least one of $X_1$ and $X_2$ is selected from —N—, —N($R_{13}$)—, —O—, and —S—.

The 5-membered ring with $X_3$ includes a heteroatom. That is, $X_3$ is selected from —N($R_{21}$)—, —O—, and —S—.

$R_1$, $R_2$, $R_3$, $R_4$, $R_{11}$, $R_{12}$, $R_{13}$, and $R_{21}$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, and a —N($Q_1$)($Q_2$) group.

$Q_1$ and $Q_2$ are each independently one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ arylthio group, and a substituted or unsubstituted $C_2$-$C_{30}$ heteroaryl group. For example, if $Q_1$ and $Q_2$ are each independently a substituted or unsubstituted $C_6$-$C_{30}$ aryl group, the group of —N($Q_1$)($Q_2$) indicates an arylamine group;

L as a linker is selected from a substituted or unsubstituted $C_6$-$C_{30}$ arylene group and a substituted or unsubstituted $C_2$-$C_{30}$ hetero arylene group; and n indicates the number of linkers L and may be an integer from 0 to 3. If n is 0, L represents a single bond. If n is 2 or greater, a plurality of $L_1$ may be the same or different.

The ring A as a ring fused to the 5-membered ring with $X_3$ may be selected from a substituted or unsubstituted $C_6$-$C_{30}$ aromatic ring and a substituted or unsubstituted $C_2$-$C_{30}$ heteroaromatic ring.

In Formula 1, $R_{11}$ and $R_{12}$ are selectively bound together to form one of a substituted or unsubstituted $C_6$-$C_{30}$ aromatic ring and a substituted or unsubstituted $C_2$-$C_{30}$ heteroaromatic ring.

The ring formed from the bonding of $R_{11}$ to $R_{12}$ may be fused with the 5-membered ring with $X_1$ and $X_2$.
The heterocyclic compound may be represented by one of Compounds 2a to 2t below, depending on each $X_1$, $X_2$ and $X_3$ chosen.
<Formula 2a>
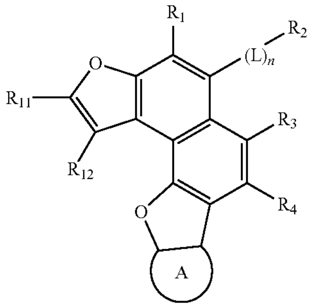
<Formula 2b>
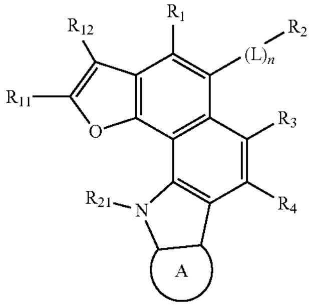
<Formula 2c>
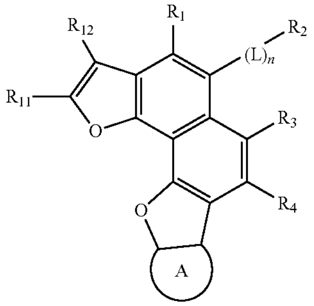
<Formula 2d>
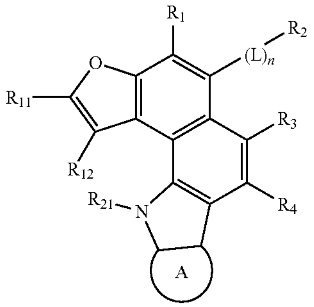
-continued
<Formula 2e>
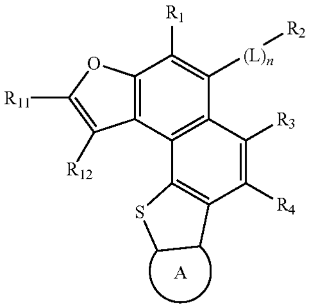
<Formula 2f>
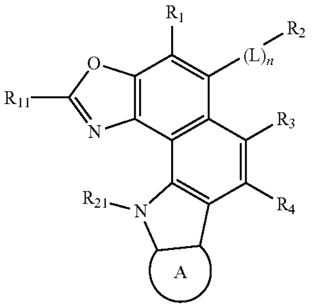
<Formula 2g>
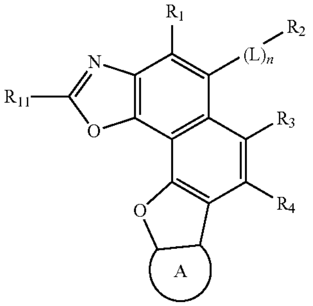
<Formula 2h>
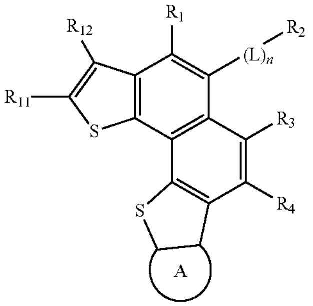
<Formula 2i>
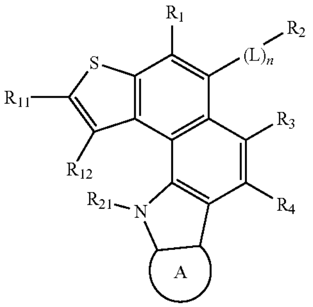

-continued
<Formula 2j>
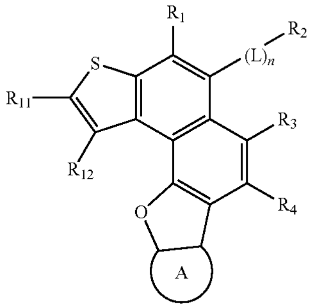
<Formula 2k>
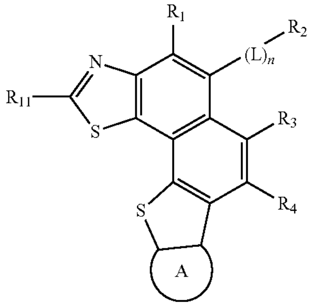
<Formula 2l>
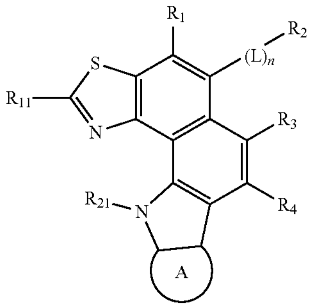
<Formula 2m>
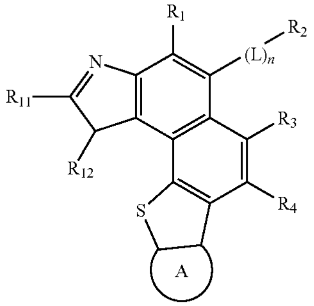
<Formula 2n>
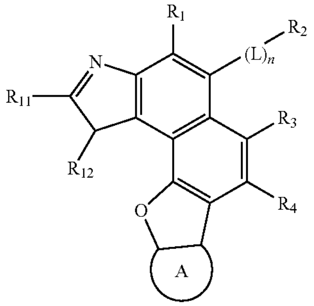
-continued
<Formula 2o>
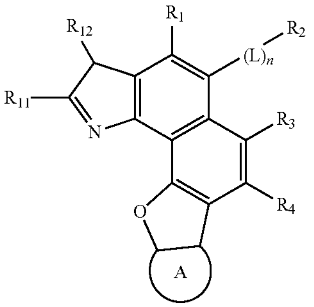
<Formula 2p>
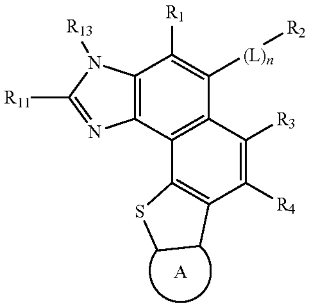
<Formula 2q>
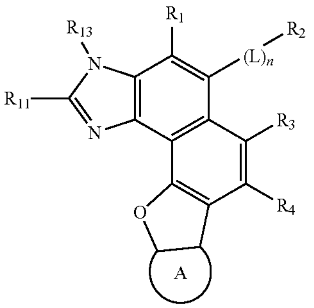
<Formula 2r>
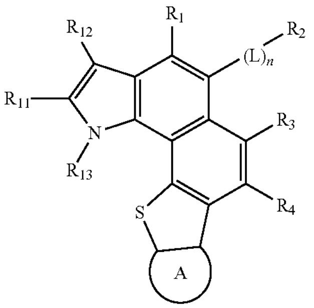
<Formula 2s>
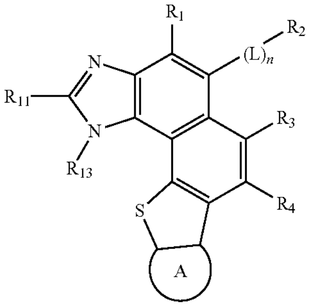

-continued

<Formula 2t>

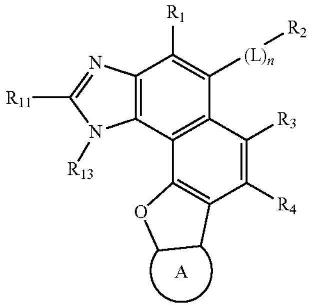

In Formulae 2a to 2t above, $R_1$, $R_2$, $R_3$, $R_4$, $R_{11}$, $R_{12}$, $R_{13}$, $R_{21}$, L, n, and ring A are as defined in Formula 1.

In Formula 1, ring A may be one of a substituted or unsubstituted benzene ring, a substituted or unsubstituted naphthalene ring, a substituted or unsubstituted anthracene ring, a substituted or unsubstituted phenanthrene ring, and a substituted or unsubstituted pyridine ring.

The ring A may be represented by one of the Formulae 3a to 3e below.

<Formula 3a>

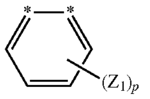

<Formula 3b>

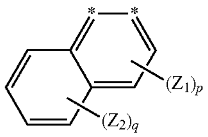

<Formula 3c>

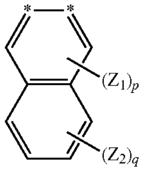

<Formula 3d>

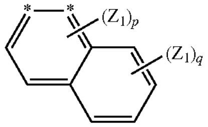

<Formula 3e>

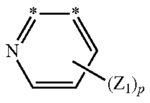

In Formulae 3a to 3e, $Z_1$ and $Z_2$ may be each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, and a substituted or unsubstituted biphenyl group; and p and q may be each independently an integer from 2 to 4.

The asterisk (*) indicates a binding site of the ring A with the rest of the heterocyclic compound, and a pair of asterisks indicates a site where two carbon atoms are fused with the rest of the heterocyclic compound.

The ring A may be represented by one of the Formulae 4a to 4e below.

<Formula 4a>

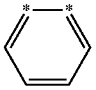

<Formula 4b>

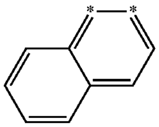

<Formula 4c>

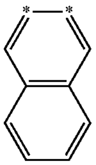

<Formula 4d>

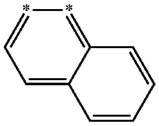

<Formula 4e>

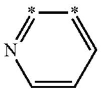

In Formulae 4a to 4e, an asterisk (*) indicates a binding site of the ring A with the rest of the heterocyclic compound, and a pair of asterisks indicates a site where two carbon atoms are fused with the rest of the heterocyclic compound.

In Formula 1 above, $R_{11}$ and $R_{12}$ are selectively bound together to form a substituted or unsubstituted benzene ring, which may be fused with the 5-membered ring comprising $X_1$ and $X_2$.

In Formula 1, $R_1$, $R_2$, $R_3$, $R_4$, $R_{11}$, $R_{12}$, $R_{13}$, and $R_{21}$ may be each independently one of a hydrogen atom, a deuterium atom, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted naphthacenyl group, a substituted or unsubstituted fluorenyl group, a substituted or unsubstituted pyridinyl, substituted or unsubstituted bipyridinyl group, a substituted or unsubstituted pyrazinyl group, a substituted or unsubstituted pyrimidinyl group, a substituted or unsubstituted pyridazinyl group, a substituted or unsubstituted quinolinyl group, a substituted or unsubstituted isoquinolinyl group, a substituted or unsubstituted carbazolyl group, a substituted or unsubstituted benzothiophenyl group, a substituted or unsubstituted dibenzothiophenyl group, a substituted or unsubstituted benzofuranyl group, a substituted or unsubstituted dibenzofuranyl group, and a group represented by $—N(Q_3)(Q_4)$, $—N(Q_3)(Q_4)$ indicating an arylamine group; and $Q_3$ and $Q_4$ are each independently one of a substituted or unsubstituted phenyl group, a substituted or unsubstituted biphenyl group, and a substituted or unsubstituted naphthyl group.

In Formula 1, $R_2$ may be represented by one of the groups represented by Formulae 5a to 5i.

<Formula 5a>

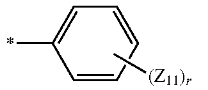

<Formula 5b>

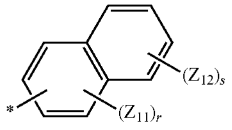

<Formula 5c>

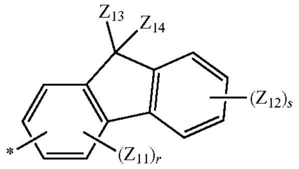

<Formula 5d>

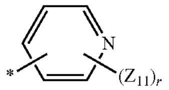

<Formula 5e>

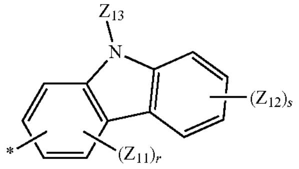

<Formula 5f>

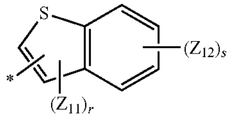

<Formula 5g>

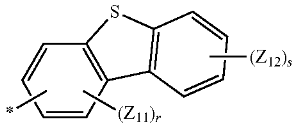

<Formula 5h>

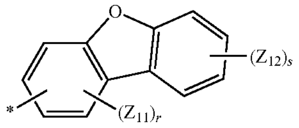

<Formula 5i>

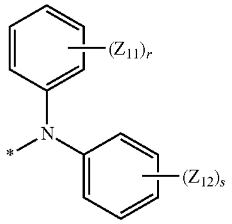

In Formulae 5a to 5i above, $Z_{11}$ and $Z_{14}$ may be each independently one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted propoxy group, a substituted or unsubstituted butoxy group, a substituted or unsubstituted phenyl group, and a substituted or unsubstituted biphenyl group; and r and s may be each independently an integer from 1 to 5, and an asterisk (*) indicates a binding site of $R_2$ with the rest of the heterocyclic compound.

For example, $R_2$ may be represented by one of the Formulae 6a to 6i below.

<Formula 6a>

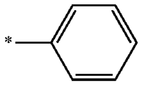

<Formula 6b>

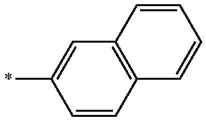

<Formula 6c>

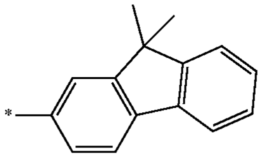

<Formula 6d>

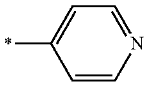

<Formula 6e>

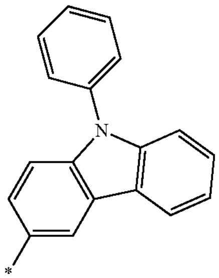

<Formula 6f>

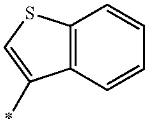

<Formula 6g>

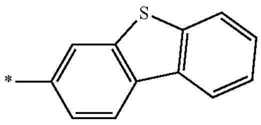

<Formula 6h>

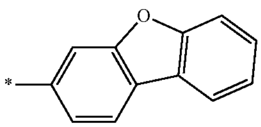

-continued

<Formula 6i>

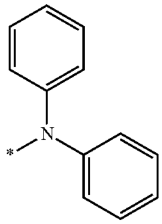

In Formulae 6a to 6i, an asterisk (*) indicates a binding site of $R_2$ with the rest of the heterocyclic compound.

In Formula 1, if n is 0, the linker L may be a single bond. If n is 1, the linker n is a phenylene group, a naphthylene group, or an anthracenylene group.

The heterocyclic compound of Formula 1 may be one of Compounds 1 to 56 below, but is not limited thereto.

1

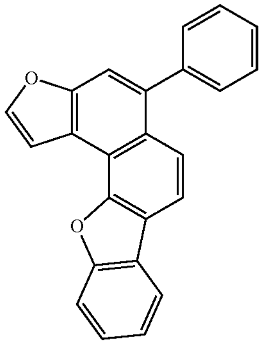

2

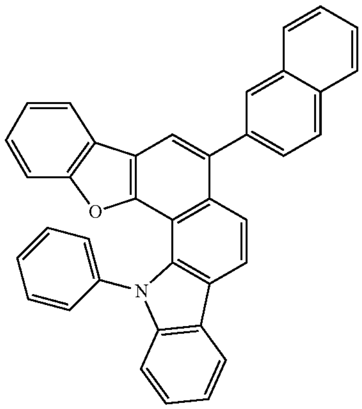

3

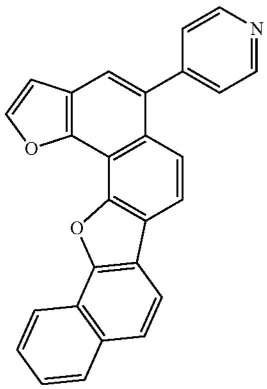

-continued

4

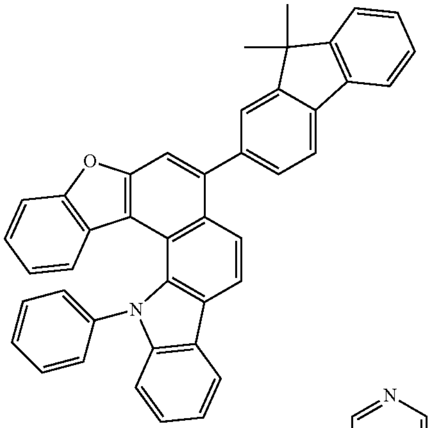

5

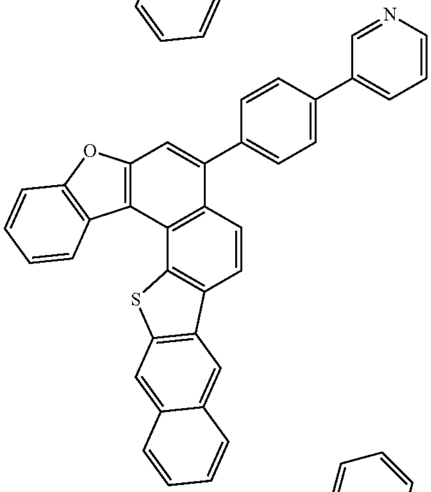

6

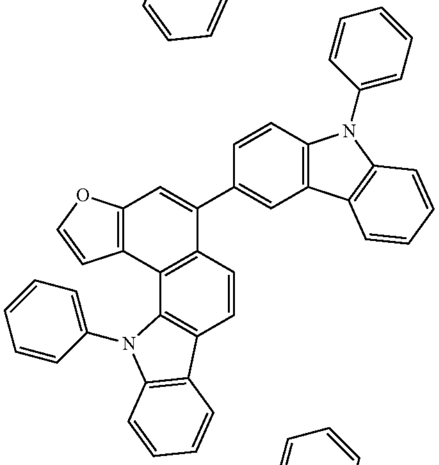

7

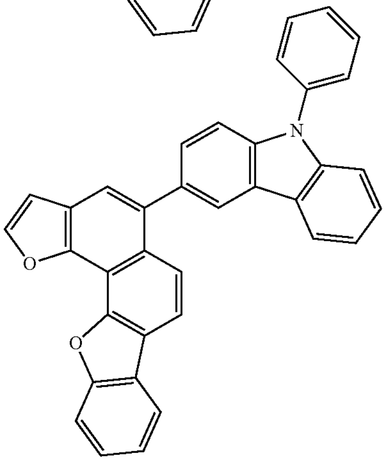

-continued
8
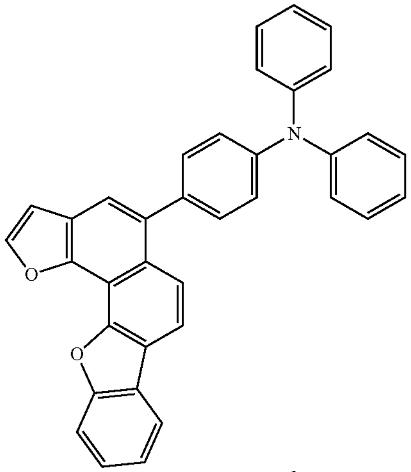
9
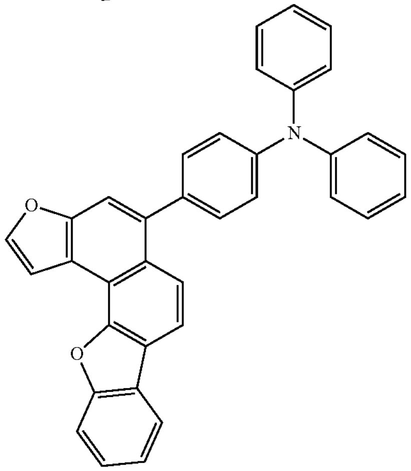
10
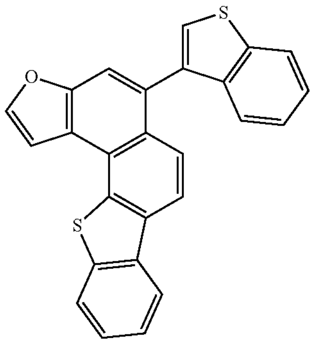
11
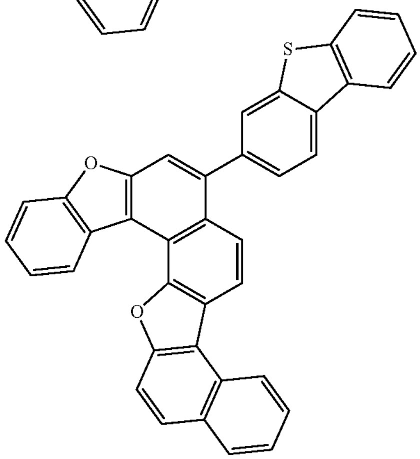
-continued
12
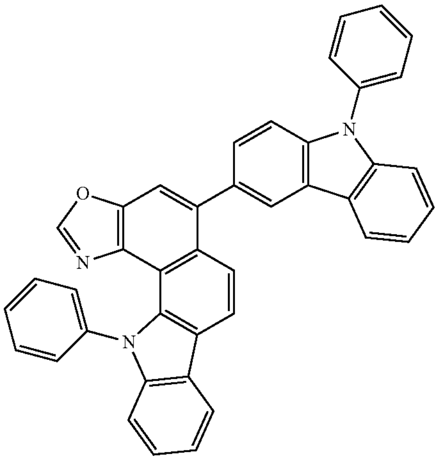
13
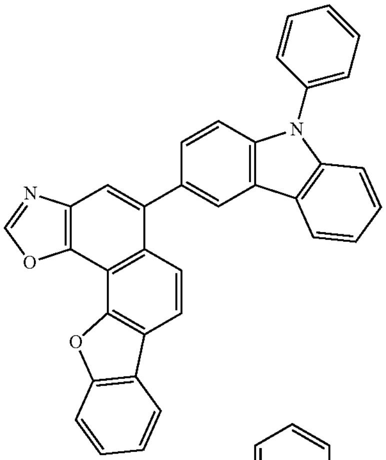
14
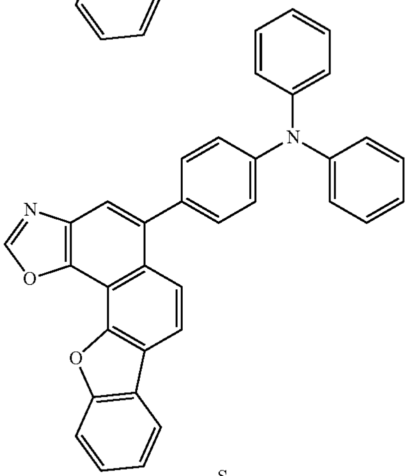
15
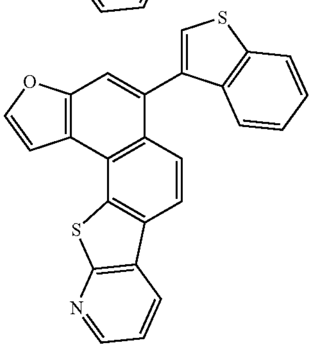

-continued
16
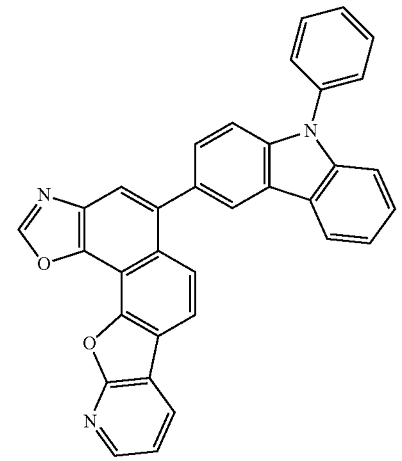
17
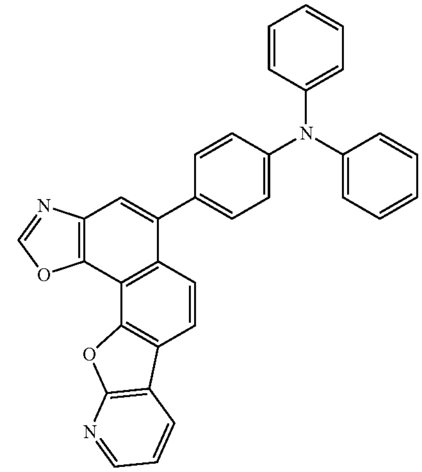
18
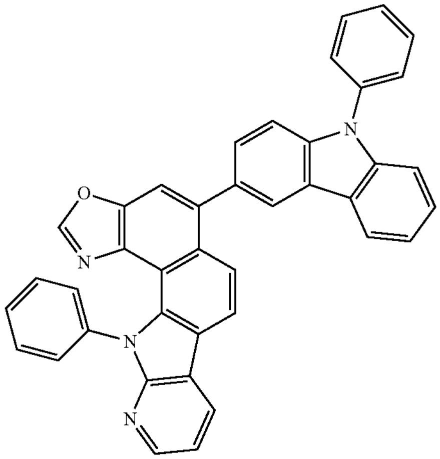
-continued
19
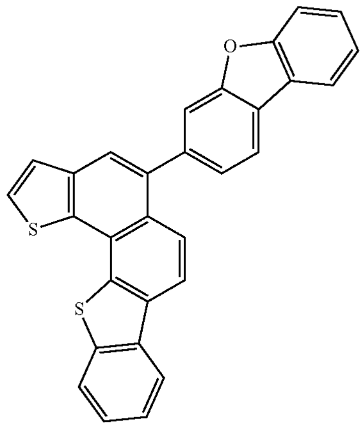
20
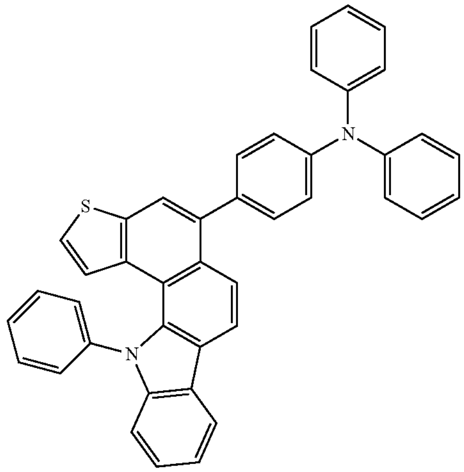
21
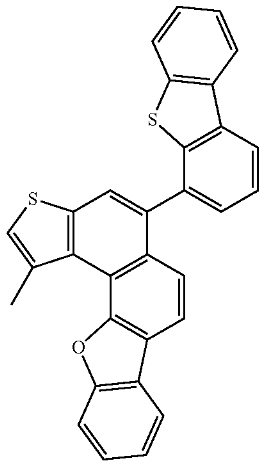

-continued
22
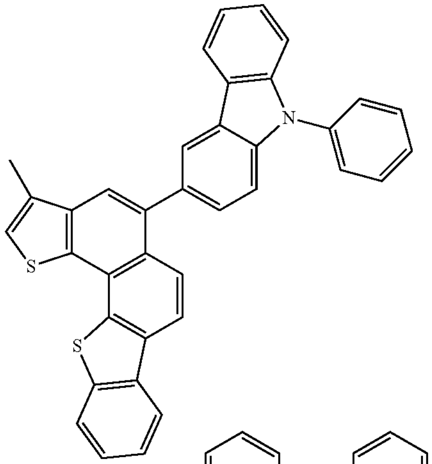
23
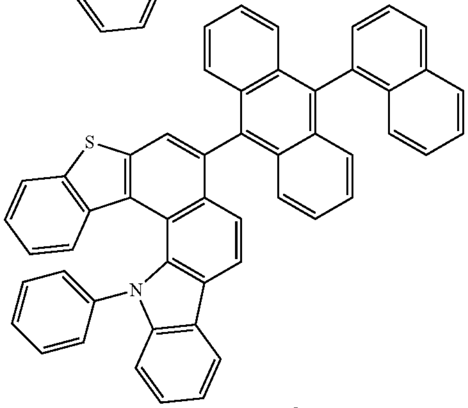
24
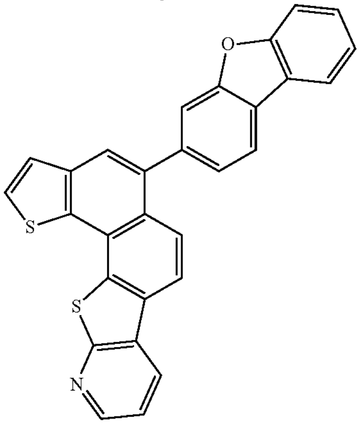
25
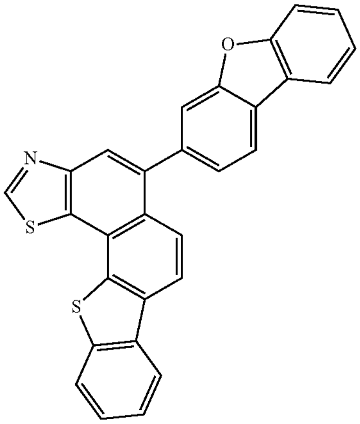
-continued
26
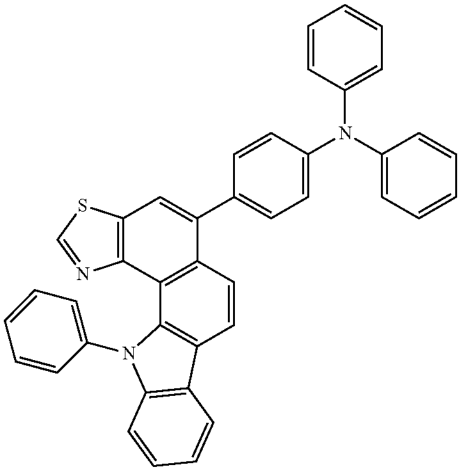
27
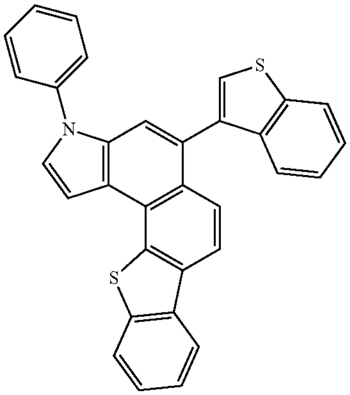
28
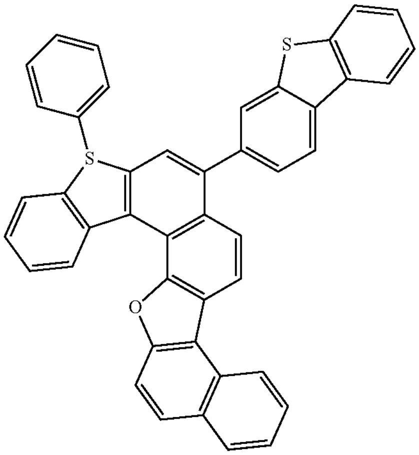

-continued
29
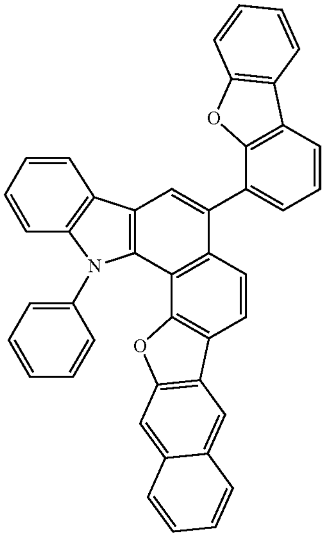
30
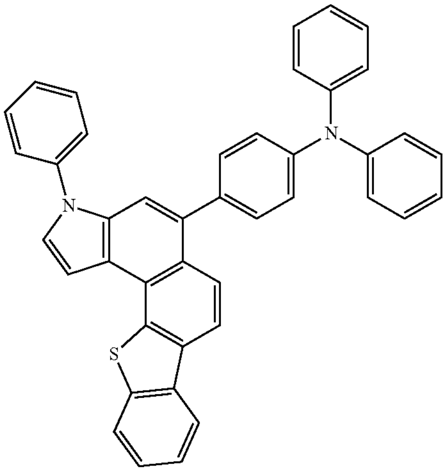
31
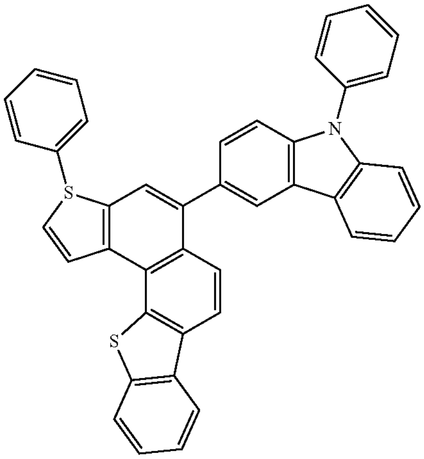
-continued
32
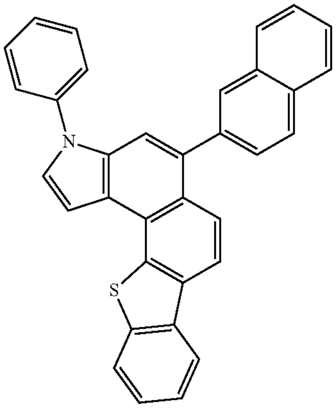
33
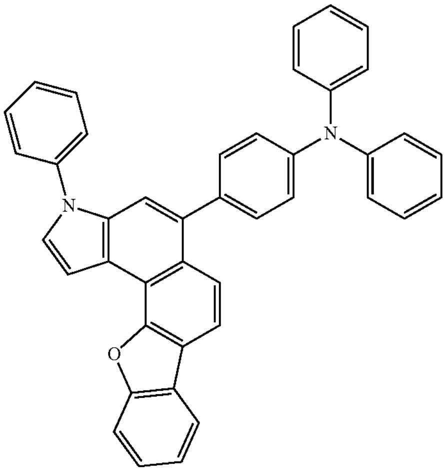
34
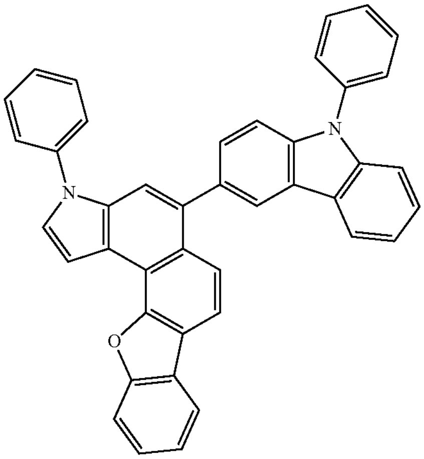

-continued
35
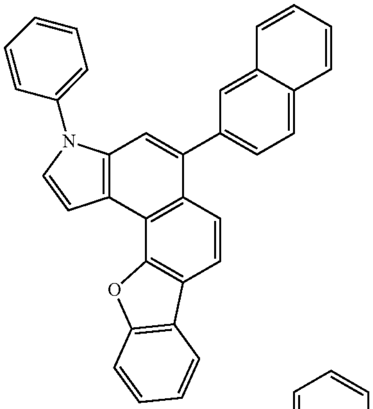
36
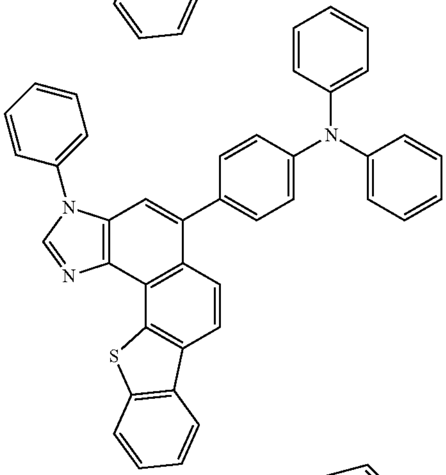
37
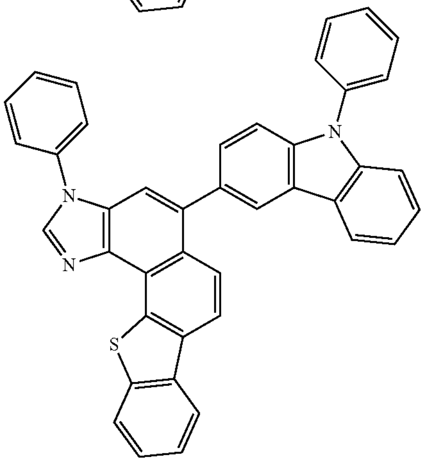
38
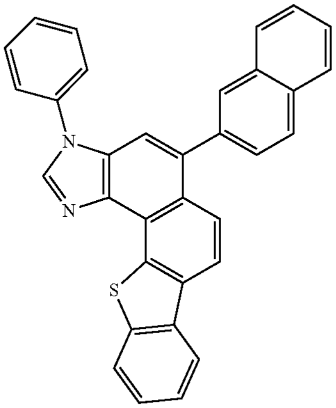
-continued
39
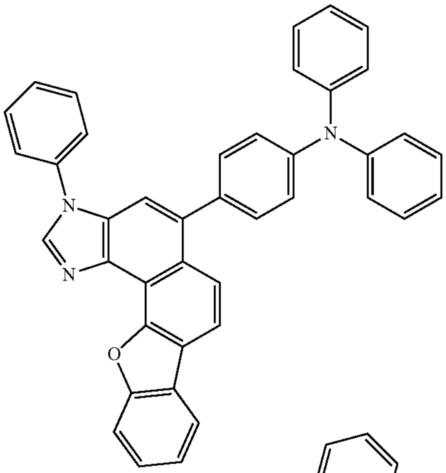
40
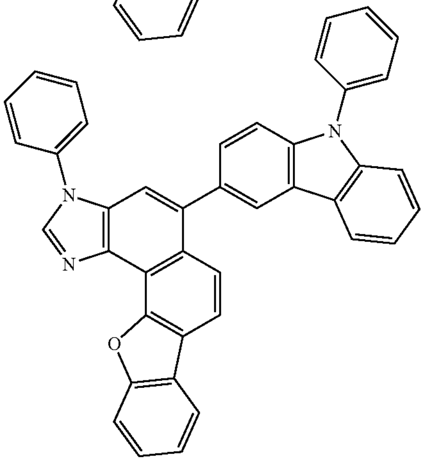
41
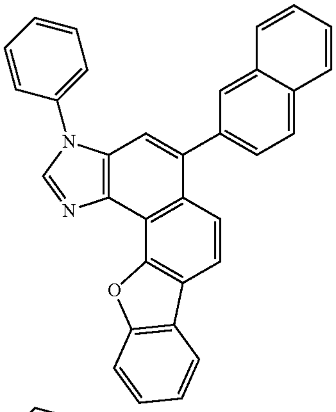
42
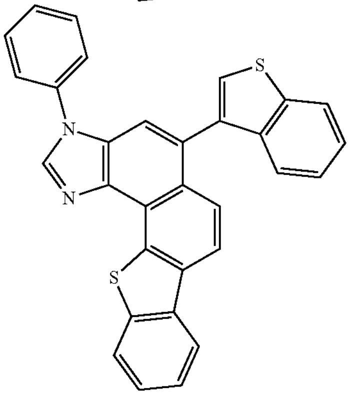

-continued
43
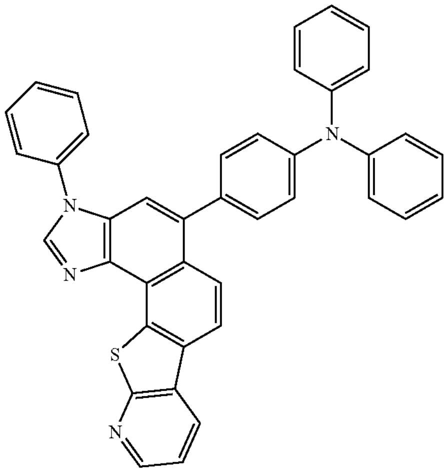
44
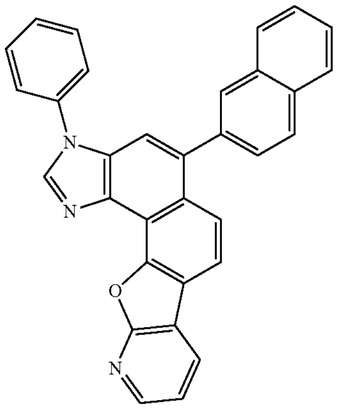
45
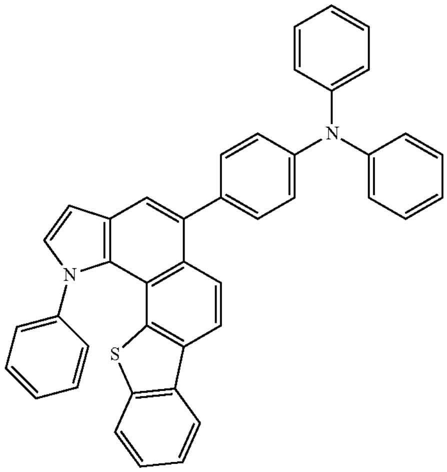
-continued
46
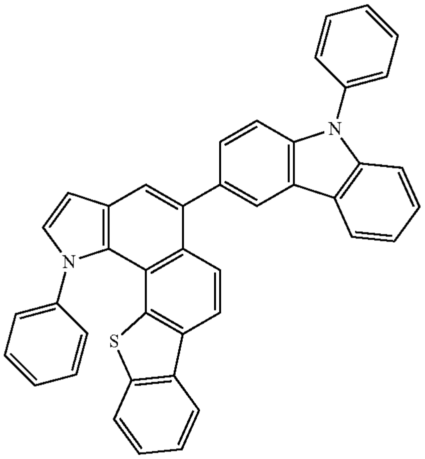
47
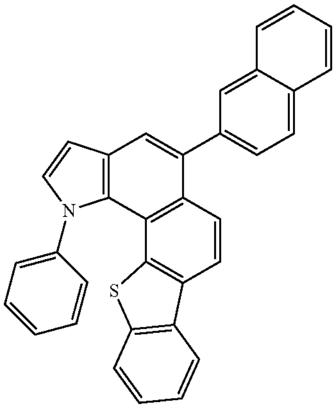
48
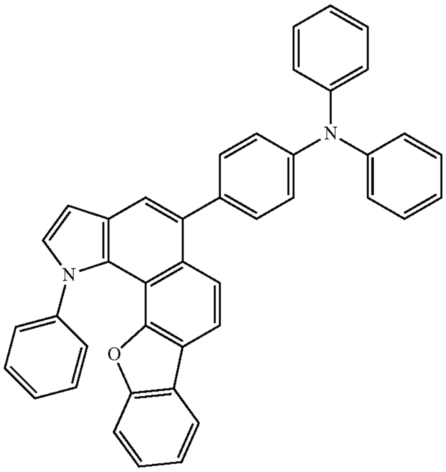

49
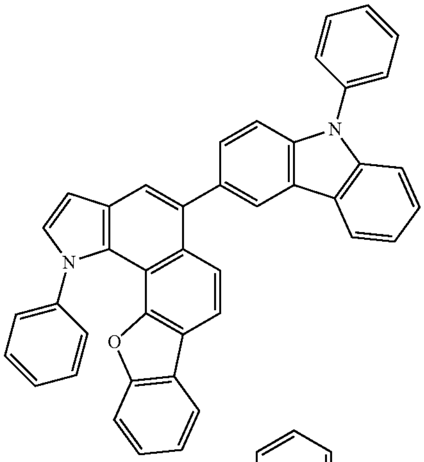
50
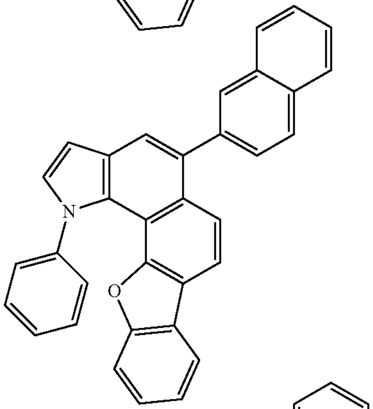
51
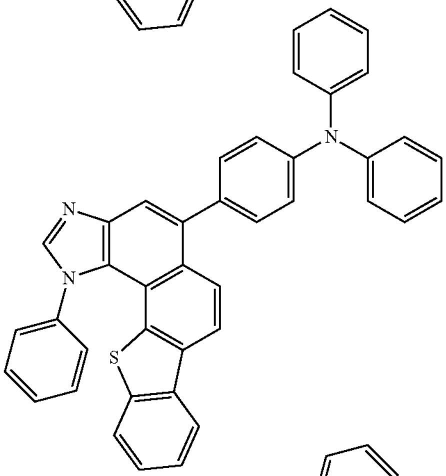
52
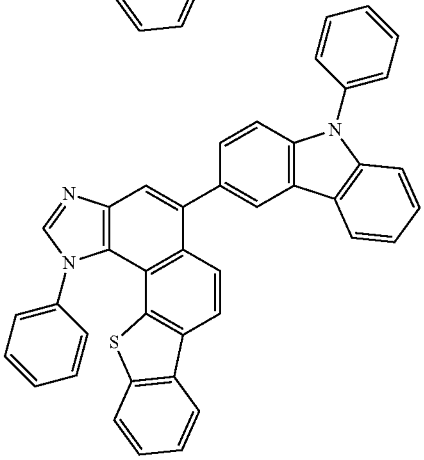
53
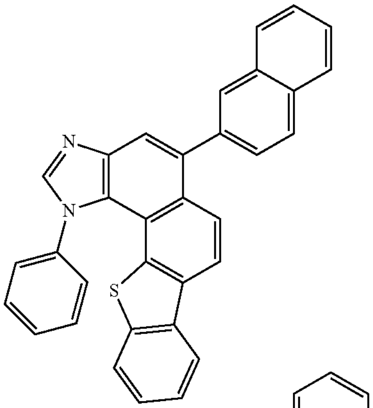
54
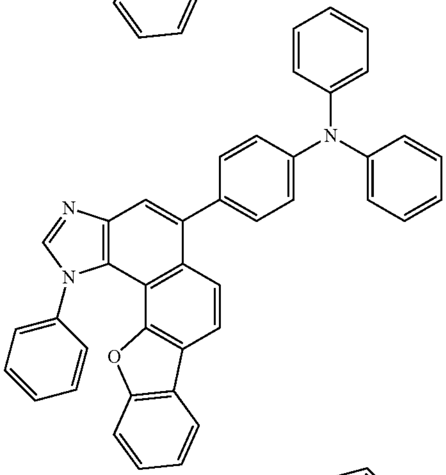
55
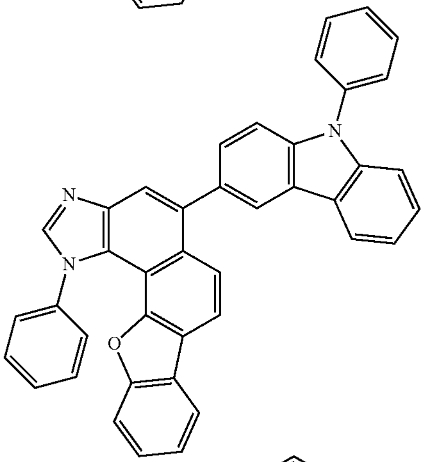
56
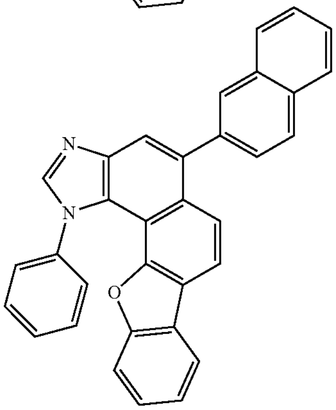

The heterocyclic compound of Formula 1 may be represented by resonance structures of the 5-membered ring with a heteroatom and of derivative structures having an aromatic ring or a heteroaromatic ring fused with a carbazole, dibenzothiophene, or dibenzofurane derivative, the said derivative structures featuring rigid backbone structures with high glass transition temperatures and high melting points.

The heterocyclic compounds of Formula 1 may exhibit high electrical stability, improved charge transport ability and light-emitting properties when used in organic light-emitting devices.

An organic light-emitting device including a heterocyclic compound structured according to Formula 1 may have high heat resistance against the Joule heat that may be generated between organic layers, in an organic layer, and/or between an EML and a metal electrode when the device is stored and/or operated.

The heterocyclic compound of Formula 1 may be synthesized using known organic synthesis methods. A synthesis method of the heterocyclic compound of Formula 1 may be understood by those of ordinary skill in the art from the examples that will be described below.

The heterocyclic compound of Formula 1 may be used between a pair of electrodes of an organic light-emitting device. For example, the heterocyclic compound of Formula 1 may be used in an emission layer, or in a layer between a cathode and the emission layer (for example, in an electron injection layer, an electron transport layer, or a functional layer having both electron injection and electron transport capabilities).

Hereinafter, an organic light-emitting device 10 according to an embodiment of the present invention will now be described with reference to the FIGURE but is not limited to the structure illustrated in the FIGURE.

Referring to the FIGURE, the organic light-emitting device 10 includes a substrate 11, a first electrode 13 disposed on the substrate 11, a second electrode 19 disposed opposite to the first electrode 13, and an organic layer 15 disposed between the first electrode 13 and the second electrode 19. The organic layer 15 includes a heterocyclic compound according to Formula 1.

The term "organic layer" as used herein refers to a single layer and/or a plurality of layers disposed between the first and second electrodes of the organic light-emitting device.

As used herein, "(for example, the organic layer) including the heterocyclic compound of Formula 1" means "(the organic layer) including one or at least two different heterocyclic compounds represented by Formula 1 above."

The heterocyclic compound of Formula 1 may have high heat resistance against the Joule heat that may be generated between the multiple layers constituting the organic layer 15, in the organic layer 15, and/or between an emission layer and a metal electrode when the organic light-emitting device 10 is stored or is operated. Therefore, the organic light-emitting device 10 including the heterocyclic compound of Formula 1 may consistently have thermal stability in high-temperature environments with time, and thus high durability and long lifetime.

The organic layer 15 may include at least one of a hole injection layer, a hole transport layer, a functional layer having both hole injection and hole transport capabilities, a buffer layer, an emission layer 16, a hole blocking layer, an electron transport layer, an electron injection layer, and a functional layer having both electron injection and electron transport capabilities. In this regard, a heterocyclic compound according to Formula 1 may be included in at least one of the hole injection layer, the hole transport layer, the functional layer having both hole injection and hole transport capabilities, the buffer layer, the emission layer 16, the hole blocking layer, the electron transport layer, the electron injection layer, and the functional layer having both electron injection and electron transport capabilities.

The organic layer 15 may include at least one of a hole injection layer, a hole transport layer, and a functional layer having both hole injection and hole transport capabilities between the emission layer 16 and the first electrode 13, wherein at least one of the hole injection layer, the hole transport layer, and the functional layer having both hole injection and hole transport capabilities may include a heterocyclic compound according to Formula 1.

At least one of the hole injection layer, the hole transport layer, and the functional layer having both hole injection and hole transport capabilities may further include a charge-generating material, which may be at least one of a quinine derivative, a metal oxide, and a cyano group-containing compound. Examples of the metal oxide are molybdenum oxides and vanadium oxides. Charge-generating materials with strong electron accepting properties may facilitate injection and transport of holes.

The organic layer 15 may include at least one of an electron injection layer, an electron transport layer, and a functional layer having both electron injection and electron transport capabilities between the emission layer 16 and the second electrode 19, wherein at least one of the electron injection layer, the electron transport layer, and the functional layer having both electron injection and electron transport capabilities may include a heterocyclic compound according to Formula 1.

The organic layer 15 may include the emission layer 16, wherein the emission layer 16 may include a heterocyclic compound according to Formula 1.

A heterocyclic compound according to Formula 1 in the emission layer 16 may serve as a fluorescent or phosphorescent host emitting red, green, or blue light and, in some embodiments, may be effectively used as a blue fluorescent host. In some embodiments, a heterocyclic compound according to Formula 1 in the emission layer 16 may serve as a fluorescent dopant.

The organic layer 15 may include the emission layer 16, and at least one of an electron injection layer, an electron transport layer, and a functional layer having both electron injection and electron transport capabilities, and the emission layer 16 and the at least one of the electron injection layer, the electron transport layer, and the functional layer having both electron injection and electron transport capabilities may include the heterocyclic compound of Formula 1 above. The emission layer 16 may include an arylamine compound.

Hereinafter, a method of manufacturing the organic light-emitting device 10 according to an embodiment of the present invention will be described with reference to the FIGURE.

The substrate 11, which may be any substrate that is used in general organic light-emitting devices, may be a glass substrate or a transparent plastic substrate with excellent mechanical strength, thermal stability, transparency, surface smoothness, ease of handling, and water resistance.

The first electrode 13 may be formed by depositing or sputtering a first electrode-forming material on the substrate 11.

When the first electrode 13 constitutes an anode, a material having a high work function may be used as the first electrode-forming material to facilitate hole injection.

The first electrode 13 may be a reflective electrode or a transmission electrode.

A transparent material with high conductivity, such as indium tin oxide (ITO), indium zinc oxide (IZO), $SnO_2$, and ZnO, may be used as the first electrode-forming material.

In some embodiments, the first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers.

For example, the first electrode 13 may have a three-layered structure of ITO:Ag:ITO, but is not limited thereto.

The organic layer 15 may be disposed on the first electrode 13. The organic layer 15 may include a hole injection layer (HIL, not shown), a hole transport layer (HTL, not shown), a buffer layer (not shown), an emission layer (EML) 16, an electron transport layer (ETL, not shown), and an electron injection layer (EIL, not shown).

The HIL may be formed on the first electrode 13 using any of a variety of methods, such as vacuum deposition, spin coating, casting, Langmuir-Blodgett (LB) deposition, or the like.

When the HIL is formed using vacuum deposition, vacuum deposition conditions may vary according to the compound that is used to form the HIL and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any material that is commonly used to form an HIL. Non-limiting examples of the material that may be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), 4,4'4"-tris(N,N-diphenylamino)triphenylamine (TDATA), 4,4',4"-tris(N-(2-naphthyl)-N-phenyl-amino)-triphenyl-amine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The thickness of the HIL may be from about 100 Å to about 10000 Å, and in some embodiments, may be from about 100 Å to about 1000 Å. When the thickness of the HIL is within these ranges, the HIL may have good hole injecting ability without causing a substantial increase in driving voltage.

Then, an HTL may be formed on the HIL by using vacuum deposition, spin coating, casting, Langmuir-Blodgett (LB) deposition, or the like.

When the HTL is formed using vacuum deposition or spin coating, the conditions for deposition and coating may be similar to those for the formation of the HIL, although the conditions for the deposition and coating may vary according to the material that is used to form the HTL.

Non-limiting examples of suitable known HTL forming materials are carbazole derivatives, such as N-phenylcarbazole or polyvinylcarbazole, N,N-bis(3-methylphenyl)-N,N-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

The thickness of the HTL may be from about 50 Å to about 2000 Å, and, in some embodiments, may be from about 100 Å to about 1500 Å. When the thickness of the HTL is within these ranges, the HTL may have good hole transporting ability without a substantial increase in driving voltage.

The functional layer having both hole injection and hole transport capabilities may include at least one of an HIL-forming material and an HTL-forming material. The functional layer having both hole injection and hole transport capabilities may have a thickness of from about 500 Å to about 10,000 Å, and in some embodiments, may have a thickness of from about 100 Å to about 1,000 Å. When the thickness of the functional layer having both hole injection and hole transport capabilities is within these ranges, the functional layer may have good hole injection and transport capabilities without a substantial increase in driving voltage.

At least one of the HIL, the HTL, and the functional layer having both hole injection and hole transport capabilities may further include, in addition to a known HIL-forming material, a charge-generating material described above.

A buffer layer may be disposed between at least one of the HIL, HTL, and functional layer having both hole injection and transport capabilities, and the EML 16. The buffer layer may correspond to the establishment of an optical resonance distance of light according to a wavelength of light emitted from the EML 16 and thus may increase efficiency. The buffer layer may include any HIL-forming material and an HTL-forming material.

Then, the EML 16 may be formed on the HTL, the functional layer having both hole injection and transport capabilities, and the buffer layer may be formed adjacent to the EML 16. Both may be formed by vacuum deposition, spin coating, casting, Langmuir-Blodget (LB) deposition, or the like. When the EML 16 is formed using vacuum deposition or spin coating, the deposition and coating conditions may be similar to those for the formation of the HIL, though the conditions for deposition and coating may vary according to the material that is used to form the EML 16.

The EML 16 may include a heterocyclic compound according to Formula 1 as a host material. In some embodiments, the EML 16 may further include a known host in addition to a heterocyclic compound according to Formula 1. Non-limiting examples of the host are tris(8-hydroxyquinolinato)aluminum (Alq3), 4,4'-Bis(9-carbazolyl)-1,1'-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), 9,9,9',9',9",9"-Hexaethyl-9H,9'H,9"H-[2,2':7',2"]terfluorene (E3)

E3

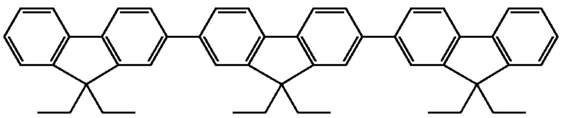

, distyrylarylene (DSA), and 4,4'-bis(9-carbazolyl)-2,2'-dimethylbiphenyl (dmCBP).

When the organic light-emitting device 10 includes at least one of a red EML, a green EML, and a blue EML, the EML 16 may include a heterocyclic compound according to Formula 1. In some embodiments, the EML 16 may further include a known dopant, in addition to the heterocyclic compound of Formula 1 above. Non-limiting examples of available known dopants are as follows ("ppy" is the abbreviation for phenylpyridine).

Non-limiting examples of blue dopants are compounds represented by the following Formulae.

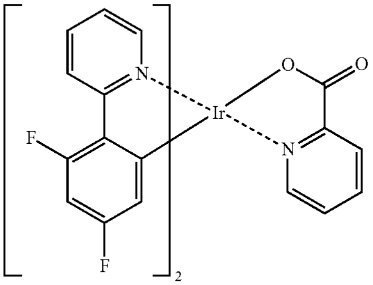

$F_2Irpic$

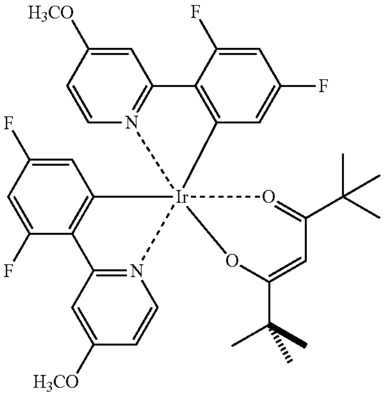

(F2ppy)2Ir(tmd)

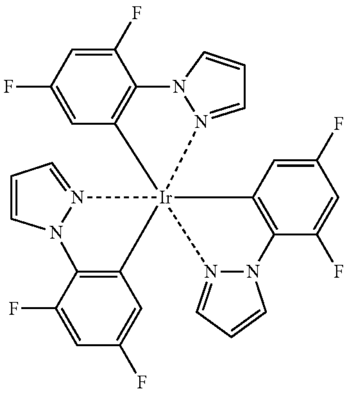

$Ir(dfppz)_3$

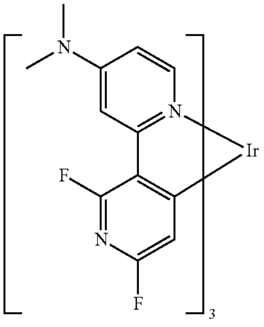

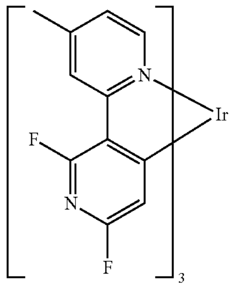

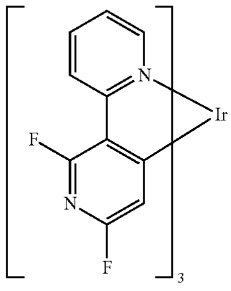

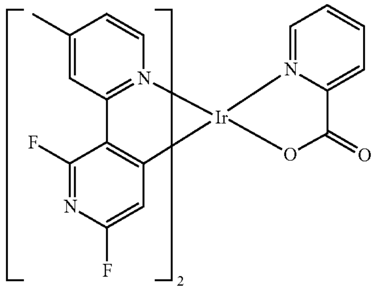

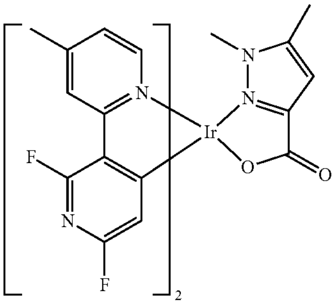

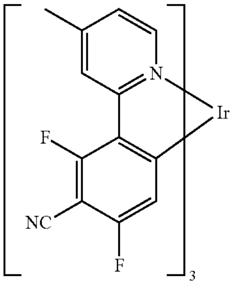

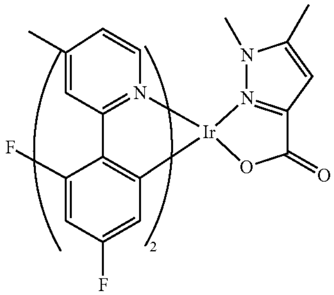

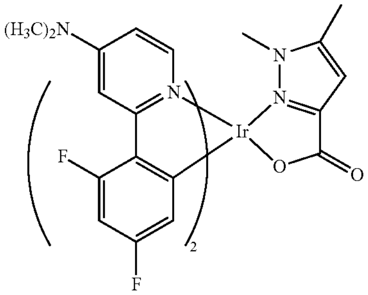

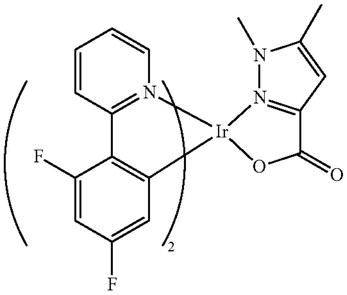

-continued
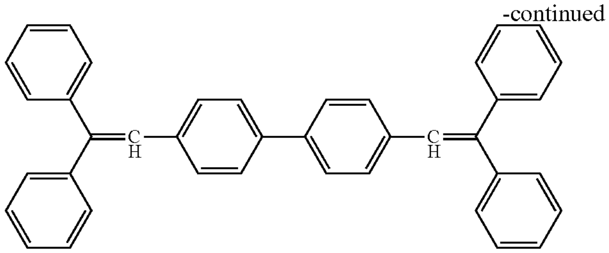
DPVBi
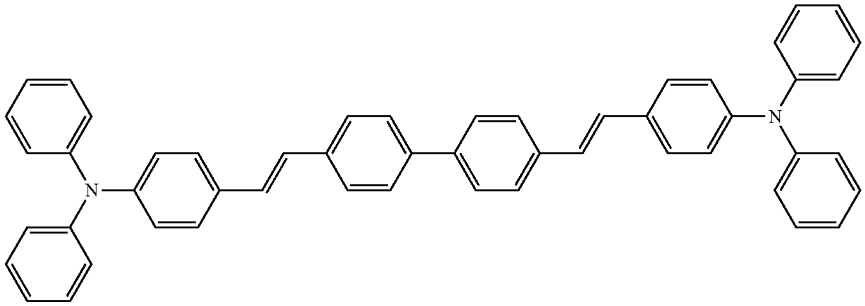
DPAVBi
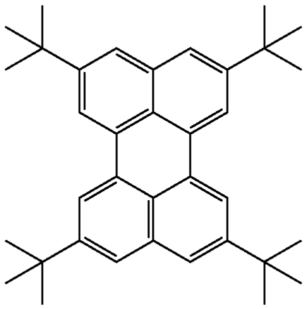
TBPe
Non-limiting examples of red dopants are compounds represented by the following Formulae.
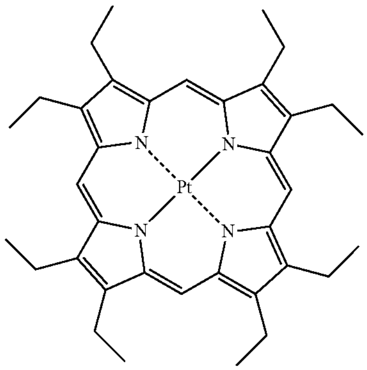
PtOEP
-continued
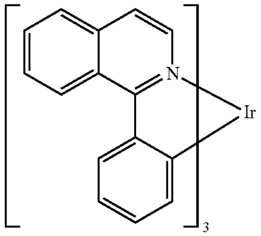
Ir(piq)$_3$
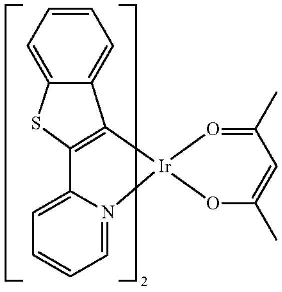
Btp$_2$Ir(acac)

-continued
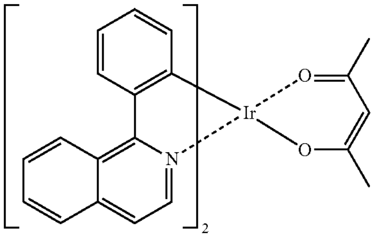
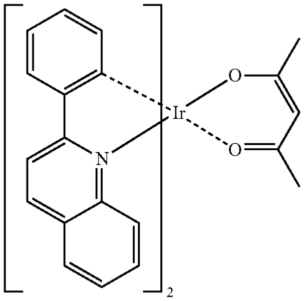
Ir(pq)2(acac)
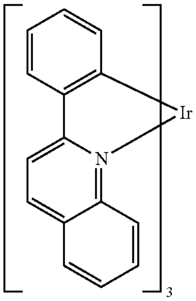
Ir(2-phq)3
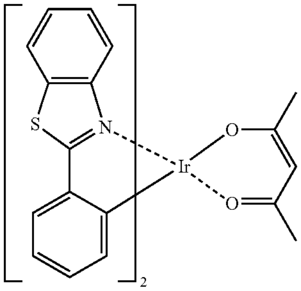
Ir(BT)2(acac)
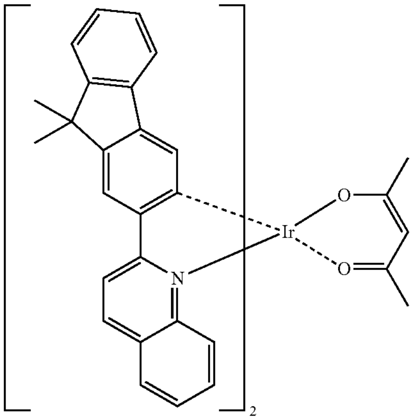
Ir(flq)2(acac)
-continued
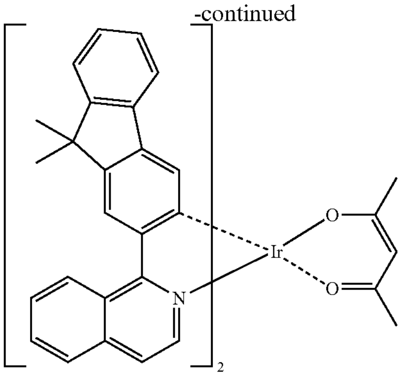
Ir(fliq)2(acac)
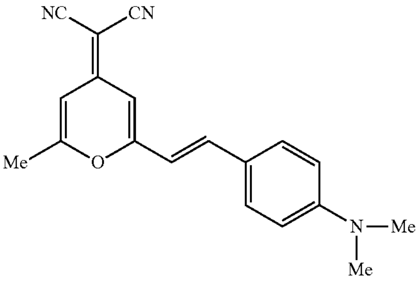
DCM
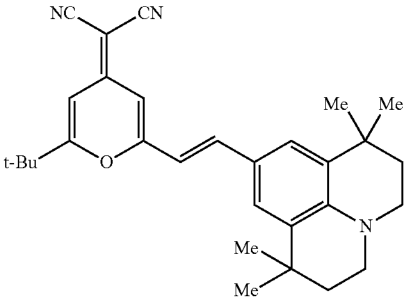
DCJTB
Non-limiting examples of green dopants are compounds represented by the following Formulae.
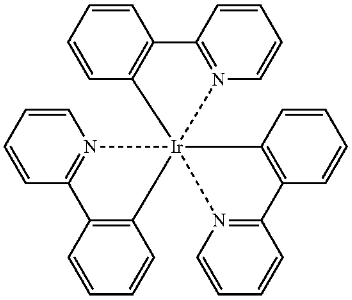
Ir(ppy)3

-continued

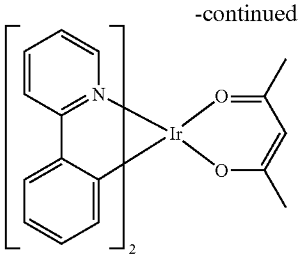

Ir(ppy)2(acac)

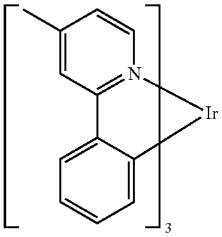

Ir(mpyp)3

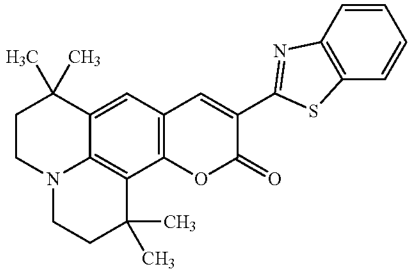

C545T

Non-limiting examples of dopants for the EML 16 are a Pt-complex and an Os-complex.

In the organic light-emitting device 10, at least one of the EML 16, the EIL, the ETL, and the functional layer having both electron injection and electron transport capabilities includes a heterocyclic compound according to Formula 1, and the EML 16 may additionally include an arylamine compound.

The EML 16 may include a heterocyclic compound according to Formula 1 as a fluorescent dopant. In some embodiments the EML 16 may further include a known host in addition to the heterocyclic compound of Formula 1 above. In some embodiments, the EML 16 may further include a heterocyclic compound according to Formula 1 above as a blue fluorescent dopant.

When the EML 16 includes both a host and a dopant, the amount of the dopant may be from about 0.01 parts to about 15 parts by weight based on 100 parts by weight of the host. However, the amount of the dopant is not limited to this range.

A thickness of the EML 16 may be from about 100 Å to about 1000 Å, and, in some embodiments, may be from about 200 Å to about 600 Å. When the thickness of the EML 16 is within these ranges, the EML 16 may have improved light emitting properties without imparting a substantial increase in driving voltage to the corresponding light-emitting device.

Then, an ETL may be formed on the EML 16 using any of a variety of methods, such as vacuum deposition, spin coating, casting, or the like. When the ETL is formed using vacuum deposition or spin coating, the deposition and coating conditions may be similar to those for the formation of the HIL, though the deposition and coating conditions may vary depending upon the compound that is used to form the ETL. An ETL-forming material may be at least one of a heterocyclic compound according to Formula 1 and any known ETL-forming material. Non-limiting examples of known ETL forming materials are a quinoline derivative, such as tris(8-hydroxyquinolinato)aluminum (Alq3), 3-(4-t-butylphenyl)-4-phenyl-5-(4-biphenyl)-1,2,4-triazole (TAZ), bis(2-methyl-8-quinolinolato)(para-phenylphenolato)aluminium(III) (BAlq), beryllium bis(benzoquinolin-10-olate ($Bebq_2$), 9,10-di(naphthalene-2-yl)anthracene (ADN), Compound 201, and Compound 202.

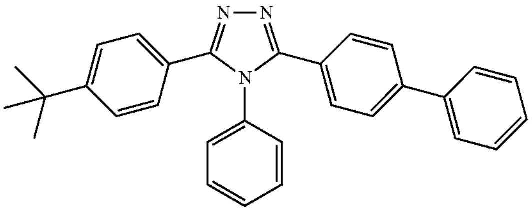

TAZ

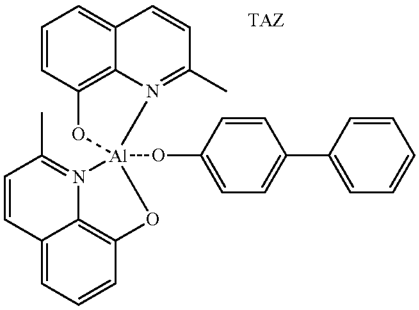

Balq

Compound 201

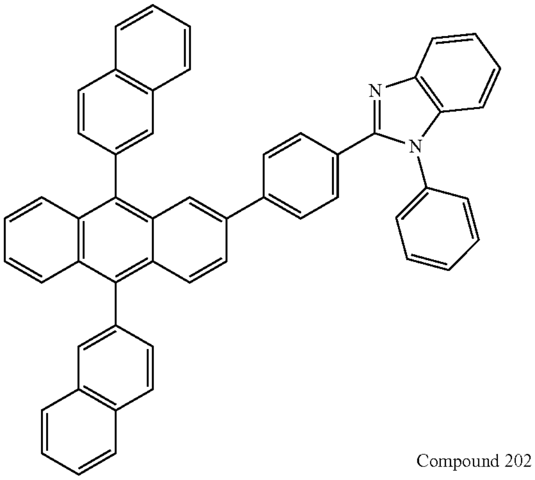

Compound 202

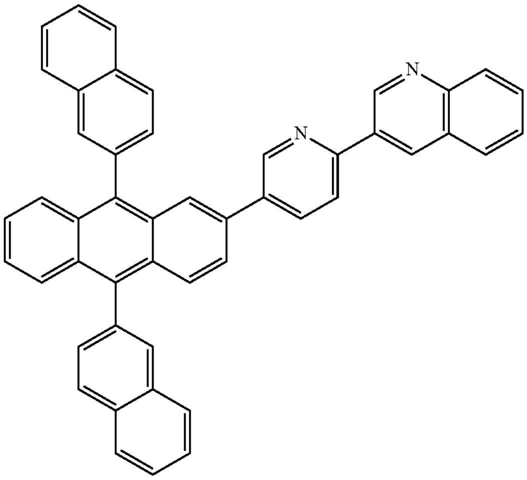

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without imparting a substantial increase in driving voltage to the light-emitting device.

The ETL may further include a metal complex, in addition to at least one of the heterocyclic compounds of Formula 1 and a known ETL-forming material. The metal complex may be a lithium (Li) complex. Non-limiting examples of the Li complex include lithium quinolate (LiQ) and Compound 203 below.

Compound 203

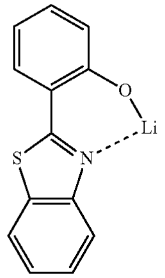

An EIL, which facilitates injection of electrons from the cathode, may be formed on the ETL. Examples of EIL-forming materials are LiF, NaCl, CsF, $Li_2O$, and BaO. The deposition and coating conditions for forming the EIL 18 may be similar to those for the formation of the HIL, though the deposition and coating conditions may vary according to the material that is used to form the EIL 18. A thickness of the EIL may be from about 1 Å to about 100 Å, and in some embodiments, from about 3 Å to about 90 Å. When the thickness of the EIL is within these ranges, the EIL may have satisfactory electron injection ability without imparting a substantial increase in driving voltage to the corresponding light-emitting device.

The second electrode 19 may be formed on the organic layer 15. The second electrode 19 may be a cathode that is an electron injection electrode. Suitable materials for forming the second electrode 19 are a metal, an alloy and an electro-conductive compound that has a low work function, or mixtures thereof. For example, the second electrode 19 may be formed as a transmission electrode in a thin film form using Li, Mg, Al, Al:Li, Ca, Mg:In, Mg:Ag, or the like. In some embodiments, to manufacture a top-emission light-emitting device, the transmission electrode may be formed of indium tin oxide (ITO) or indium zinc oxide (IZO).

When a phosphorescent dopant is used in the EML, a hole blocking layer (HBL) may be formed between the HTL and the EML 16 or between the functional layer having both hole injection and transport capabilities and the EML 16 by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. The HBL may be formed using a known HBL-forming material; examples are an oxadiazole derivative, a triazole derivative, a phenanthroline derivative, or the like, but are not limited thereto. For example, the HBL may be formed from 2,9-dimethyl-4,7-diphenyl-1,10-phenanthroline (BCP), which is represented by the following Formula.

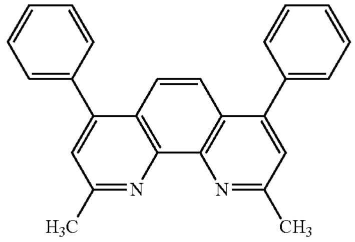

BCP

A thickness of the HBL may be from about 20 Å to about 1000 Å, and in some embodiments, may be from about 30 Å to about 300 Å. When the thickness of the HBL is within these ranges, the HBL may have improved hole blocking properties without imparting a substantial increase in driving voltage to the corresponding light-emitting device.

According to an embodiment of the present invention, an organic light-emitting display apparatus includes: a transistor with a source, a drain, a gate, and an active layer; and the above-described organic light-emitting device, one of the source and the drain of the transistor being electrically connected to the first electrode of the organic light-emitting device.

The active layer of the transistor may be in any of a variety of forms; examples are an amorphous silicon layer, a crystalline silicon layer, an organic semiconductor layer, or an oxide semiconductor layer.

As used herein, examples of the "unsubstituted $C_1$-$C_{30}$ alkyl group" (or "$C_1$-$C_{30}$ alkyl group") are $C_1$-$C_{30}$ linear or branched alkyl groups, such as methyl, ethyl, propyl, isobutyl, sec-butyl, pentyl, iso-amyl, and hexyl. Examples of the substituted $C_1$-$C_{30}$ alkyl groups are the unsubstituted $C_1$-$C_{30}$ alkyl group of which at least one hydrogen atom is substituted with one of a deuterium atom, a halogen atom, a hydroxyl group, a cyano group, an amino group, a nitro group, an amidino group, hydrazine, hydrazone, a carboxyl group or a salt thereof, sulfonic acid or a salt thereof, phosphoric acid or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_6$-$C_{30}$ aryl group, an unsubstituted $C_6$-$C_{30}$ aryloxy group, a $C_6$-$C_{30}$ arylthio group, a $C_2$-$C_{30}$ heteroaryl group, —$N(Q_{101})(Q_{102})$, and —$Si(Q_{103})(Q_{104})(Q_{105})$, $(Q_{106})$, $Q_{101}$ to $Q_{106}$ each independently being one of a hydrogen atom, a $C_1$-$C_{30}$ alkyl group, a $C_2$-$C_{30}$ alkenyl group, a $C_2$-$C_{30}$ alkynyl group, a $C_6$-$C_{30}$ aryl group, and $C_2$-$C_{30}$ heteroaryl group.

As used herein, the unsubstituted $C_2$-$C_{30}$ alkenyl group is a hydrocarbon chain having a carbon-carbon double bond in the center or at a terminal of the unsubstituted $C_2$-$C_{30}$ alkyl group. Examples of the unsubstituted $C_2$-$C_{30}$ alkenyl group are ethenyl, propenyl, and butenyl groups. At least one hydrogen atom in the unsubstituted $C_2$-$C_{30}$ alkenyl group may be substituted with the substituents described in conjunction with the substituted $C_1$-$C_{30}$ alkyl group.

As used herein, the unsubstituted $C_2$-$C_{30}$ alkynyl group is an alkyl group having at least one carbon-carbon triple bond in the center or at a terminal of the $C_2$-$C_{30}$ alkyl group. Examples of the unsubstituted $C_2$-$C_{30}$ alkynyl group are ethynyl and propynyl. The substituted $C_2$-$C_{30}$ alkynyl groups are substituted $C_2$-$C_{30}$ alkynyl groups of which at least one hydrogen atom is substituted with the substituents described in connection with substituted $C_1$-$C_{30}$ alkyl groups.

As used herein, the unsubstituted $C_1$-$C_{30}$ alkoxy group may be represented by the Formula of –OA (wherein A is a unsubstituted $C_1$-$C_{30}$ alkyl group as described above, and non-limiting examples thereof are methoxy, ethoxy, and isopropyloxy. The substituted $C_1$-$C_{30}$ alkoxy group may be a $C_1$-$C_{30}$ alkyl group of which at least one hydrogen atom is substituted with the same substituents as described in connection with the substituted $C_1$-$C_{30}$ alkyl group.

As used herein, the unsubstituted $C_3$-$C_{30}$ cycloalkyl group may be a saturated $C_3$-$C_{30}$ monocyclic, bicyclic, or tricyclic non-aromatic hydrocarbon group. Non-limiting examples thereof are cyclopropyl, cyclobutyl, cyclopentyl, cyclohexyl, cycloheptyl, cyclooctyl, and decahydronaphthalenyl. The substituted $C_3$-$C_{30}$ cycloalkyl group may be a $C_3$-$C_{30}$ cycloalkyl group of which at least one hydrogen atom is substituted with the same substituents as described in connection with the substituted $C_1$-$C_{30}$ alkyl group.

As used herein, the unsubstituted $C_3$-$C_{30}$ cycloalkenyl group may be an unsaturated $C_3$-$C_{30}$ monocyclic, bicyclic, or tricyclic non-aromatic hydrocarbon group. Non-limiting examples thereof are cyclopentenyl, and cyclohexenyl. The substituted $C_3$-$C_{30}$ cycloalkenyl group may be a $C_3$-$C_{30}$ cycloalkenyl group of which at least one hydrogen atom is substituted with the same substituents as described in connection with the substituted $C_1$-$C_{30}$ alkyl group.

The unsubstituted $C_6$-$C_{30}$ aryl group is a monovalent group having a carbocyclic aromatic system having 6 to 30 carbon atoms including at least one aromatic ring. The unsubstituted $C_6$-$C_{30}$ arylene group is a bivalent group having a carbocyclic aromatic system having 6 to 30 carbon atoms including at least one aromatic ring. When the aryl group or the arylene group has at least two rings, they may be fused to each other via a single bond. The substituted $C_6$-$C_{30}$ aryl group is a $C_6$-$C_{30}$ aryl group of which at least one hydrogen atom is substituted with the same substituents as described in connection with the substituted $C_1$-$C_{30}$ alkyl group. The substituted $C_6$-$C_{30}$ arylene group is a $C_6$-$C_{30}$ arylene group of which at least one hydrogen atom is substituted as the same substituents as described in connection with the substituted $C_1$-$C_{30}$ alkyl group.

As used herein, the unsubstituted $C_6$-$C_{30}$ aryloxy group is represented by —$OA_2$ ($A_2$ being a substituted or unsubstituted $C_6$-$C_{30}$ aryl group). The substituted $C_6$-$C_{30}$ aryloxy group is a $C_6$-$C_{30}$ aryloxy group of which at least one hydrogen atom is substituted with the same substituents as described in connection with the substituted $C_1$-$C_{30}$ alkyl group.

As used herein, the unsubstituted $C_6$-$C_{30}$ arylthio group is represented by —$SA_3$ ($A_3$ being a substituted or unsubstituted $C_3$-$C_{30}$ aryl group). The substituted $C_6$-$C_{30}$ arylthio group is a $C_6$-$C_{30}$ arylthio group of which at least one hydrogen atom is substituted with the same substituents as described in connection with the substituted $C_1$-$C_{30}$ alkyl group.

The unsubstituted $C_2$-$C_{30}$ heteroaryl group is a monovalent group having at least one aromatic ring and having at least one heteroatom in the at least one aromatic ring, the at least one heteroatom being selected from N, O, P, and S, the at least one aromatic ring having at least one carbon atom. The unsubstituted $C_2$-$C_{30}$ heteroarylene group is a bivalent group having at least one aromatic ring, the at least one aromatic ring having at least one of the heteroatoms selected from N, O, P, and S, the at least one aromatic ring having at least one carbon atom. In this regard, when the heteroaryl group and the heteroarylene group have at least two rings, the at least two rings may be fused to each other via a common single bond. The substituted $C_2$-$C_{30}$ heteroaryl group is a $C_2$-$C_{30}$ heteroaryl group of which at least one hydrogen atom is substituted with the same substituents as described in connection with the substituted $C_1$-$C_{30}$ alkyl group. The substituted $C_2$-$C_{30}$ heteroarylene group is a $C_2$-$C_{30}$ heteroarylene group of which at least one hydrogen atom is substituted with the same substituents as described in connection with the substituted $C_1$-$C_{30}$ alkyl group.

Hereinafter, the present invention will be described in detail with reference to the following synthesis examples and other examples. However, these examples are for illustrative purposes only and are not intended to limit the scope of the present invention.

Synthesis Example 1

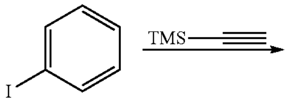

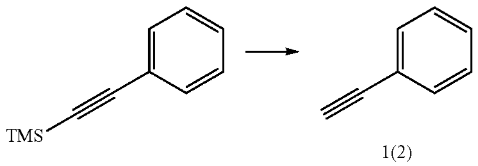

1(1) 1(2)

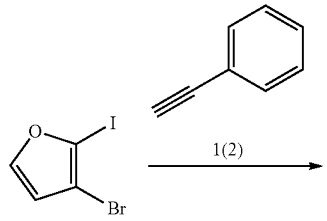

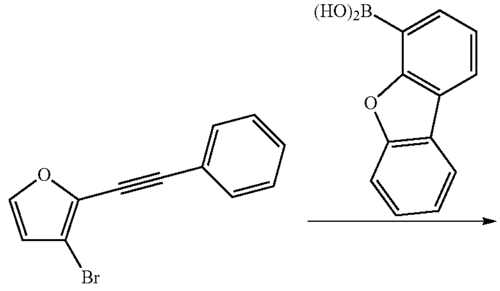

1(3)

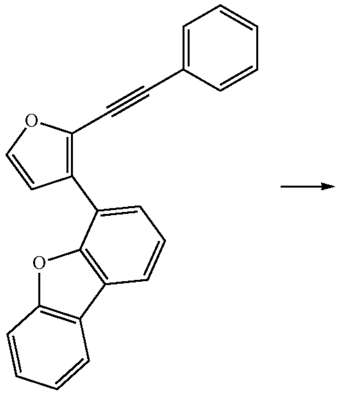

1(4)

-continued

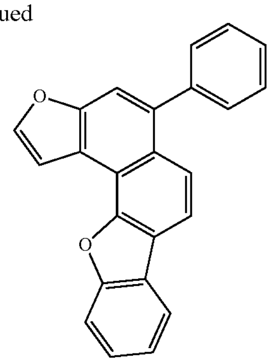

1

Synthesis of Intermediate 1(1)

A quantity of 22.0 g (107.84 mmol) of iodobenzene, Bis(triphenylphosphine)palladium(II) dichloride ($PdCl_2(PPh_3)_2$), 1.6 g (8.63 mmol) of CuI were added to 200 mL of a mixture of anhydrous toluene and diisopropylamine in a 5:1 volume ratio and stirred at room temperature for 5 minutes. Then, 9.1 ml (92.99 mmol) of ethynyltrimethylsilane was slowly added into the mixture and stirred at 80° C. for 18 hours. After completion of the reaction, 150 mL of distilled water was added, followed by three times of extraction each with 80.0 mL of methylene chloride. The organic layer was collected and was dried using magnesium sulfate to evaporate the solvent. The residue was separated and purified by silica gel column chromatography to obtain 17.86 g (102.46 mmol) of Intermediate 1(1) (Yield: 95.0%).

This compound was identified using liquid chromatography-mass spectroscopy (LC-MS).

$C_{11}H_{14}Si$: M+175.09

Synthesis of Intermediate 1(2)

A quantity of 5.0 g (27.7 mmol) of Intermediate 1(1) was mixed with 50 ml of tetrahydrofuran (THF), and 40 mL of tetrabutylammonium fluoride in THF (1.0M) was dropwise added thereinto and stirred for about 30 minutes. After 500 ml of water was added to the reaction solution, the reaction solution was extracted three times each with 30 mL of ethyl ether. The organic layers were combined and dried using magnesium sulfate, and the solvent was then removed to yield a crude product residue. The residue was purified by silica gel column chromatography to obtain 2.8 g of Intermediate 1(2) (Yield: 93%).

This compound was identified using LC-MS.

$C_8H_6$: M+ 103.05

Synthesis of Intermediate 1(3)

A quantity of 5.0 g (18.39 eq) of 3-bromo-2-iodo-furan, 1.1 g (0.92 mmol) of $Pd(PPh_3)_4$, and 130 mg (0.92 eq) of CuI were combined and subjected to a vacuum. The vacuum was then purged with $N_2$ gas, and the reaction mixture was stirred with addition of 50 ml of THF. A quantity of 7.69 mL (5.18 mmol) of triethylamine and 2.25 g (2 eq) of Intermediate 1(2) were slowly dropwise added thereinto and then stirred at room temperature for about 2 hours in a $N_2$ atmosphere. After removing the solvent using a rotary evaporator, 50 mL of water was added to the resulting reaction solution, which was then extracted three times with 50 mL portions of ethyl ether. The organic layers were combined and dried using magnesium sulfate. The solvent was then removed to yield a crude product residue. The residue was purified using silica gel column chromatography to obtain 2.8 g of Intermediate 1(3) (Yield: 61%).

This compound was identified using LC-MS.

$C_{12}H_7BrO$: M+ 246.95

Synthesis of Intermediate 4(1)

A quantity of 3.0 g (12.14 mmol) of Intermediate 1(3), 3.86 g (18.21 mmol) of dibenzofuran boronic acid, 700 mg (0.61 eq) of $Pd(PPh_3)_4$, and 5.03 g (36.42 eq) of $K_2CO_3$ were dissolved in a mixture of 30.0 mL of THF and 10.0 mL of distilled water. The resulting mixture was then refluxed for about 24 hours while being stirred after a temperature increase to about 120° C. The reaction solution was then cooled to room temperature, followed by extraction three times with 50 mL portions of water and three times with 50 mL portions of diethyl ether. The organic layers were combined and dried using magnesium sulfate. The solvent was then removed to yield a crude product residue. The residue was purified using silica gel column chromatography to obtain 2.1 g of Intermediate 1(4) (Yield: 49%).

This compound was identified using LC-MS.

$C_{24}H_{14}O_2$: M+ 335.10

Synthesis of Compound 1

A quantity of 2.0 g (5.98 mmol) of Intermediate 1(4) was dissolved in 50 mL of methylene chloride (MC), and 16.5 mL (215.33 mmol) of trifluoroacetic acid was dropwise added thereinto. The resulting mixture was stirred at room temperature for about 1 hour.

After completion of the reaction, the reaction solution was extracted three times with 15.0 mL portions of water and three times with 20.0 mL portions of diethyl ether.

The organic layers were combined and dried using magnesium sulfate. The solvent was then removed to produce a crude product residue. The residue was purified using silica gel column chromatography to obtain 1.9 g of Compound 1 (Yield: 95%). This compound was identified using LC-MS and nuclear magnetic resonance (NMR).

Synthesis Example 2

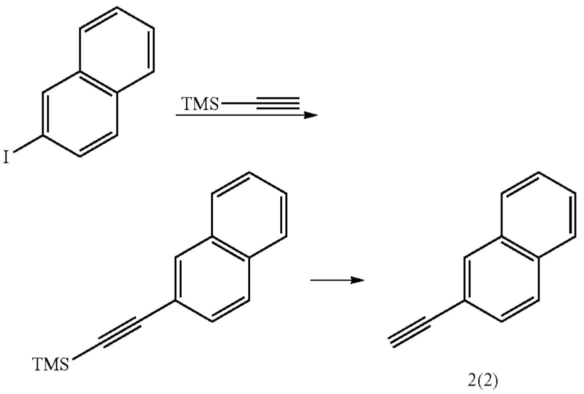

2(1) 2(2)

-continued

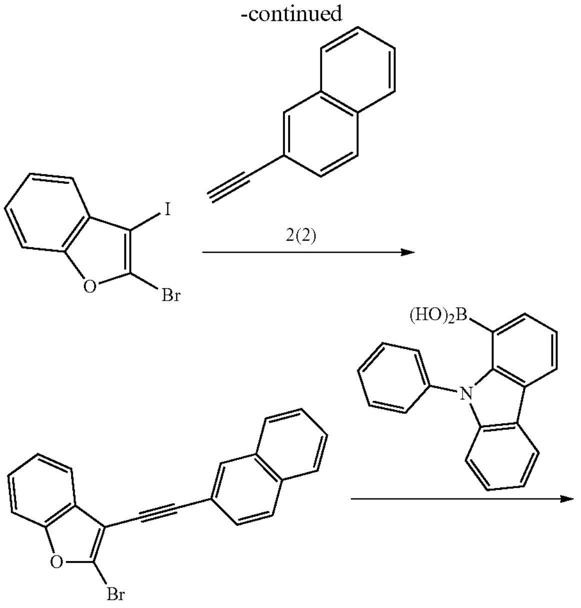

2(3)

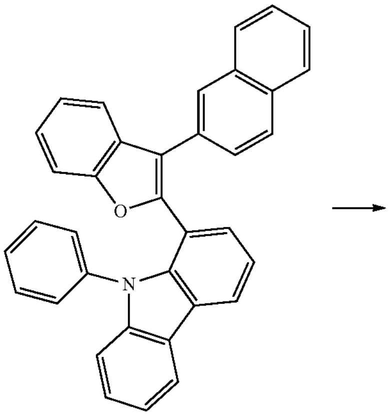

2(4)

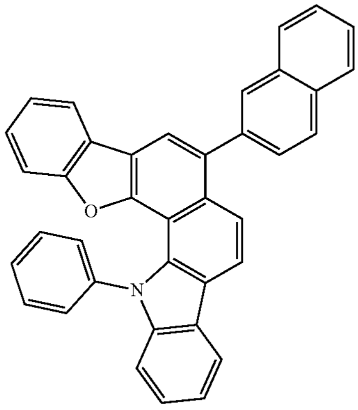

2

Compound 2 was synthesized in the same manner as in Synthesis Example 1, except that 2-iodonaphthalene, instead of iodobenzene, was used to synthesize Intermediate 2(1); 2-bromo-3-iodo-benzofuran, instead of 3-Bromo-2-iodo-furan, was used as a starting material to synthesize Intermediate 2(3); and 9-phenyl-9H-carbazole-1-boronic acid, instead of dibenzofuran boronic acid, was used to synthesize Intermediate 2(4). This compound was identified using LC-MS and nuclear magnetic resonance (NMR).

Synthesis Example 3

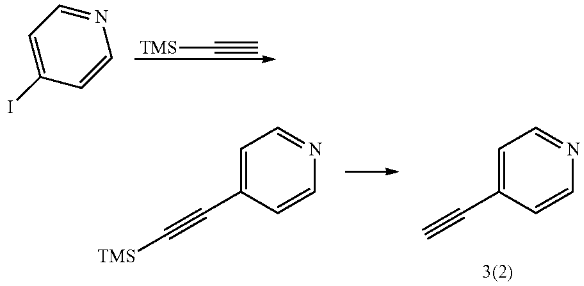

3(1) 3(2)

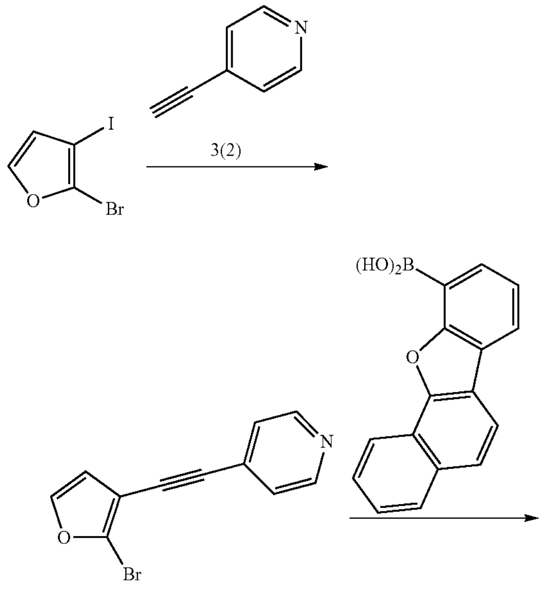

3(3)

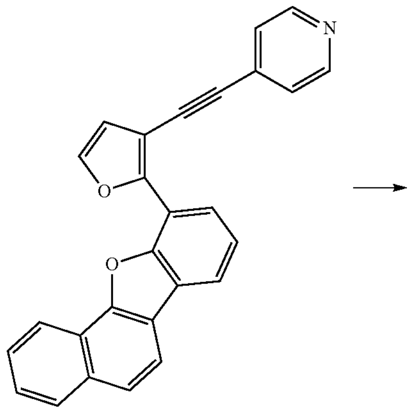

3(4)

-continued

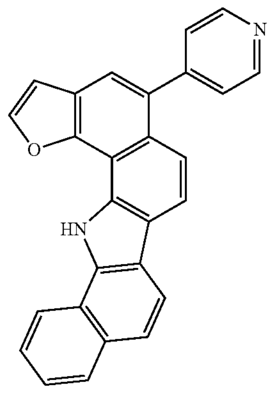

3

Compound 3 was synthesized in the same manner as in Synthesis Example 1, except that 4-iodopyridine, instead of iodobenzene, was used to synthesize Intermediate 3(1); 2-bromo-3-iodo-furan, instead of 3-bromo-2-iodo-furan, was used as a starting material to synthesize Intermediate 3(3); and benzo[b]naphtho[2,1-d]furan boronic acid, instead of dibenzofuran boronic acid, was used to synthesize Intermediate 3(4). This compound was identified using LC-MS and nuclear magnetic resonance (NMR).

Synthesis Example 4

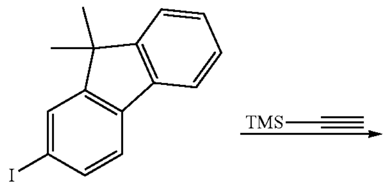

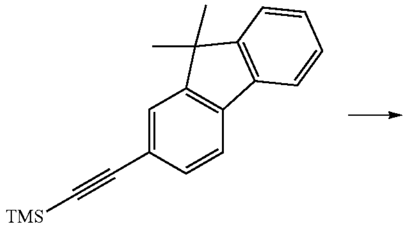

4(1)

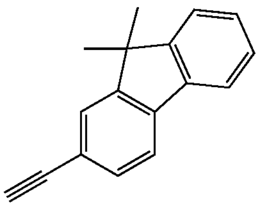

4(2)

-continued

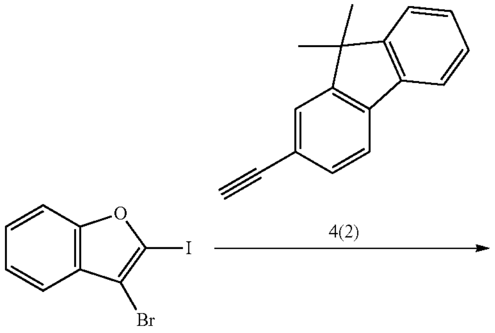

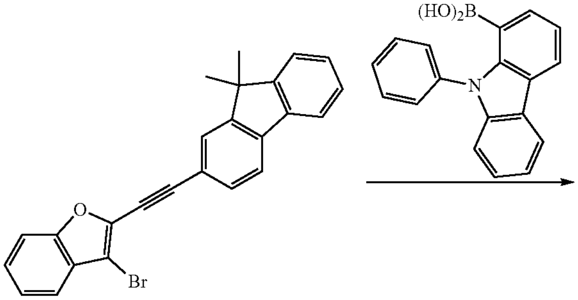

4(3)

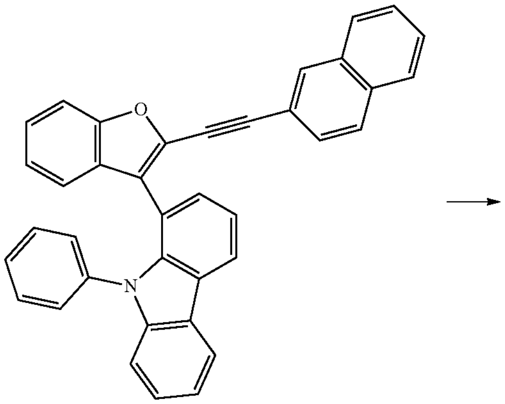

4(4)

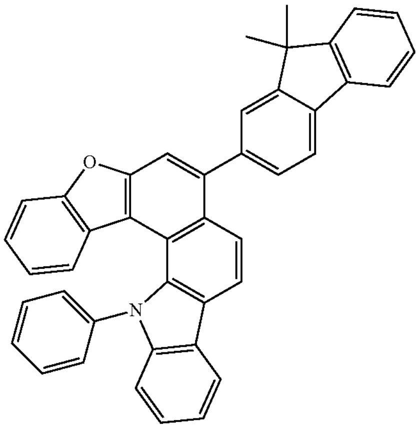

4

Compound 4 was synthesized in the same manner as in Synthesis Example 1, except that 2-Iodo-9,9-dimethyl-9H-fluorene, instead of iodobenzene, was used to synthesize Intermediate 4(1); 3-bromo-2-iodo-benzofuran, instead of 3-bromo-2-iodo-furan, was used as a starting material to synthesize Intermediate 4(4); and 9-phenyl-9H-carbazole-1-boronic acid, instead of dibenzofuran boronic acid, was used to synthesize Intermediate 4(4). This compound was identified using LC-MS and nuclear magnetic resonance (NMR).

Synthesis of Intermediates A, B, C, D, E, F, G, H, I, J, K, and L

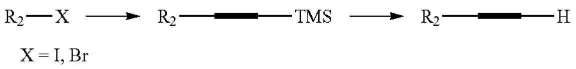

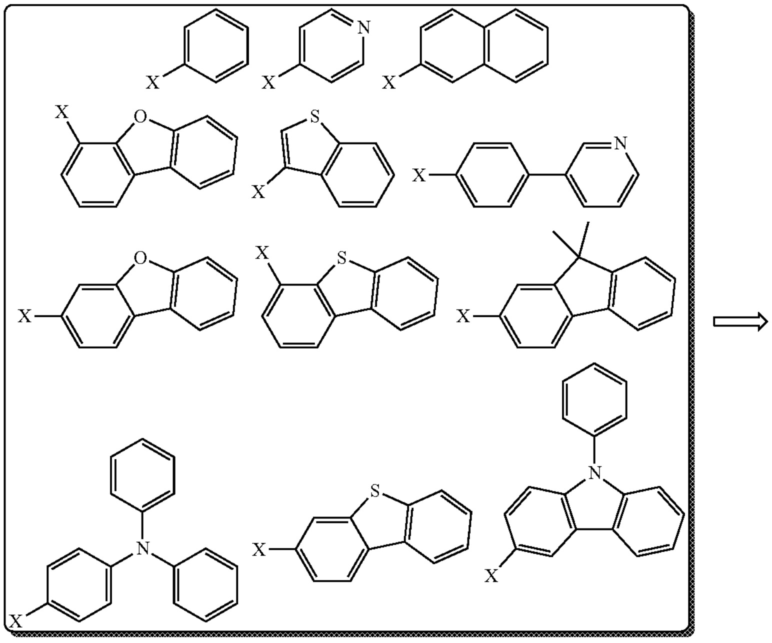

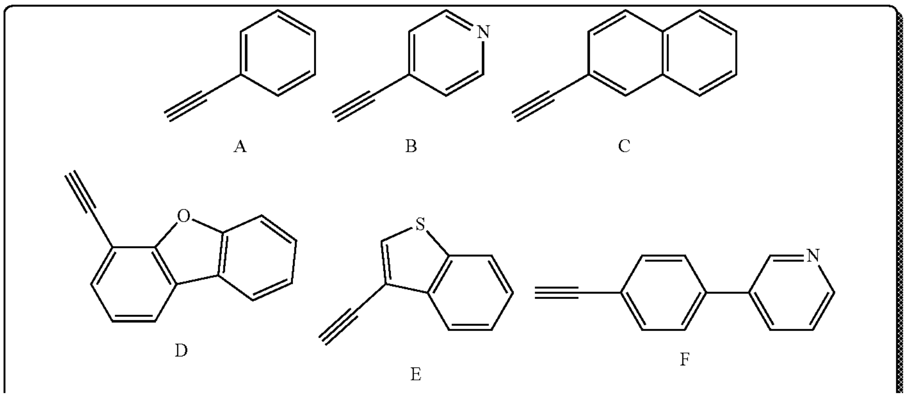

A B C

D E F

-continued

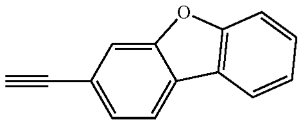

G

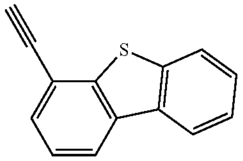

H

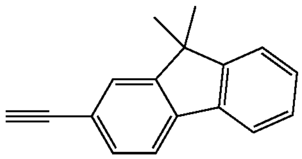

I

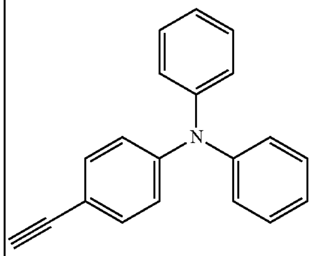

J

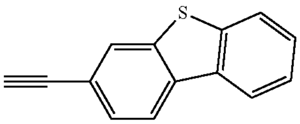

K

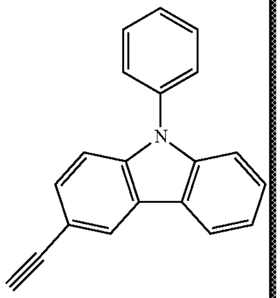

L

Intermediates A to L were synthesized in the same manner as in Reaction schemes 1 and 2 of the above representative synthesis examples using the same equivalents of reactants.

| | Yield (%) | | |
|---|---|---|---|
| Intermediate | Reaction scheme 1 | Reaction scheme 2 | LC-MS |
| A | 95 | 93 | 103.13 |
| B | 96 | 92 | 104.11 |
| C | 94 | 95 | 153.19 |
| D | 95 | 91 | 193.22 |
| E | 91 | 96 | 159.21 |
| F | 97 | 95 | 180.21 |
| G | 92 | 95 | 193.22 |
| H | 93 | 97 | 209.29 |
| I | 95 | 96 | 219.29 |
| J | 92 | 98 | 270.33 |
| K | 98 | 94 | 209.28 |
| L | 94 | 95 | 268.32 |

Synthesis of Compounds 5, 12, 13, 19, 20, 21, 25, 26, 27, 28, 29, 36, 39, 45, 51, and 54

Seventeen compounds were synthesized in the same manner as in Reaction schemes 3, 4, and 5 of the above representative synthesis examples using the same equivalents of reactants.

| | Yield (%) | | | |
|---|---|---|---|---|
| Compound | Reaction scheme1 | Reaction scheme2 | Reaction scheme2 | LC-MS |
| 5 | 55 | 77 | 85 | 528.60 |
| 12 | 52 | 66 | 88 | 576.60 |
| 13 | 49 | 79 | 89 | 501.55 |
| 19 | 51 | 75 | 87 | 457.59 |
| 20 | 53 | 68 | 92 | 593.75 |
| 21 | 62 | 72 | 84 | 471.60 |
| 25 | 58 | 73 | 79 | 458.58 |
| 26 | 53 | 69 | 95 | 594.70 |
| 27 | 52 | 68 | 91 | 481.66 |
| 28 | 55 | 80 | 93 | 616.74 |
| 29 | 54 | 73 | 92 | 600.60 |
| 36 | 56 | 75 | 98 | 594.74 |
| 39 | 58 | 71 | 96 | 578.67 |
| 45 | 52 | 77 | 94 | 593.76 |
| 51 | 49 | 76 | 89 | 594.74 |
| 54 | 53 | 69 | 95 | 578.66 |

$^1$H NMR ($CDCl_3$, 400 MHz) data

| Compound | NMR data |
|---|---|
| 1 | 7.64(s, 1H), 7.52(s, 1H), 7.49(s, 2H), 7.48(s, 2H), 7.42(d, 1H), 7.32(d, 2H), 7.22-7. 13(m, 4H), 6.66 (d, 1H) |
| 2 | 7.89(d, 1H), 7.73-7.70(m, 2H), 7.67 (s, 2H), 7.56-7.54 (m, 3H), 7.49 (s, 1H), 7.42(d, 2H), 7.32-7.30 (m, 7H), 7.19 (s, 1H), 7.13 (s, 1H), 7.08 (s, 1H) |
| 3 | 8.65 (s, 2H), 7.71 (d, 1H), 7.67-7.60(m, 4H), 7.52(d, 1H), 7.49(s, 2H), 7.32(d, 1H), 7.13(s, 2H), 6.66 (d, 1H) |
| 4 | 7.90(d, 1H), 7.84(d, 1H), 7.77(d, 1H), 7.64(d, 1H), 7.60(s, 1H), 7.55(d, 3H), 7.49(d, 1H), 7.42-7.38(m, 3H), 7.30-7.28 (m, 6H), 7.19 (s, 1H), 7.13 (d, 1H), 7.08 (s, 1H), 7.00 (d, 2H), 1.67 (s, 6H) |
| 5 | 8.81(s, 1H), 8.55(d, 1H), 7.97(d, 1H), 7.86 (d, 1H), 7.78 (s, 2H), 7.67(d, 2H), 7.64 (d, 1H), 7.54 (s, 4H), 7.49 (s, 1H), 7.44 (d, 1H), 7.42(d, 1H), 7.33(d, 1H), 7.32(t, 2H), 7.19(d, 1H), 7.13(d, 1H) |

-continued

| Compound | NMR data |
|---|---|
| 6 | 7.77 (d, 1H), 7.64 (s, 1H), 7.55-7.52 (m, 3H), 7.46 (s, 1H), 7.40-7.30 (m, 12H), 7.08 (d, 2H), 7.00 (s, 3H), 6.66 (s, 1H) |
| 7 | 7.77 (d, 1H), 7.71 (t, 1H), 7.55-7.52 (m, 2H), 7.49-7.40 (m, 5H), 7.30 (s, 6H), 7.19 (s, 1H), 7.13 (m, 2H), 7.08 (s, 1H), 7.00 (s, 1H), 6.66 (s, 1H) |
| 8 | 7.71 (s, 1H), 7.52 (d, 1H), 7.49 (t, 2H), 7.42 (d, 1H), 7.23 (s, 2H), 7.19 (d, 1H), 7.13 (t, 2H), 7.01 (s, 4H), 6.66 (s, 1H), 6.62 (d, 2H), 6.52 (d, 2H), 6.46 (t, 4H) |
| 9 | 7.62 (d, 1H), 7.52 (d, 1H), 7.49 (s, 2H), 7.42 (s, 1H), 7.23 (t, 2H), 7.19 (t, 1H), 7.13 (d, 2H), 7.01 (s, 4H), 6.66 (t, 1H), 6.62 (t, 2H), 6.52 (d, 2H), 6.46 (s, 4H) |
| 10 | 7.90 (d, 1H), 7.86 (d, 1H), 7.80-7.78 (m, 3H), 7.64(s, 1H), 7.52 (d, 1H), 7.40 (d, 1H), 7.33-7.30 (m. 5H), 6.66 (s, 1H), |
| 11 | 8.08 (d, 1H), 7.86-7.84 (m, 2H), 7.78 (t, 1H), 7.67-7.64 (m, 3H), 7.55 (t, 1H), 7.49 (d, 2H), 7.33-7.31 (s, 4H), 7.19 (d, 2H), 7.13 (d, 2H) |
| 12 | 7.95(d, 1H), 7.77(s, 1H), 7.55-7.54 (m, 4H), 7.46 (s, 1H), 7.40 (m, 2H), 7.30 (m, 11H), 7.08 (d, 2H), 7.00 (d, 3H) |
| 13 | 7.95 (d, 1H), 7.77 (d, 1H), 7.55-7.54 (m, 2H), 7.49 (s, 2H), 7.46 (t, 1H), 7.42-7.30 (m, 8H), 7.19 (s, 1H), 7.13 (s, 2H), 7.08 (s, 1H), 7.00 (s, 1H) |
| 14 | 7.95(d, 1H), 7.54 (s, 1H), 7.49 (t, 2H), 7.42 (d, 1H), 7.23 (s, 2H), 7.19 (t, 1H), 7.13 (t, 2H), 7.01 (d, 4H), 6.62 (s, 2H), 6.52 (d, 2H), 6.46 (t, 4H) |
| 15 | 8.59 (d, 1H), 7.90 (s, 1H), 7.80-7.75 (m, 3H), 7.64 (t, 1H), 7.52 (d, 1H), 7.40-7.33 (m, 5H), 6.66 (d, 1H) |
| 16 | 8.59 (d, 1H), 7.95 (d, 1H), 7.77-7.54 (m, 4H), 7.49 (t, 1H), 7.46-7.40 (m, 2H), 7.38-7.30 (m, 7H), 7.13 (d, 1H), 7.08-7.00 (m, 2H) |
| 17 | 8.59 (d, 1H), 7.95 (t, 1H), 7.75 (t, 1H), 7.54 (d, 1H), 7.49 (d, 1H), 7.38 (t, 1H), 7.23 (s, 2H), 7.13 (d, 1H), 7.01 (s, 4H), 6.62 (d, 2H), 6.52 (s, 2H), 6.46-6.40 (m, 4H) |
| 18 | 8.59 (d, 1H), 7.95 (s, 1H), 7.77 (d, 1H), 7.75 (t, 1H), 7.55-7.46 (m, 4H), 7.40-7.38 (m, 2H), 7.32-7.30 (m, 11H), 7.08 (s, 1H), 7.00 (t, 2H) |
| 19 | 8.00 (d, 1H), 7.86 (s, 1H), 7.78 (t, 2H), 7.64 (d, 1H), 7.55 (s, 1H), 7.49 (t, 1H), 7.42 (d, 1H), 7.40 (d, 1H), 7.35-7.29 (m, 5H), 7.19 (s, 1H), 7.13 (t, 1H) |
| 20 | 8.08 (d, 1H), 7.55 (d, 2H), 7.40 (s, 2H), 7.30-7.23 (m, 8H), 7.01-7.00 (m, 6H), 6.62 (t, 2H), 6.52 (d, 2H), 6.46 (m, 4H) |
| 21 | 8.08 (d, 1H), 7.86 (s, 1H), 7.78 (d, 1H), 7.74 (t, 1H), 7.53 (d, 1H), 7.49-7.39 (m, 4H), 7.33-7.31 (m, 2H), 7.19-7.13 (m, 3H), 6.95 (d, 1H), 2.21 (s, 3H) |
| 22 | 8.00 (t, 1H), 7.86 (s, 1H), 7.78-7.76 (m, 3H), 7.55 (d, 1H), 7.46 (d, 1H), 7.40 (t, 1H), 7.33-7.29 (m, 9H), 7.08 (t, 1H), 6.95 (s, 1H), 2.21(s, 3H) |
| 23 | 8.08 (d, 1H), 7.91 (t, 4H), 7.86 (s, 1H), 7.78 (s, 1H), 7.67-7.63 (m, 3H), 7.55-7.54 (m, 3H), 7.40-7.38 (m, 6H), 7.33-7.30 (m, 9H), 7.08 (t, 1H), 7.00 (d, 2H) |
| 24 | 8.59 (t, 1H), 8.00 (s, 1H), 7.78 (d, 1H), 7.75 (d, 1H), 7.64 (t, 1H), 7.55 (d, 1H), 7.49-7.40 (m, 3H), 7.38-7.33 (m, 3H), 7.29 (s, 1H), 7.19-7.13 (m, 2H) |
| 25 | 9.23 (t, 1H), 8.45 (s, 1H), 7.86-7.78 (m, 3H), 7.64 (d, 1H), 7.55 (d, 1H), 7.49-7.42 (m, 2H), 7.35-7.31 (m, 4H), 7.19 (d, 1H), 7.13 (s, 1H) |
| 26 | 9.23 (d, 1H), 8.34 (s, 1H), 7.55 (t, 2H), 7.40 (d, 1H), 7,28~7.30 (m, 5H), 7.23 (d, 2H), 7.08 (t, 1H), 7.03-7.00 (s, 6H), 6,62 (s, 2H), 6.52 (t, 2H), 6.46 (d, 4H) |
| 27 | 7.90 (d, 1H), 7.86-7.78 (m, 4H), 7.62-7.60 (m, 2H), 7.40 (s, 1H), 7.33-7.30 (m, 10H), 6.59 (t, 1H) |
| 28 | 8.08 (d, 1H), 7.86-7.84 (m, 2H), 7.78 (d, 1H), 7.67-7.62(m, 3H), 7.55 (t, 2H), 7.49-7.40 (m, 3H), 7.33-7.30 (m, 9H), 7.19 (s, 1H), 7.13 (s, 1H), 7.08 (t, 1H), 7.00 (t, 1H) |
| 29 | 7.77 (d, 1H), 7.67 (d, 2H), 7.55 (t, 1H), 7.49-7.40 (m, 8H), 7.32-7.29 (m, 7H), 7.19-7.13 (m, 4H), 7.08 (s, 1H), 6.99 (t, 1H) |
| 30 | 7.86 (d, 1H), 7.78 (t, 1H), 7.62-7.60 (m, 2H), 7.33-7.30 (m, 8H), 7.23(s, 2H), 7.01 (m, 4H), 6.62 (t, 2H), 6.59-6.52 (m, 3H), 6.46 (d, 4H) |
| 31 | 7.86 (d, 1H), 7.79-7.76 (m, 3H), 7.62-7.60 (m, 2H), 7.55(s, 1H), 7.46 (t, 1H), 7.40 (t, 1H), 7.34-7.30 (m, 14H), 7.08 (d, 1H), 7.00 (d, 1H), 6.59 (t, 1H) |
| 32 | 7.89-7.86 (m, 2H), 7.78-7.73 (m, 3H), 7.67-7.60 (m, 4H), 7.54 (t, 1H), 7.33-7.30 (m, 10H), 6.59 (d, 1H) |
| 33 | 7.62-7.60 (m, 2H), 7.49-7.42 (m, 3H), 7.30 (m, 4H), 7.23 (d, 2H), 7.19-7.13 (m, 3H), 7.01 (s, 4H), 6.62-6.52 (m, 5H), 6.46 (t, 4H) |
| 34 | 7.77 (d, 1H), 7.62-7.60 (m, 2H), 7.55 (s, 1H), 7.49-7.40 (m, 5H), 7.33-7.29 (m, 10H), 7.19 (t, 1H), 7.13 (d, 2H), 7.08 (t, 1H), 7.00 (s, 1H), 6.59 (t, 1H) |
| 35 | 7.89 (d, 1H), 7.73 (s, 1H), 7.67-7.60 (m, 4H), 7.54 (t, 1H), 7.49-7.40 (m, 3H), 7.32-7.30 (m, 7H), 7.19 (t, 1H), 7.13 (d, 2H), 6.59 (d, 1H) |
| 36 | 8.08 (d, 1H), 7.92 (t, 1H), 7.86 (t, 1H), 7.78 (d, 2H), 7.33-7.30 (m, 8H), 7.23 (s, 2H), 7.01 (s, 4H), 6.62 (t, 2H), 6.52 (s, 2H), 6.46 (t, 4H) |
| 37 | 8.08 (t, 1H), 7.92 (d, 1H), 7.86 (s, 1H), 7.78-7.76 (t, 3H), 7.55 (t, 1H), 7.46-7.40 (m, 2H), 7.33-7.30 (m, 14H), 7.08 (s, 1H), 7.00 (d, 1H) |
| 38 | 8.08 (d, 1H), 7.92 (s, 1H), 7.89(t, 1H), 7.86 (t, 1H), 7.78-7.73 (m, 3H), 7.67 (d, 2H), 7.54 (s, 1H), 7.35-7.31 (m, 10H) |
| 39 | 8.08 (d, 1H), 7.92 (s, 1H), 7.49-7.42 (m, 3H), 7.30 (t, 5H), 7.23 (t, 2H), 7.19-7.13 (m, 3H), 7.01 (s, 4H), 6.62 (d, 2H), 6.52 (t, 2H), 6.46 (s, 4H) |
| 40 | 8.08 (d, 1H), 7.92 (s, 1H), 7.77 (d, 1H), 7.55 (t, 1H), 7.49-7.40 (m, 5H), 7.33-7.30 (m, 11H), 7.19 (d, 1H), 7.13 (s, 2H), 7.08 (t, 1H), 7.00 (d, 1H), |

-continued

| Compound | NMR data |
|---|---|
| 41 | 8.08 (d, 1 H), 7.92 (s, 1H), 7.89 (t, 1H), 7.73(d, 1H), 7.67 (d, 2H), 7.54 (t, 1H), 7.49-7.42 (m, 3H), 7.32-7.30 (m, 7H), 7.19-7.10 (m, 3H) |
| 42 | 8.08 (s, 1H), 7.93-7.77 (m, 6H), 7.40 (t, 1H), 7.33-7.30 (m, 10H) |
| 43 | 8.59 (d, 1H), 8.08 (d, 1H), 7.92 (s, 1H), 7.78 (t, 1H), 7.75 (s, 1H), 7.38-7.30 (m, 7H), 7.23 (t, 2H), 7.01 (d, 4H), 6.62 (s, 2H), 6.52 (d, 2H), 6.46 (t, 4H) |
| 44 | 8.59 (t, 1H), 8.08 (d, 1H), 7.92 (s, 1H), 7.89 (d, 1H), 7.75-7.73 (m 2H), 7.67 (t, 2H), 7.54 (s, 1H), 7.49 (t, 1H), 7.38-7.30 (m, 8H), 7.13 (d, 1H) |
| 45 | 7.86 (s, 1H), 7.78-7.77 (m, 3H), 7.60 (d, 1H), 7.33-7.30 (m, 8H), 7.23 (d, 2H), 7.01 (d, 4H), 6.62-6.59 (m, 3H), 6.52 (s, 1H), 6.46 (s, 4H), |
| 46 | 7.86(d, 1H), 7.79-7.77 (m, 4H), 7.60 (s, 1H), 7.55 (t, 1H), 7.46-7.40 (m, 1H), 7.33-7.30 (m, 14H), 7.08 (t, 1H), 7.00 (d, 1H), 6.59 (s, 1H) |
| 47 | 7.86 (s, 1H), 7.78-7.76 (m, 4H), 7.60 (d, 1H), 7.55 (d, 1H), 7.46-7.40 (m, 2H), 7.33-7.30 (m, 14H), 7.08 (d, 1H), 7.00 (t, 1H), 6.59 (s, 1H) |
| 48 | 7.77 (t, 1H), 7.60 (d, 1H), 7.49-7.42 (m, 3H), 7.30 (s, 5H), 7.23 (t, 2H), 7.19-7.13 (m, 3H), 7.01 (d, 4H), 6.62 (s, 2H), 6.59-6.52 (m, 3H), 6.46 (d, 4H) |
| 49 | 7.77 (d, 2H), 7.60 (d, 1H), 7.55 (t, 1H), 7.49-7.40 (m, 5H), 7.32-7.29 (m, 11H), 7.19-7.13 (m, 3H), 7.08(s, 1H), 7.00 (t, 1H), 6.59 (d, 1H) |
| 50 | 7.89(d, 1H), 7.77-7.73 (m, 2H), 7.67 (t, 2H), 7.60 (d, 1H), 7.54 (s, 1H), 7.49 (s, 2H), 7.42 (t, 1H), 7.32-7.30 (m, 7H), 7.19 (d, 1H), 7.13 (s, 2H), 6.59 (t, 1H) |
| 51 | 8.08 (t, 1H), 7.92(t, 1H), 7.86 (d, 1H), 7.78 (t, 2H), 7.33-7.30 (m, 8H), 7.23 (s, 2H), 7.01 (d, 4H), 6.62 (t, 2H), 6.52 (s, 2H), 6.46 (d, 4H) |
| 52 | 8.08 (d, 1H), 7.92 (d, 1H), 7.78 (s, 2H), 7.33-7.30 (t, 8H), 7.23 (d, 2H), 7.01 (s, 4H), 6.62 (d, 2H), 6.52 (d, 2H), 6.46 (t, 4H) |
| 53 | 8.08 (d, 1H), 7.92 (s, 1H), 7.86 (d, 1H),7.79-7.76 (m, 4H), 7.55 (d, 1H), 7.46-7.40 (m, 2H), 7.33-7.30 (m, 14H), 7.08 (s, 1H), 7.00 (d, 1H) |
| 54 | 8.08 (d, 1H), 7.92 (s, 1H), 7.49-7.42 (s, 3H), 7.30-7.23 (m, 7H), 7.19-7.13 (m, 3H), 7.01 (d, 4H), 6.62 (s, 2H), 6.52 (d, 2H), 6.46 (d, 4H) |
| 55 | 8.08 (s, 1H), 7.92 (d, 1H), 7.77 (d, 1H), 7.55 (t, 1H), 7.49-7.40 (m, 4H), 7.30 (d, 11H), 7.19-7.13 (m, 3H), 7.08-7.00 (m, 2H) |
| 56 | 8.08 (d, 1H), 7.92 (s, 1H), 7.89 (t, 1H), 7.73-7.67 (m, 3H), 7.54 (d, 1H), 7.49-7.42 (m, 3H), 7.32-7.30 (m, 7H), 7.19-7.13 (m, 3H) |

Example 1

To manufacture an anode, a corning 15 Ω/$cm^2$ (1200 Å) ITO glass substrate was cut to a size of 50 mm×50 mm×0.7 mm and then sonicated in isopropyl alcohol and pure water each for five minutes, and then cleaned by ultrasonication, followed by ultraviolet (UV) irradiation for about 30 minutes, and exposure to ozone for washing. The resulting glass substrate was loaded into a vacuum deposition device.

2-TNATA was vacuum-deposited on the ITO glass substrate to form an HIL having a thickness of 600 Å on the anode, and then nicotinamide N-propylsulfonate (NPS) was vacuum-deposited on the HIL to form an HTL having a thickness of 300 Å.

2-TNATA was vacuum-deposited on the ITO glass substrate to form an HIL having a thickness of 600 Å on the anode, and then NPS was vacuum-deposited on the HIL to form a HTL having a thickness of 300 Å.

A mixture comprising 98 wt % of 9,10-bis(naphthalene-2-yl)anthracene (DNA) as a blue fluorescent host and 2 wt % of Compound 1 as a fluorescent dopant were co-deposited on the HTL to form an EML having a thickness of about 300 Å.

Alq3 was deposited on the EML to form an ETL having a thickness of 300 Å. LiF was vacuum-deposited on the ETL to form an EIL having a thickness of about 10 Å and Al was vacuum-deposited on the EIL to form a cathode having a thickness of about 3000 Å, thereby completing the manufacture of an organic light-emitting device having the LiF/Al electrodes.

Example 2

An organic light-emitting device was manufactured in the same manner as in Example 1, except that Compound 2, instead of NPB, was used to form the HTL, and blue phosphorescent host DNA and blue fluorescent dopant 4,4'-bis(2,2-diphenylvinyl)-1,1'-biphenyl (DPAVBi) were used to form the EML.

Example 3

An organic light-emitting device was manufactured in the same manner as in Example 1, except that Compound 3, instead of NPB, was used to form the HTL, and blue phosphorescent host DNA and blue fluorescent dopant DPAVBi were used to form the EML.

Example 4

An organic light-emitting device was manufactured in the same manner as in Example 1, except that Compound 4, instead of NPB, was used to form the HTL, and blue phosphorescent host DNA and blue fluorescent dopant DPAVBi were used to form the EML.

Example 5

An organic light-emitting device was manufactured in the same manner as in Example 1, except that blue fluorescent host DNA and Compound 5 as a blue phosphorescent dopant were co-deposited in a weight ratio of 98:2 to form an EML having a thickness of about 300 Å.

Example 6

An organic light-emitting device was manufactured in the same manner as in Example 1, except that Compound 12 as a green phosphorescent host and green phosphorescent dopant Irppy were co-deposited in a weight ratio of 91:9 to form an EML having a thickness of about 300 Å, and BCP was deposited on the EML to form an HBL having a thickness of about 50 Å.

Example 7

An organic light-emitting device was manufactured in the same manner as in Example 6, except that Compound 13 as a green phosphorescent host was used to form the ETL.

Example 8

An organic light-emitting device was manufactured in the same manner as in Example 6, except that Compound 19 as a green phosphorescent host was used to form the ETL.

Example 9

An organic light-emitting device was manufactured in the same manner as in Example 6, except that Compound 20 as a green phosphorescent host was used to form the ETL.

Example 10

An organic light-emitting device was manufactured in the same manner as in Example 6, except that Compound 21 as a green phosphorescent host was used to form the ETL.

Example 11

An organic light-emitting device was manufactured in the same manner as in Example 6, except that Compound 25 as a green phosphorescent host was used to form the ETL.

Example 12

An organic light-emitting device was manufactured in the same manner as in Example 6, except that Compound 26 as a green phosphorescent host was used to form the ETL.

Example 13

An organic light-emitting device was manufactured in the same manner as in Example 6, except that Compound 27 as a green phosphorescent host was used to form the ETL.

Example 14

An organic light-emitting device was manufactured in the same manner as in Example 6, except that Compound 28 as a green phosphorescent host was used to form the ETL.

Example 15

An organic light-emitting device was manufactured in the same manner as in Example 6, except that Compound 29 as a green phosphorescent host was used to form the ETL.

Example 16

An organic light-emitting device was manufactured in the same manner as in Example 6, except that Compound 36 as a green phosphorescent host was used to form the ETL.

Example 17

An organic light-emitting device was manufactured in the same manner as in Example 6, except that Compound 39 as a green phosphorescent host was used to form the ETL.

Example 18

An organic light-emitting device was manufactured in the same manner as in Example 6, except that Compound 45 as a green phosphorescent host was used to form the ETL.

Example 19

An organic light-emitting device was manufactured in the same manner as in Example 6, except that Compound 51 as a green phosphorescent host was used to form the ETL.

Example 20

An organic light-emitting device was manufactured in the same manner as in Example 6, except that Compound 54 as a green phosphorescent host was used to form the ETL.

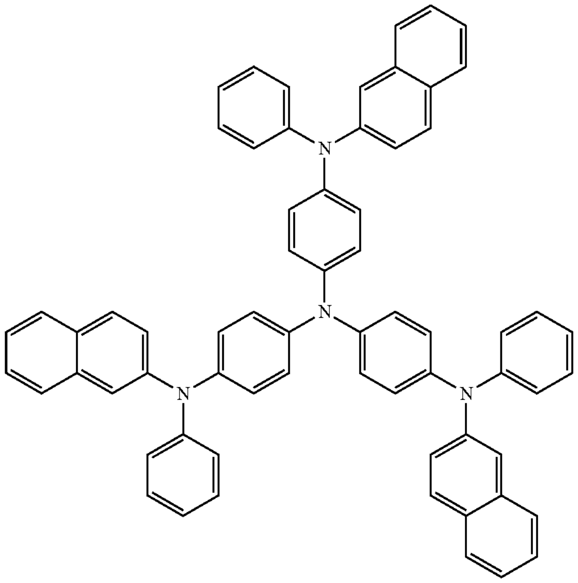

2-TNATA

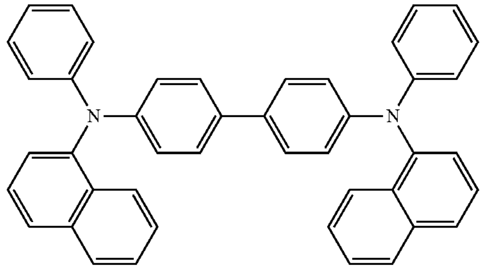

NPB

-continued

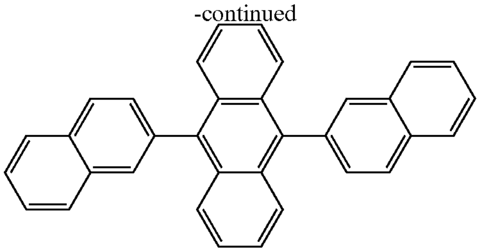

DNA

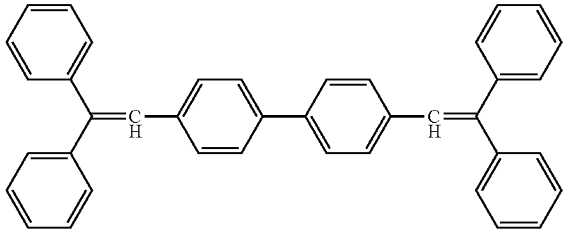

DPVBi

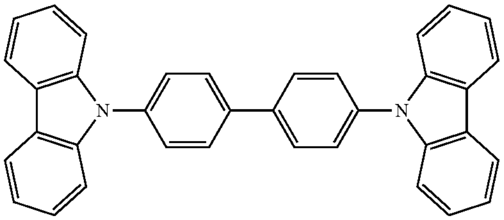

CBP

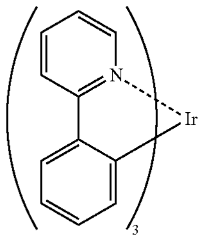

Irppy

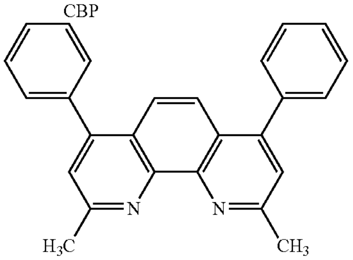

BCP

Comparative Example 1

An organic light-emitting device was manufactured in the same manner as in Example 5, except that blue fluorescent host DNA and blue fluorescent dopant DPVBi were co-deposited in a weight ratio of 98:2 to form an EML having a thickness of about 300 Å.

Comparative Example 2

An organic light-emitting device was manufactured in the same manner as in Example 6, except that blue phosphorescent host CBP and blue phosphorescent dopant Irppy were co-deposited in a weight ratio of 91:9 to form an EML having a thickness of about 300 Å.

Evaluation Example

Driving voltage, luminosity, luminescent efficiency, and lifetime of the organic light-emitting devices of Examples 1 to 20 and Comparative Examples 1 and 2 were measured using a PR650 (Spectroscan) source measurement unit (available from PhotoResearch, Inc.). The results are shown in Table 1 below.

TABLE 1

| Example | Driving voltage (V) | Current density ($mA/cm^2$) | Luminosity ($cd/m^2$) | Luminescent efficiency (cd/A) | Emission color | $LT_{97}$ lifetime (hr @ 100 $mA/cm^2$) |
|---|---|---|---|---|---|---|
| Example 1 | 5.95 | 50 | 1,903 | 3.8 | blue | 35 |
| Example 2 | 5.90 | 50 | 2,010 | 4.0 | blue | 34 |
| Example 3 | 5.88 | 50 | 2,453 | 4.9 | blue | 30 |
| Example 4 | 6.10 | 50 | 2,441 | 4.8 | blue | 35 |
| Example 5 | 6.07 | 50 | 2,551 | 5.1 | blue | 35 |
| Example 6 | 5.42 | 50 | 16,382 | 32.8 | green | 87 |
| Example 7 | 5.42 | 50 | 14,453 | 28.9 | green | 84 |
| Example 8 | 5.10 | 50 | 14,651 | 29.3 | green | 83 |
| Example 9 | 5.30 | 50 | 15,151 | 30.3 | green | 88 |
| Example 10 | 5.24 | 50 | 15,601 | 31.2 | green | 83 |
| Example 11 | 5.44 | 50 | 16,753 | 33.5 | green | 86 |
| Example 12 | 5.51 | 50 | 18,253 | 36.5 | green | 86 |
| Example 13 | 5.64 | 50 | 17,150 | 34.3 | green | 87 |
| Example 14 | 5.30 | 50 | 16,701 | 33.4 | green | 83 |
| Example 15 | 5.10 | 50 | 14,253 | 28.5 | green | 83 |
| Example 16 | 5.03 | 50 | 13,653 | 27.3 | green | 81 |
| Example 17 | 5.17 | 50 | 12,899 | 25.8 | green | 82 |
| Example 18 | 5.24 | 50 | 13,785 | 27.6 | green | 85 |
| Example 19 | 5.10 | 50 | 14,491 | 29.0 | green | 85 |
| Example 20 | 5.03 | 50 | 12,703 | 25.4 | green | 84 |
| Comparative Example 1 | 7.35 | 50 | 1,522 | 3.04 | blue | 15 |
| Comparative Example 2 | 6.8 | 50 | 10,902 | 21.8 | green | 60 |

Referring to Table 1, the organic light-emitting devices of Examples 1 to 5 are found to have improved driving voltage characteristics, a greatly improved luminescent efficiency, and remarkable improvements in luminosity and lifetime, as compared with the organic light-emitting device of Comparative Example 1.

In particular, the organic light-emitting device of Example 5 had a lower driving voltage by about 1.2V and a higher luminescent efficiency by about 60%, and a two or more times longer lifetime ($LT_{97}$) as compared with the organic light-emitting device of Comparative Example 1.

Referring to Table 6, the organic light-emitting devices of Examples 6 to 20 are found to have improved driving voltage characteristics and improved current/voltage/luminosity (I-V-L) characteristics with great improvements in luminescent efficiency, and in particular, with remarkable improvements in luminosity and lifetime, as compared with the organic light-emitting device of Comparative Example 2.

In particular, the organic light-emitting device of Example 6 had a lower driving voltage by about 1.9V and a higher luminescent efficiency by about 1000%, and a 400% or greater longer lifetime ($LT_{97}$), as compared with the organic light-emitting device of Comparative Example 1.

The organic light-emitting devices of Examples 1 to 20 are found to have high efficiency, low voltage, high luminosity, and long lifetime, as compared with existing organic light-emitting devices.

According to the one or more embodiments, the heterocyclic compounds of Formula 1 above may have a high glass transition temperature that is high enough to prevent crystallization, and improved electrical stability, high charge transport capability, and high emission capability. The heterocyclic compound of Formula 1 may be used as a light-emitting material in any color, such as red, green, blue, or white, or as an electron transporting material for fluorescent or phosphorescent organic light-emitting devices, and exhibits improved light-emitting characteristics.

According to the one or more embodiments of the present invention, the organic light-emitting device may include the heterocyclic compound of Formula 1 above as a light-emitting material or an electron-transporting material, and thus have a high efficiency, a low voltage, a high luminosity, and long lifetime.

According to embodiments, an organic light-emitting display apparatus including the organic light-emitting device may have an increased lifetime and an increased power efficiency with reduced power consumption.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

<Formula 1>

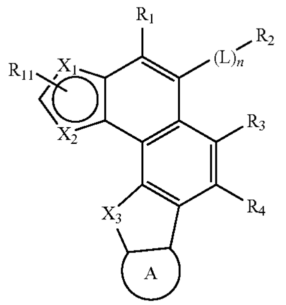

$X_1$ and $X_2$ of Formula 1 each independently being one selected from —C($R_{12}$)═, —N═, —N($R_{13}$)—, —O—, and —S—, and at least one of $X_1$ and $X_2$ being selected from —N═, —N($R_{13}$)—, —O—, and —S—, when $X_1$ being one selected from —C($R_{12}$)═ and —N═, $X_2$ being one selected from —N($R_{13}$)—, —O—, and —S—, when $X_1$ being one selected from —N($R_{13}$)—, —O—, and —S—, $X_2$ being one selected from —C($R_{12}$)═ and —N═;

$X_3$ being selected from —N($R_{21}$)—, —O—, and —S—, when $X_1$ being —S—, $X_3$ being selected from —N($R_{21}$)— and —O—;

$R_1$, $R_2$, $R_3$, $R_4$, $R_{11}$, $R_{12}$, $R_{13}$, and $R_{21}$ each independently being one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, and a —N($Q_1$)($Q_2$) group, $Q_1$ and $Q_2$ each independently being one of a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_2$-$C_{30}$ heteroaryl group;

L being selected from a substituted or unsubstituted $C_6$-$C_{30}$ arylene group and a substituted or unsubstituted $C_2$-$C_{30}$ hetero arylene group;

n being an integer of 0 to 3;

A being selected from a substituted or unsubstituted $C_6$-$C_{30}$ aromatic ring and a substituted or unsubstituted $C_2$-$C_{30}$ heteroaromatic ring; and $R_{11}$ and $R_{12}$ being selectively bound together to form one of a substituted or unsubstituted $C_6$-$C_{30}$ aromatic ring and a substituted or unsubstituted $C_2$-$C_{30}$ heteroaromatic ring.

2. The heterocyclic compound of claim 1, the heterocyclic compound being represented by one of Compounds 2a to 2t below:

<Formula 2a>

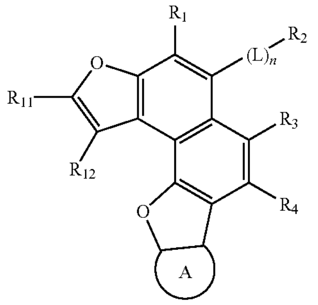

<Formula 2b>

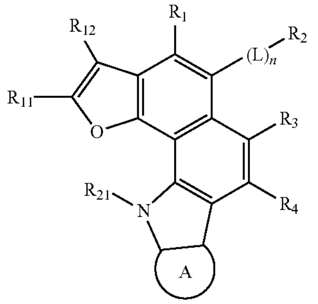

<Formula 2c>

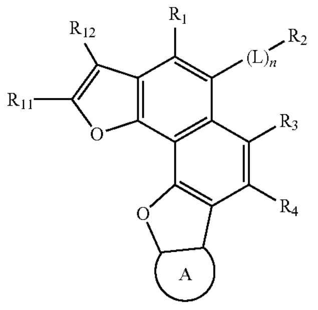

-continued
<Formula 2d>
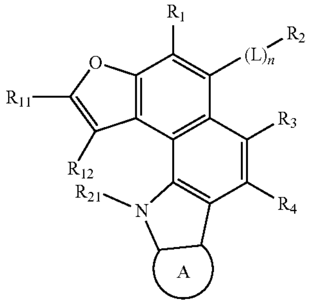
<Formula 2e>
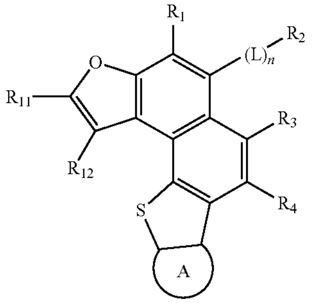
<Formula 2f>
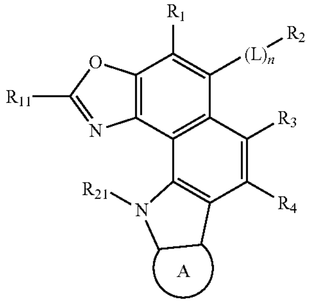
<Formula 2g>
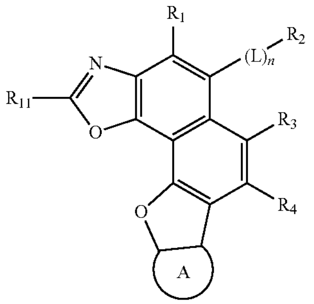
<Formula 2h>
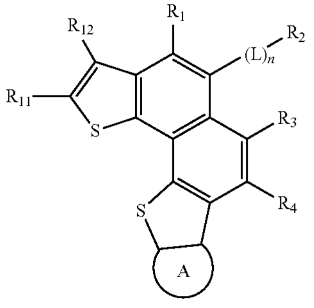
-continued
<Formula 2i>
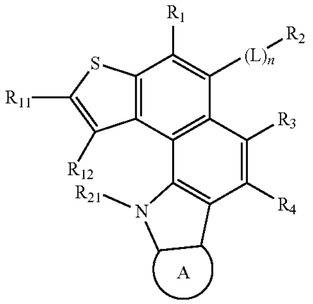
<Formula 2j>
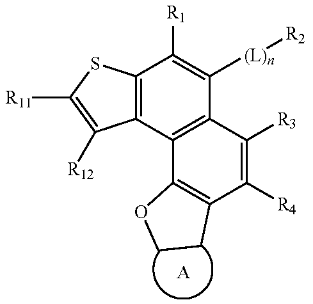
<Formula 2k>
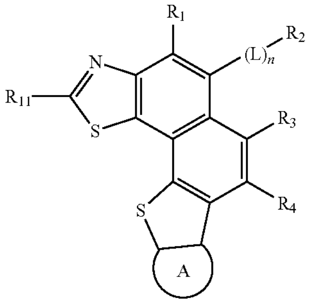
<Formula 2l>
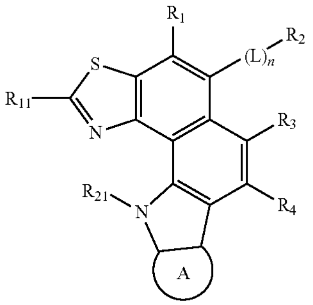
<Formula 2m>
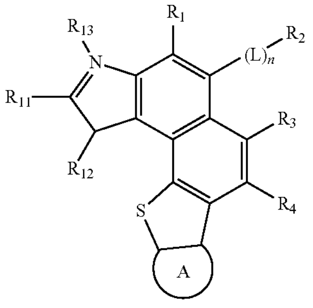

-continued

<Formula 2n>

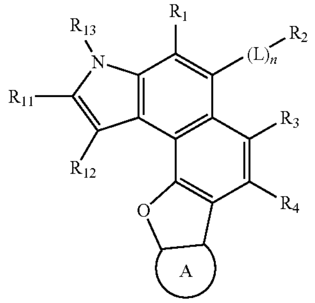

<Formula 2o>

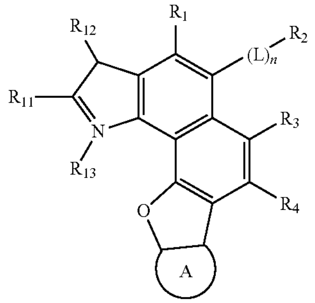

<Formula 2p>

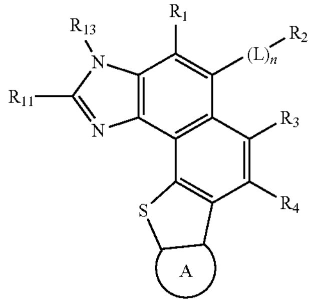

<Formula 2q>

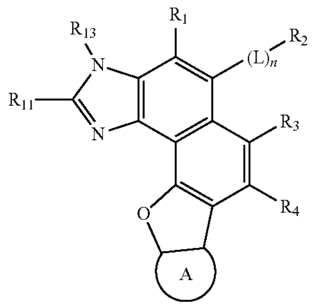

<Formula 2r>

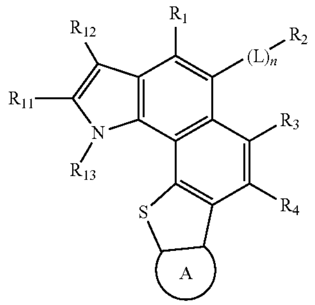

-continued

<Formula 2s>

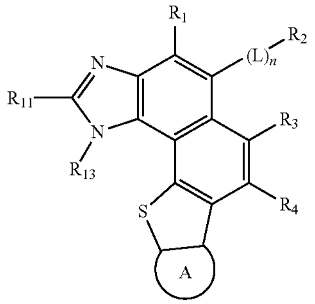

<Formula 2t>

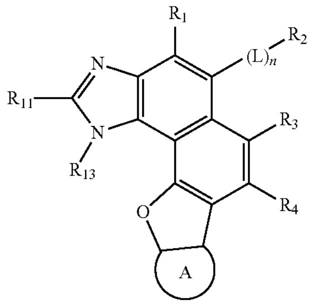

$R_1$, $R_2$, $R_3$, $R_4$, $R_{11}$, $R_{12}$, $R_{13}$, $R_{21}$, L, n, and A ring in Formulae 2a to 2t being as defined in Formula 1.

3. The heterocyclic compound of claim 1, the ring A being one selected from among a substituted or unsubstituted benzene ring, a substituted or unsubstituted naphthalene ring, a substituted or unsubstituted anthracene ring, a substituted or unsubstituted phenanthrene ring, and a substituted or unsubstituted pyridine ring.

4. The heterocyclic compound of claim 1, the ring A being represented by one of the Formulae 3a to 3e below:

<Formula 3a>

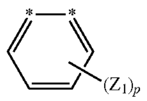

<Formula 3b>

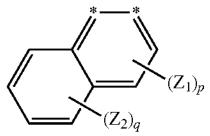

<Formula 3c>

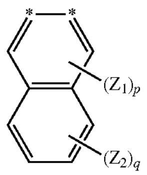

<Formula 3d>

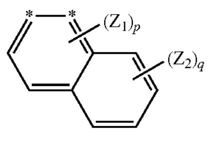

-continued

<Formula 3e>

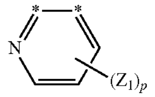

$Z_1$ and $Z_2$ in Formulae 3a to 3e each independently being one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted phenyl group, and a substituted or unsubstituted biphenyl group;

in Formula 3a, p is an integer of 2 to 4;

in Formula 3b, Formula 3c, and Formula 3d, p is 2 and q is an integer of 2 to 4;

in Formula 3e, p is an integer of 2 or 3; and an asterisk (*) indicating a binding site of the ring A with the rest of the heterocyclic compound.

5. The heterocyclic compound of claim 1, the ring A being represented by one of the Formulae 4a to 1e below:

<Formula 4a>

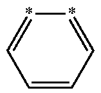

<Formula 4b>

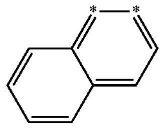

<Formula 4c>

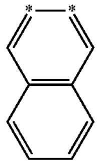

<Formula 4d>

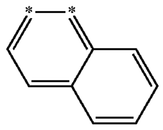

<Formula 4e>

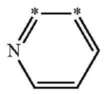

an asterisk (*) in Formulae 4a to 4e indicating a binding site of the ring A with the rest of the heterocyclic compound.

6. The heterocyclic compound of claim 1, $R_{11}$ and $R_{12}$ being bound together to form a substituted or unsubstituted benzene ring.

7. The heterocyclic compound of claim 1, $R_1$, $R_2$, $R_3$, $R_4$, $R_{11}$, $R_{12}$, $R_{13}$, and $R_{21}$ each independently being selected from a hydrogen atom, a deuterium atom, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted biphenyl group, a substituted or unsubstituted naphthyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted naphthacenyl group, a substituted or unsubstituted fluorenyl group, a substituted or unsubstituted pyridinyl), substituted or unsubstituted bipyridinyl group, a substituted or unsubstituted pyrazinyl group, a substituted or unsubstituted pyrimidinyl group, a substituted or unsubstituted pyridazinyl group, a substituted or unsubstituted quinolinyl group, a substituted or unsubstituted isoquinolinyl group, a substituted or unsubstituted carbazolyl group, a substituted or unsubstituted benzothiophenyl group, a substituted or unsubstituted dibenzothiophenyl group, a substituted or unsubstituted benzofuranyl group, a substituted or unsubstituted dibenzofuranyl group, and a group represented by $—N(Q_3)(Q_4)$, $Q_3$ and $Q_4$ each independently being selected from a substituted or unsubstituted phenyl group, a substituted or unsubstituted biphenyl group, and a substituted or unsubstituted naphthyl group.

8. The heterocyclic compound of claim 1, $R_2$ being one of the groups represented by Formulae 5a to 5i:

<Formula 5a>

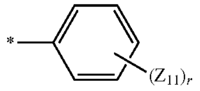

<Formula 5b>

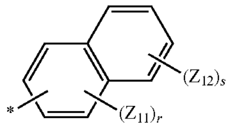

<Formula 5c>

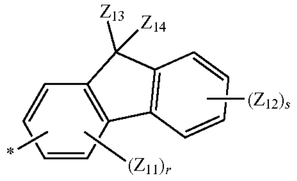

<Formula 5d>

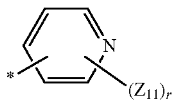

<Formula 5e>

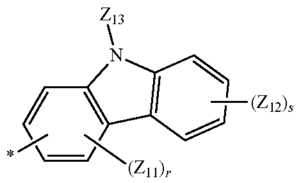

<Formula 5f>

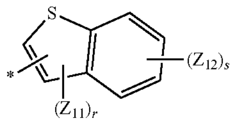

<Formula 5g>

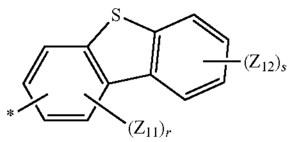

-continued

<Formula 5h>

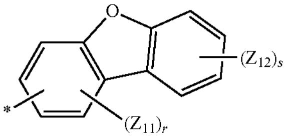

<Formula 5i>

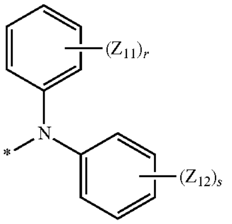

$Z_{11}$ to $Z_{14}$ in Formulae 5a to 5i each independently being one of a hydrogen atom, a deuterium atom, a halogen atom, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted propoxy group, a substituted or unsubstituted butoxy group, a substituted or unsubstituted phenyl group, and a substituted or unsubstituted biphenyl group;

in Formula 5a, r is an integer from 1 to 5;

in Formula 5b, Formula 5c, Formula 5e, Formula 5g, and Formula 5h, r is an integer of 1 to 3, and s is an integer of 1 to 4;

in Formula 5d, r is an integer of 1 to 4;

in Formula 5f, r is 1, and s is an integer of 1 to 4;

in Formula 5i, r and s are independently integers from 1 to 5; and an asterisk (*) indicating a binding site of $R_2$ with the rest of the heterocyclic compound.

9. The heterocyclic compound of claim 1, $R_2$ being one of the groups represented by Formulae 6a to 6i:

<Formula 6a>

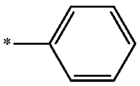

<Formula 6b>

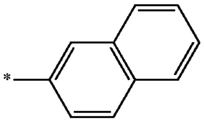

<Formula 6c>

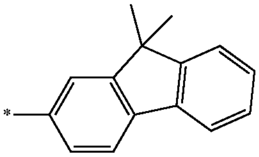

<Formula 6d>

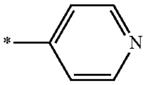

-continued

<Formula 6e>

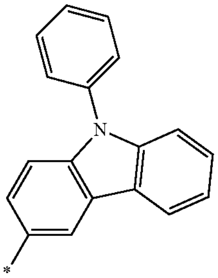

<Formula 6f>

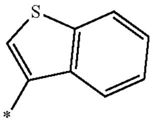

<Formula 6g>

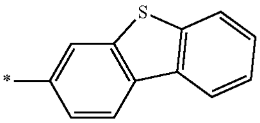

<Formula 6h>

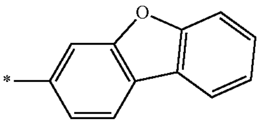

<Formula 6i>

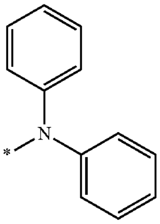

an asterisk (*) in Formulae 6a to 6i indicating a binding site of $R_2$ with the rest of the heterocyclic compound.

10. The heterocyclic compound of claim 1, L being selected from a phenylene group, a naphthalene group, and an anthracene group, and n being 0 or 1.

11. The heterocyclic compound of claim 1, the heterocyclic compound being one of Compounds 1 to 56 below:

1

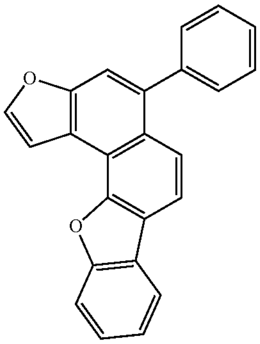

-continued
2
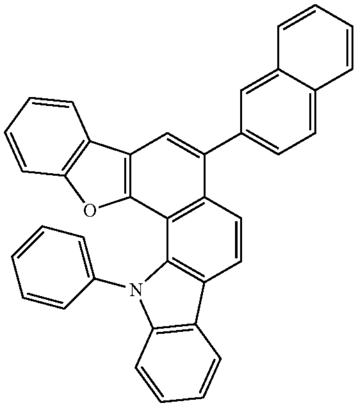
3
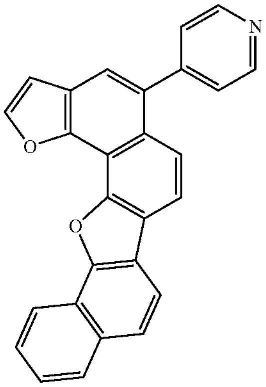
4
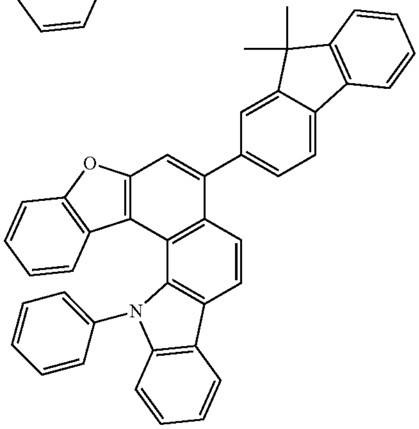
5
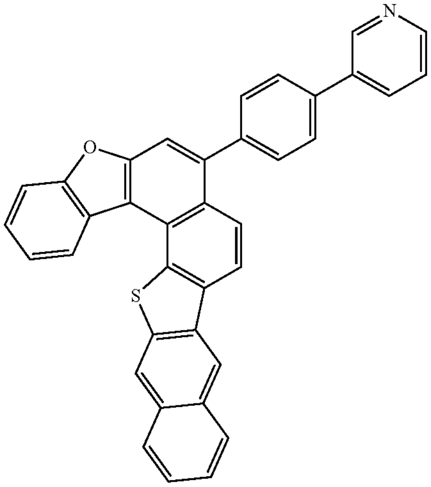
-continued
6
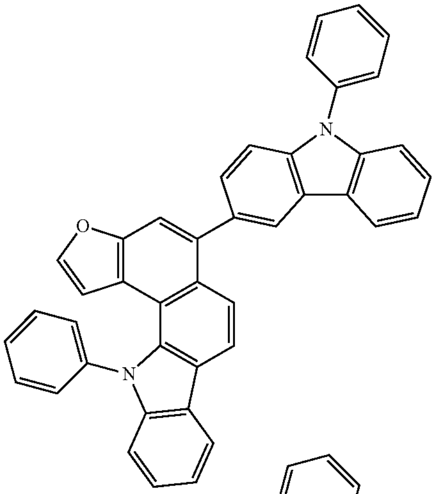
7
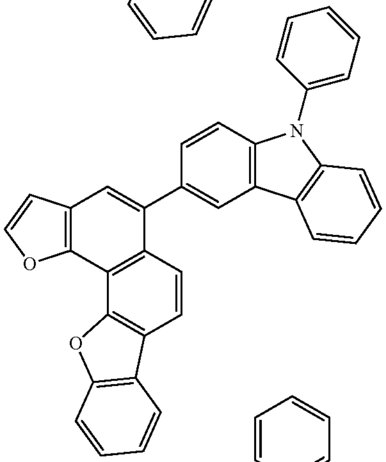
8
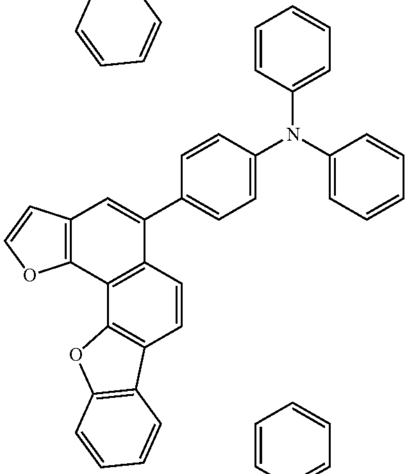
9
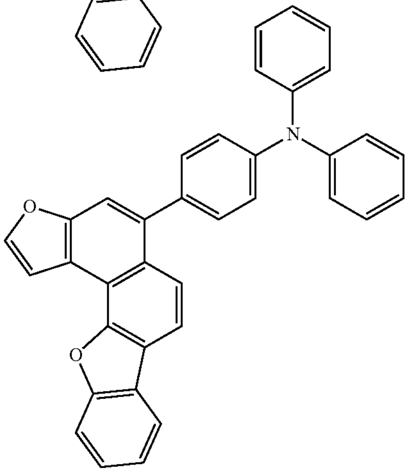

-continued
10
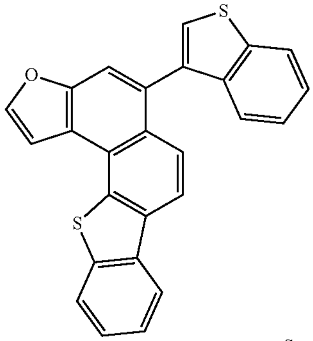
11
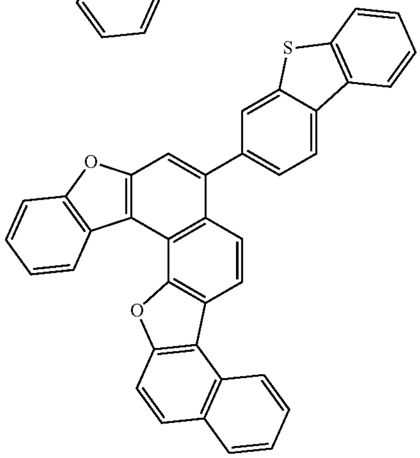
12
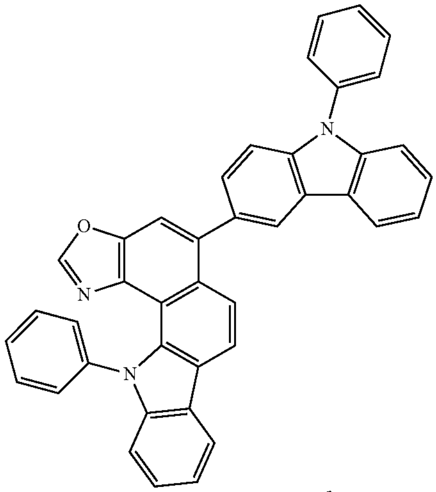
13
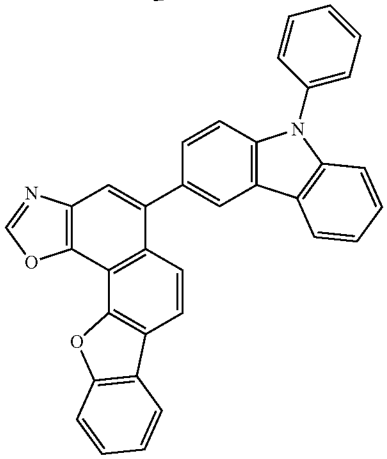
-continued
14
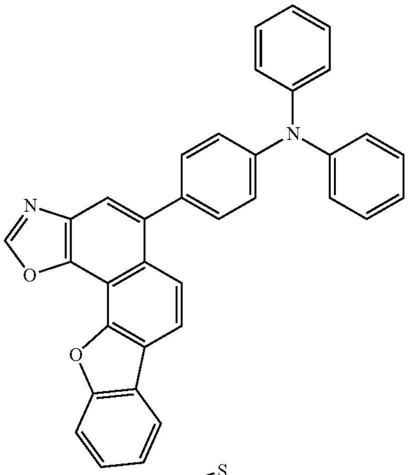
15
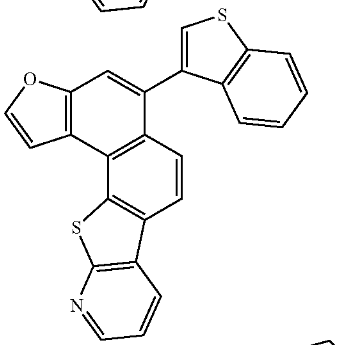
16
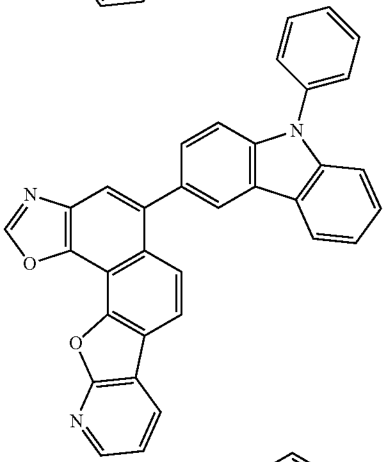
17
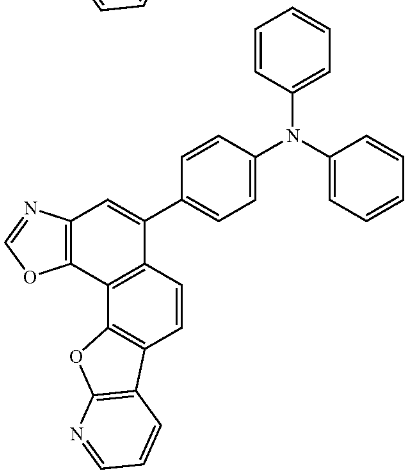

-continued
18
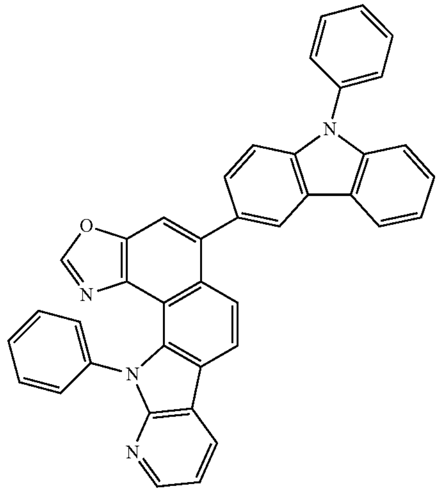
19
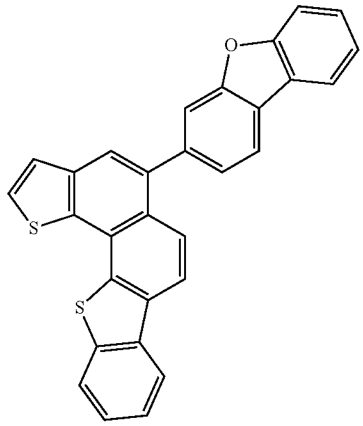
20
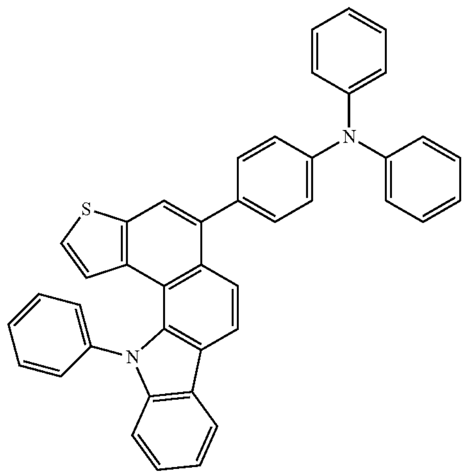
-continued
21
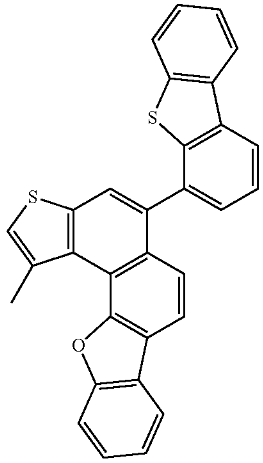
22
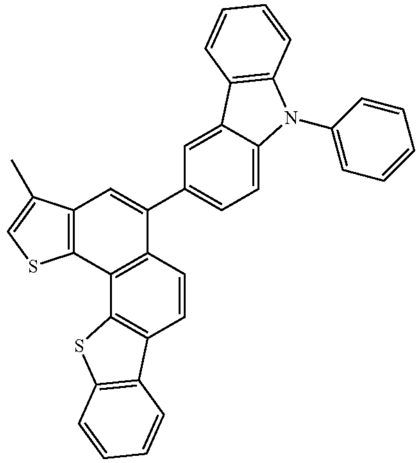
23
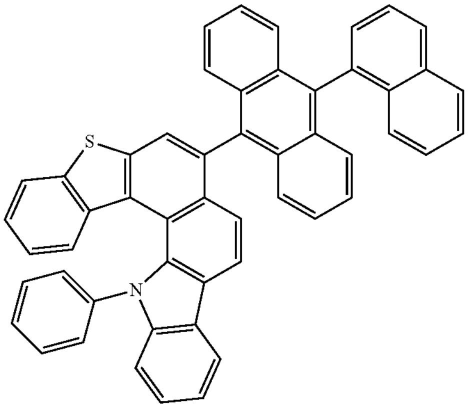

-continued
24
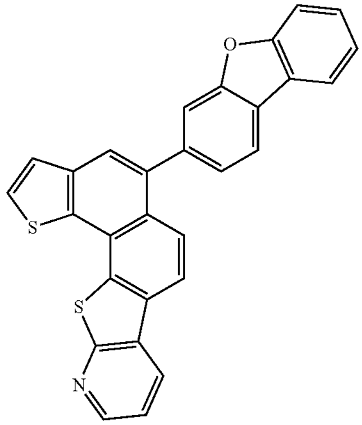
25
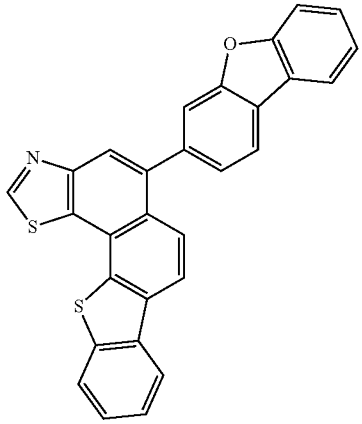
26
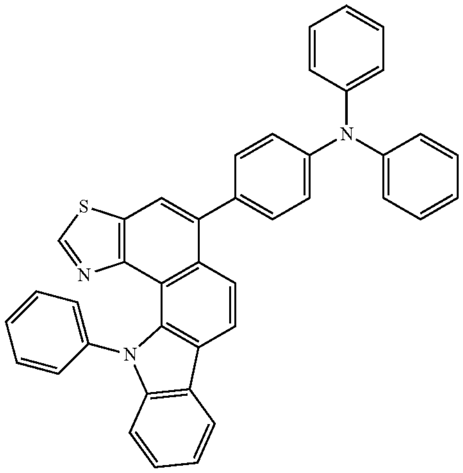
-continued
27
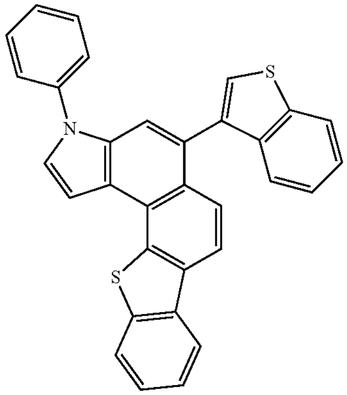
28
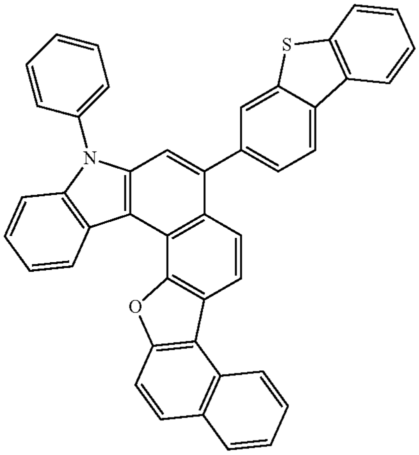
29
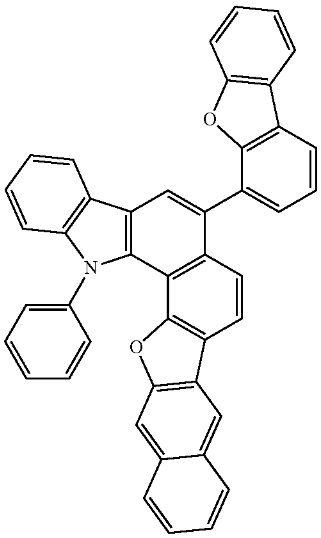

-continued
30
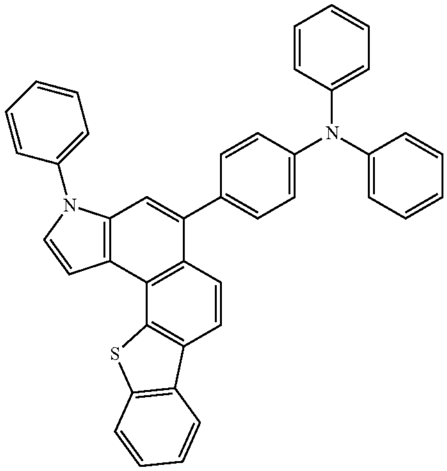
31
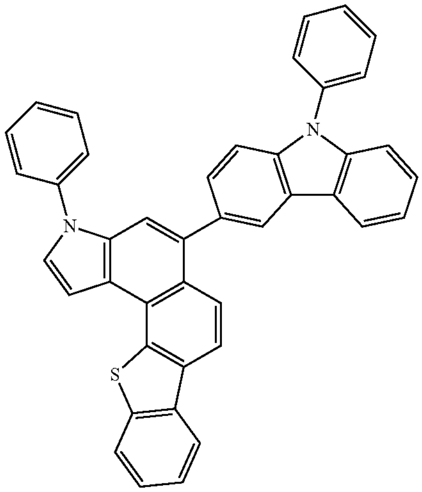
32
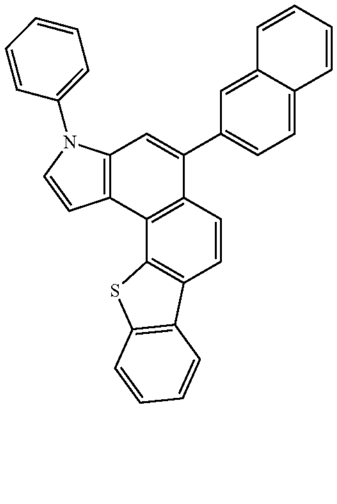
-continued
33
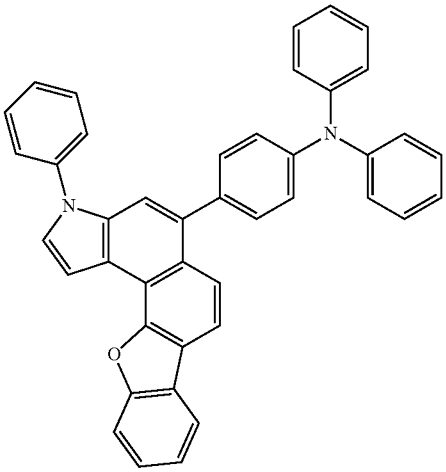
34
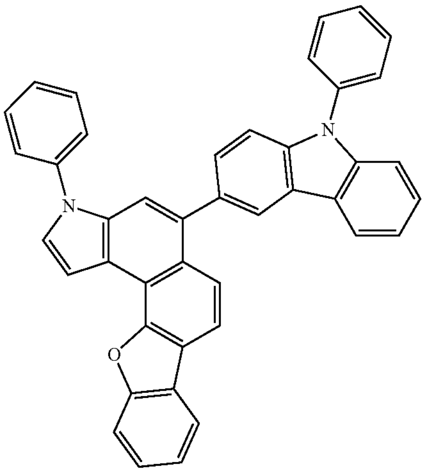
35
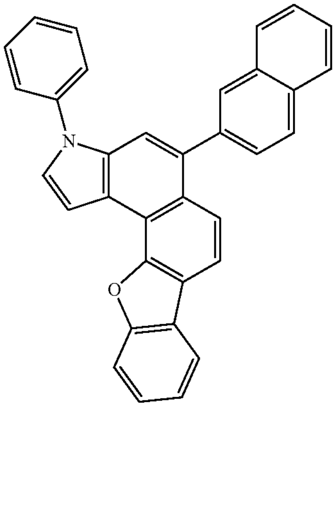

-continued
36
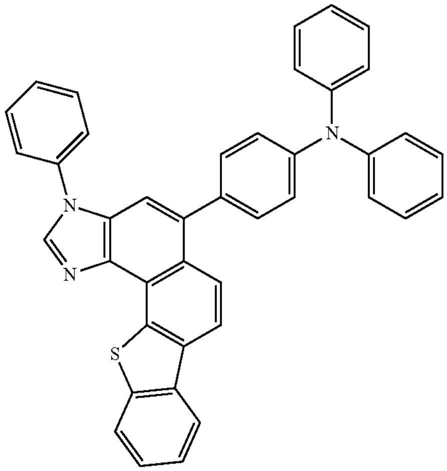
37
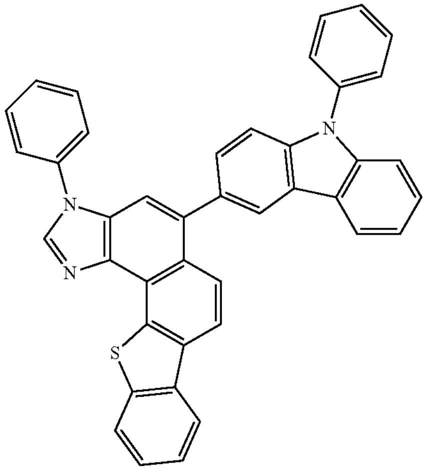
38
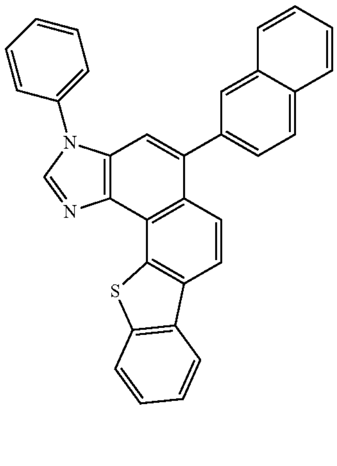
-continued
39
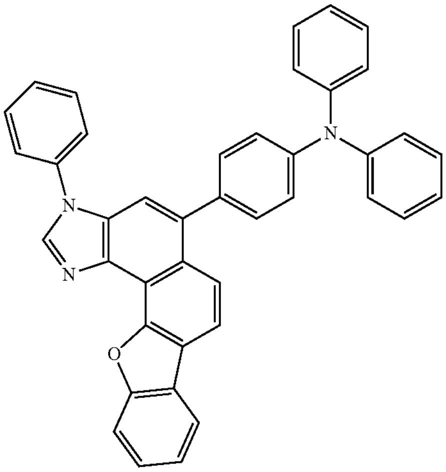
40
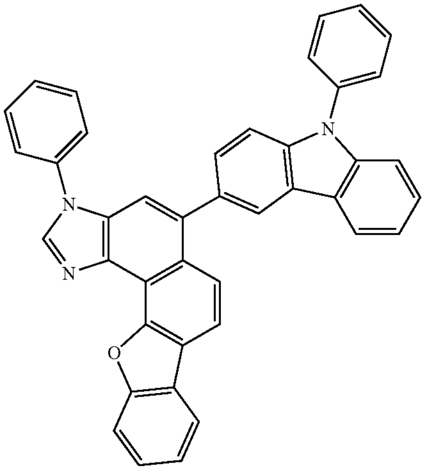
41
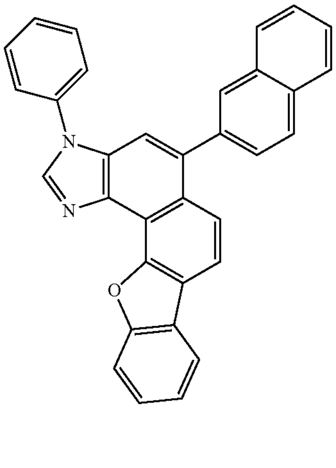

-continued
42
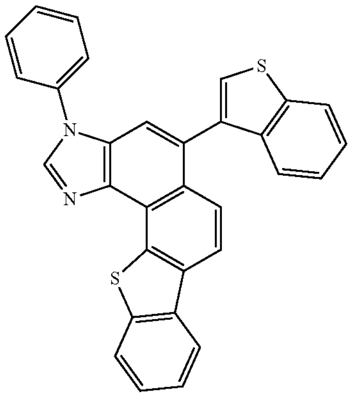
43
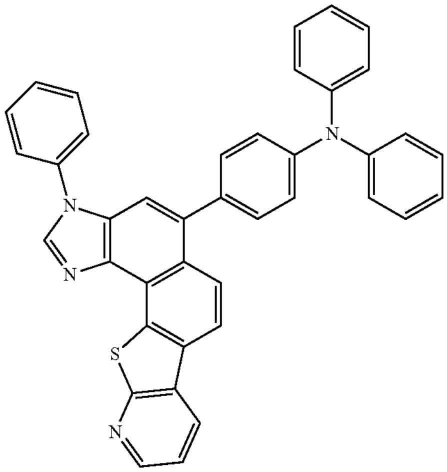
44
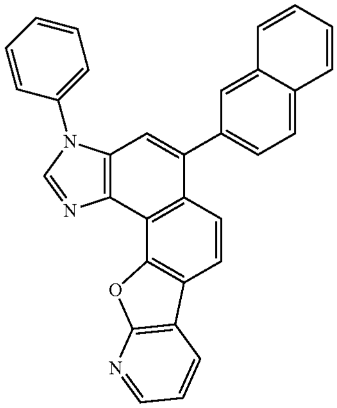
-continued
45
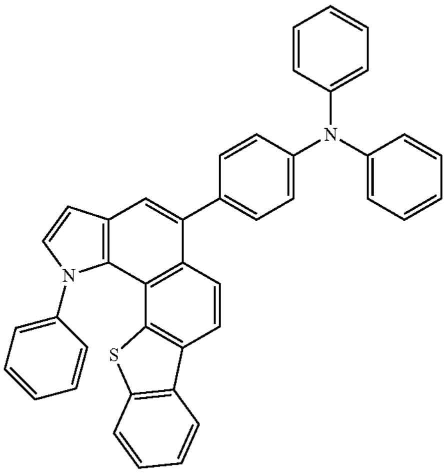
46
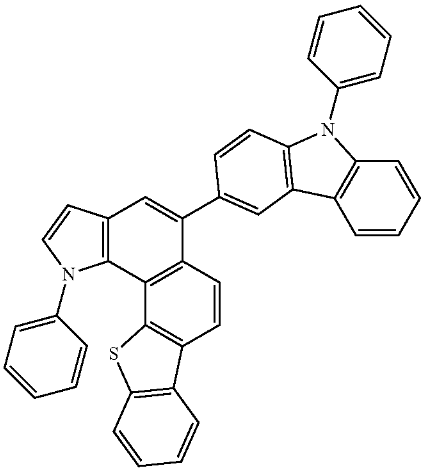
47
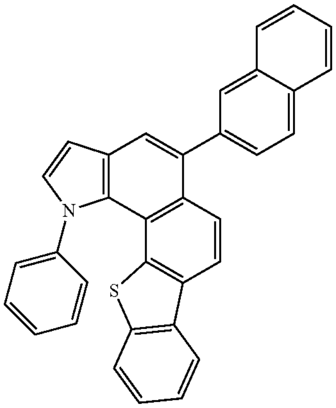

-continued
48
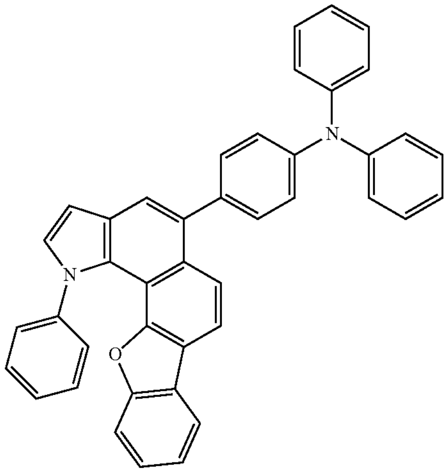
49
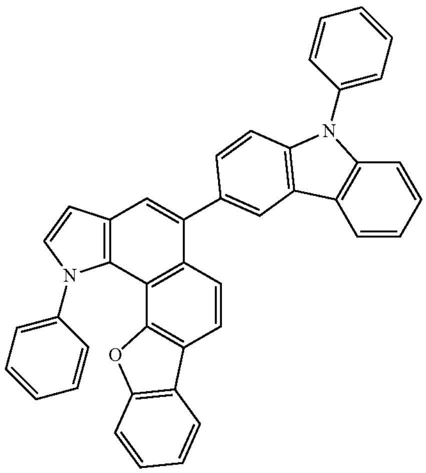
50
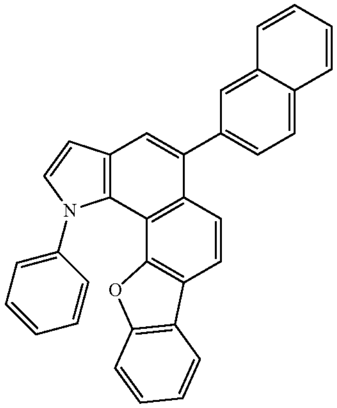
-continued
51
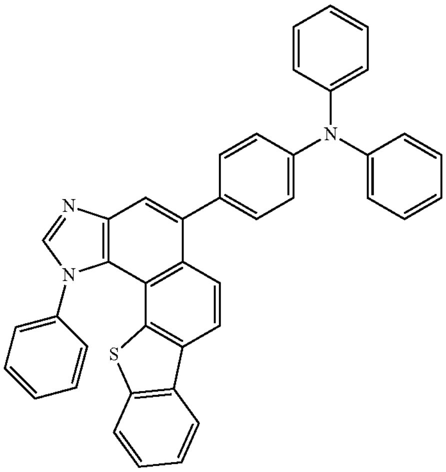
52
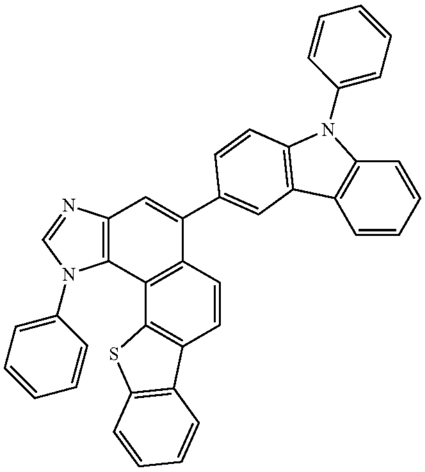
53
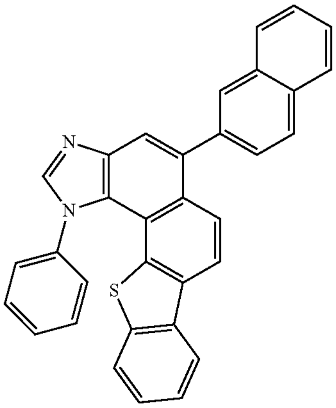

-continued

54

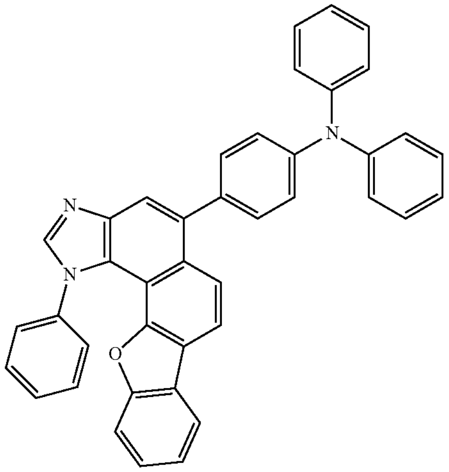

55

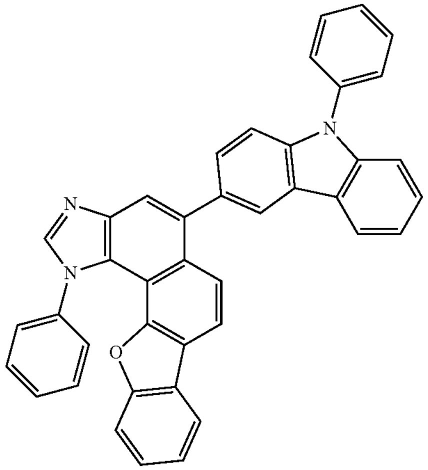

56

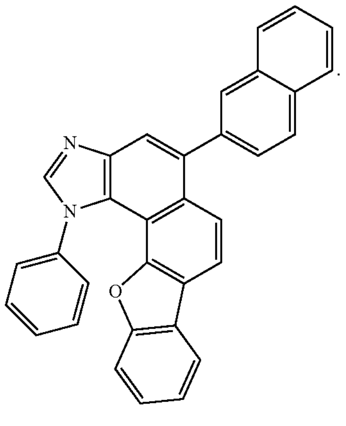

12. An organic light-emitting device comprising a first electrode, a second electrode disposed opposite to the first electrode, and an organic layer disposed between the first electrode and the second electrode, the organic layer comprising at least one of the heterocyclic compounds defined by claim 1.

13. The organic light-emitting device of claim 12, the organic layer comprising at least one of a hole injection layer, a hole transport layer, a functional layer having both hole injection and hole transport capabilities, a buffer layer, an emission layer, a hole blocking layer, an electron transport layer, an electron injection layer, and a functional layer having both electron injection and electron transport capabilities.

14. The organic light-emitting device of claim 12, the organic layer comprising at least one of a hole injection layer, a hole transport layer, and a functional layer having both hole injection and hole transport capabilities, at least one of the hole injection layer, the hole transport layer, and the functional layer having both hole injection and hole transport capabilities comprising the at least one heterocyclic compound.

15. The organic light-emitting device of claim 12, the organic layer comprising at least one of an electron injection layer, an electron transport layer, and a functional layer having both electron injection and electron transport capabilities, at least one of the electron injection layer, the electron transport layer, and the functional layer having both electron injection and electron transport capabilities comprising the at least one heterocyclic compound.

16. The organic light-emitting device of claim 12, the organic layer comprising an emission layer, the emission layer comprising the at least one heterocyclic compound.

17. The organic light-emitting device of claim 16, the at least one heterocyclic compound being used as a fluorescent or phosphorescent host.

18. The organic light-emitting device of claim 16, the at least one heterocyclic compound being used as a fluorescent dopant.

19. The organic light-emitting device of claim 12, the organic layer comprising at least one of an emission layer, an electron injection layer, an electron transport layer, and a functional layer having both electron injection and electron transport capabilities, at least one of the electron injection layer, the electron transport layer, and the functional layer having both electron injection and electron transport capabilities comprising the at least one heterocyclic compound, the emission layer comprising an arylamine compound.

20. An organic light-emitting display device, comprising:

a transistor comprising a source, a drain, a gate, and an active layer; and the organic light-emitting device according to claim 12, one of the source and the drain of the transistor being electrically connected to the first electrode of the organic light-emitting device.

* * * * *